United States Patent
Wersland et al.

(10) Patent No.: US 11,890,253 B2
(45) Date of Patent: *Feb. 6, 2024

(54) PERCUSSIVE THERAPY DEVICE WITH INTERCHANGEABLE MODULES

(71) Applicant: Therabody, Inc., Los Angeles, CA (US)

(72) Inventors: Jason Wersland, Los Angeles, CA (US); Benjamin Nazarian, Los Angeles, CA (US); Jaime Sanchez Solana, Los Angeles, CA (US); Eduardo Merino, Los Angeles, CA (US)

(73) Assignee: Therabody, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/739,630

(22) Filed: May 9, 2022

(65) Prior Publication Data
US 2022/0257460 A1  Aug. 18, 2022

Related U.S. Application Data

(63) Continuation-in-part of application No. 17/244,239, filed on Apr. 29, 2021, now Pat. No. 11,452,670, (Continued)

(51) Int. Cl.
*A61H 23/00* (2006.01)
*A61N 5/06* (2006.01)

(52) U.S. Cl.
CPC ... *A61H 23/006* (2013.01); *A61H 2201/0107* (2013.01); *A61H 2201/0153* (2013.01);
(Continued)

(58) Field of Classification Search
CPC .......... A61H 1/00; A61H 1/006; A61H 1/008; A61H 2230/50; A61H 39/00;
(Continued)

(56) References Cited

U.S. PATENT DOCUMENTS

| | | |
|---|---|---|
| 657,765 A | 9/1900 | Gibbs |
| 675,772 A | 6/1901 | Ferguson |

(Continued)

FOREIGN PATENT DOCUMENTS

| | | |
|---|---|---|
| AT | 510048 A1 | 1/2012 |
| AU | 2019204770 B1 | 10/2019 |

(Continued)

OTHER PUBLICATIONS

TheraGun device in YouTube video "TheraGun: What It Does," https://www.youtube.com/watch?v=FB_JTZnD7vs; Aug. 24, 2016 (upload date).

(Continued)

*Primary Examiner* — Colin W Stuart
(74) *Attorney, Agent, or Firm* — Sterne, Kessler, Goldstein & Fox P.L.L.C.

(57) ABSTRACT

A percussive therapy device includes a housing, an electrical source, a motor positioned in the housing, a switch for activating the motor, and a push rod assembly operatively connected to the motor and configured to reciprocate in response to activation of the motor. A massage attachment is removably received on a distal end of the push rod assembly at a first location. The percussive therapy device also includes an attachment module associated with the housing of the percussive therapy device at a second location. The second location is different than the first location. The attachment module is configured to provide an active effect.

12 Claims, 59 Drawing Sheets

Related U.S. Application Data which is a continuation-in-part of application No. 17/018,099, filed on Sep. 11, 2020, now Pat. No. 11,357,697, which is a continuation-in-part of application No. 16/869,402, filed on May 7, 2020, now Pat. No. 10,857,064, which is a continuation-in-part of application No. 16/796,143, filed on Feb. 20, 2020, now Pat. No. 10,940,081, said application No. 16/869,402 is a continuation-in-part of application No. 16/675,772, filed on Nov. 6, 2019, now Pat. No. 10,702,448, application No. 17/739,630 is a continuation-in-part of application No. 17/705,300, filed on Mar. 26, 2022, which is a continuation-in-part of application No. 17/361,966, filed on Jun. 29, 2021, now Pat. No. 11,331,244.

(60) Provisional application No. 63/185,927, filed on May 7, 2021, provisional application No. 63/133,591, filed on Jan. 4, 2021, provisional application No. 63/133,530, filed on Jan. 4, 2021, provisional application No. 63/065,348, filed on Aug. 13, 2020, provisional application No. 63/045,365, filed on Jun. 29, 2020, provisional application No. 63/017,472, filed on Apr. 29, 2020, provisional application No. 62/912,392, filed on Oct. 8, 2019, provisional application No. 62/899,098, filed on Sep. 11, 2019, provisional application No. 62/844,424, filed on May 7, 2019, provisional application No. 62/785,151, filed on Dec. 26, 2018.

(52) U.S. Cl.
CPC .............. *A61H 2201/0207* (2013.01); *A61H 2201/0214* (2013.01); *A61H 2201/10* (2013.01); *A61H 2201/1207* (2013.01); *A61H 2201/1669* (2013.01); *A61H 2201/1685* (2013.01); *A61H 2201/5064* (2013.01); *A61H 2201/5069* (2013.01); *A61N 5/062* (2013.01)

(58) Field of Classification Search
CPC .... A61H 39/002; A61H 39/007; A61H 39/04; A61H 23/00; A61H 23/004; A61H 23/006; A61H 23/02; A61H 23/0218; A61H 23/0254; A61H 23/0263; A61H 23/04; A61H 23/06; A61H 2023/002; A61H 2023/0209; A61H 2023/0272; A61H 2023/0281; A61H 2023/029; A61H 2201/0165; A61H 2201/12; A61H 2201/1207; A61H 2201/1215; A61H 2201/1223; A61H 2201/123; A61H 2201/02; A61H 2201/0207; A61H 2201/10; A61H 2201/0221; A61H 2201/1238; A61H 2201/14; A61H 2201/1409; A61H 2201/1418; A61H 2201/1481; A61H 2201/149; A61H 2201/1664; A61H 2201/50; A61H 2201/5007; A61H 2201/501; A61H 2201/5012; A61H 2201/5058; A61H 2201/5061; A61H 2201/5097; A61H 2201/5043; A61H 2201/5084; A61H 2201/5082; A61H 2201/5064; A61H 2201/5046; A61H 2201/5069; A61H 2201/5071
See application file for complete search history.

(56) References Cited

U.S. PATENT DOCUMENTS

| | | |
|---|---|---|
| 1,545,027 A | 7/1925 | Ashlock |
| 1,594,636 A | 8/1926 | Smith |
| 1,657,765 A | 1/1928 | Pasque |
| 1,784,301 A | 12/1930 | Mekler |
| D91,454 S | 2/1934 | Decker |
| D93,943 S | 11/1934 | Rand |
| 2,179,594 A | 11/1939 | Johnson |
| D118,980 S | 2/1940 | Larson |
| D129,045 S | 8/1941 | Wilhide |
| 2,391,671 A | 12/1945 | Berg |
| D143,678 S | 1/1946 | Wiser |
| 2,475,861 A | 7/1949 | Alfred |
| D161,484 S | 1/1951 | McQuown |
| D163,324 S | 5/1951 | Rittenhouse |
| D180,923 S | 9/1957 | Anton |
| D181,742 S | 12/1957 | Madl |
| 2,931,632 A | 4/1960 | Angelis |
| 2,987,334 A | 6/1961 | Wendling |
| 3,053,559 A | 9/1962 | Norval |
| 3,077,837 A | 2/1963 | Sidney et al. |
| D195,145 S | 4/1963 | Ernest |
| D197,142 S | 12/1963 | Godfrey |
| 3,172,675 A | 3/1965 | Gonzalez |
| D207,505 S | 4/1967 | Whitman |
| 3,452,226 A | 6/1969 | Hettich |
| 3,545,301 A | 12/1970 | Richter |
| 3,626,934 A | 12/1971 | Andis |
| 3,699,952 A | 10/1972 | Waters et al. |
| 3,705,579 A | 12/1972 | Morini et al. |
| D230,522 S | 2/1974 | Rothman |
| D237,454 S | 11/1975 | Adams |
| D237,455 S | 11/1975 | Schramm |
| 3,942,251 A | 3/1976 | Griffies |
| 3,968,789 A | 7/1976 | Simoncini |
| 4,031,763 A | 6/1977 | Eisenberg |
| 4,046,142 A | 9/1977 | Whitney |
| 4,088,128 A | 5/1978 | Mabuchi |
| 4,150,668 A | 4/1979 | Johnston |
| 4,158,246 A | 6/1979 | Meadows et al. |
| 4,173,217 A | 11/1979 | Johnston |
| 4,203,431 A | 5/1980 | Abura et al. |
| D265,985 S | 8/1982 | House |
| 4,506,159 A | 3/1985 | Reuter et al. |
| 4,513,737 A | 4/1985 | Mabuchi |
| 4,533,796 A | 8/1985 | Engelmore |
| 4,549,535 A | 10/1985 | Wing |
| 4,565,189 A | 1/1986 | Mabuchi |
| 4,566,442 A | 1/1986 | Mabuchi |
| 4,596,406 A | 6/1986 | Van Vleet et al. |
| D287,814 S | 1/1987 | Hiraishi |
| 4,691,693 A | 9/1987 | Sato |
| 4,692,958 A | 9/1987 | McMakin |
| D292,368 S | 10/1987 | Mikiya |
| 4,730,605 A | 3/1988 | Noble |
| D300,132 S | 3/1989 | Culbertson |
| 4,815,224 A | 3/1989 | Miller |
| 4,841,955 A | 6/1989 | Evans et al. |
| D303,373 S | 9/1989 | Ching, Jr. |
| D310,005 S | 8/1990 | Precht |
| D314,320 S | 2/1991 | Brosius |
| 4,989,613 A | 2/1991 | Finkenberg |
| 4,991,298 A | 2/1991 | Matre |
| 5,014,681 A | 5/1991 | Heeman et al. |
| D320,379 S | 10/1991 | Culbertson |
| D321,338 S | 11/1991 | Sakamoto |
| 5,085,207 A | 2/1992 | Fiore |
| 5,088,474 A | 2/1992 | Mabuchi et al. |
| 5,092,317 A | 3/1992 | Zelikovski |
| 5,103,809 A | 4/1992 | DeLuca et al. |
| 5,123,139 A | 6/1992 | Leppert et al. |
| D329,166 S | 9/1992 | Doggett |
| D329,291 S | 9/1992 | Wollman |
| D329,292 S | 9/1992 | Wollman |
| D331,467 S | 12/1992 | Wollman |
| D334,012 S | 3/1993 | Chen |

(56) References Cited

U.S. PATENT DOCUMENTS

| | | |
|---|---|---|
| 5,201,149 A | 4/1993 | Eisenblatter |
| 5,207,697 A | 5/1993 | Carusillo et al. |
| 5,212,887 A | 5/1993 | Farmerie |
| D338,802 S | 8/1993 | Maass |
| D345,077 S | 3/1994 | Maass |
| D345,727 S | 4/1994 | Flowers |
| D345,888 S | 4/1994 | Joss |
| D349,029 S | 7/1994 | Matsunaga |
| 5,417,644 A | 5/1995 | Lee |
| D363,352 S | 10/1995 | Huen |
| D367,712 S | 3/1996 | Young |
| 5,501,657 A | 3/1996 | Feero |
| D374,934 S | 10/1996 | Lie |
| 5,569,168 A | 10/1996 | Hartwig |
| 5,573,500 A | 11/1996 | Katsunuma |
| 5,656,017 A | 8/1997 | Keller |
| 5,656,018 A | 8/1997 | Tseng |
| D383,366 S | 9/1997 | Heck |
| D383,435 S | 9/1997 | Svetlik |
| D384,639 S | 10/1997 | Kawakami |
| D387,728 S | 12/1997 | Kawakami |
| D388,175 S | 12/1997 | Lie |
| D397,991 S | 9/1998 | Kawakami |
| D400,161 S | 10/1998 | Nagele |
| D400,758 S | 11/1998 | Hippen |
| 5,860,669 A | 1/1999 | Wass et al. |
| D408,543 S | 4/1999 | Back |
| 5,910,197 A | 6/1999 | Chaconas |
| 5,925,002 A | 7/1999 | Wollman |
| D412,485 S | 8/1999 | Kato |
| 5,935,089 A | 8/1999 | Shimizu |
| 5,951,501 A | 9/1999 | Griner |
| D417,648 S | 12/1999 | Clowers |
| 6,003,052 A | 12/1999 | Yamagata |
| 6,006,631 A | 12/1999 | Miner et al. |
| D425,014 S | 5/2000 | Willkens |
| D430,774 S | 9/2000 | Naft |
| D430,938 S | 9/2000 | Lee |
| D432,077 S | 10/2000 | Zurwelle |
| D433,300 S | 11/2000 | Buck |
| 6,146,383 A | 11/2000 | Studer et al. |
| 6,165,145 A | 12/2000 | Noble |
| D439,984 S | 4/2001 | Thach |
| D440,136 S | 4/2001 | Buck |
| 6,227,959 B1 | 5/2001 | Beaudry |
| 6,228,042 B1 | 5/2001 | Dungan |
| 6,228,120 B1 | 5/2001 | Leonard et al. |
| 6,245,031 B1 | 6/2001 | Pearson |
| 6,290,660 B1 | 9/2001 | Epps et al. |
| D448,852 S | 10/2001 | Engelen |
| 6,401,289 B1 | 6/2002 | Herbert |
| 6,406,445 B1 | 6/2002 | Ben-Nun |
| 6,432,072 B1 | 8/2002 | Harris et al. |
| 6,537,236 B2 | 3/2003 | Tucek et al. |
| 6,539,328 B1 | 3/2003 | Cremonese et al. |
| D474,445 S | 5/2003 | Matsuoka |
| 6,558,338 B1 | 5/2003 | Wasserman |
| 6,568,089 B1 | 5/2003 | Popik et al. |
| D475,595 S | 6/2003 | Hatch |
| D475,679 S | 6/2003 | Cooper |
| D476,746 S | 7/2003 | Harris |
| 6,599,250 B2 | 7/2003 | Webb et al. |
| 6,599,260 B2 | 7/2003 | Tucek |
| D478,385 S | 8/2003 | Dirks |
| D481,279 S | 10/2003 | Buck |
| 6,663,657 B1 | 12/2003 | Miller |
| 6,682,496 B1 | 1/2004 | Pivaroff |
| 6,715,781 B1 | 4/2004 | Smith |
| 6,723,050 B2 | 4/2004 | Dow et al. |
| 6,723,060 B2 | 4/2004 | Miller |
| 6,758,826 B2 | 7/2004 | Luettgen et al. |
| 6,805,700 B2 | 10/2004 | Miller |
| 6,823,762 B2 | 11/2004 | Hu |
| 6,846,295 B1 | 1/2005 | Ben-Nun |
| D504,111 S | 4/2005 | Ozawa |
| D510,317 S | 10/2005 | Sun |
| 6,994,575 B1 | 2/2006 | Clark et al. |
| 7,041,072 B2 | 5/2006 | Calvert |
| D530,270 S | 10/2006 | Ozawa |
| 7,128,721 B2 | 10/2006 | Ferber et al. |
| D531,733 S | 11/2006 | Burout |
| 7,169,169 B2 | 1/2007 | Tucek et al. |
| 7,223,250 B2 | 5/2007 | Brattesani et al. |
| D544,102 S | 6/2007 | Pivaroff |
| D544,436 S | 6/2007 | Kawahara |
| D547,264 S | 7/2007 | Kondo |
| D553,252 S | 10/2007 | Masuda |
| D553,562 S | 10/2007 | Okada |
| 7,384,405 B2 | 6/2008 | Rhoades |
| D575,224 S | 8/2008 | Taniguchi |
| 7,431,706 B2 | 10/2008 | Louis |
| D579,868 S | 11/2008 | Harrison |
| D580,353 S | 11/2008 | Harrison |
| 7,470,081 B2 | 12/2008 | Miyahara et al. |
| D587,977 S | 3/2009 | Waldron |
| 7,497,639 B2 | 3/2009 | Lebot et al. |
| 7,503,923 B2 | 3/2009 | Miller |
| D593,204 S | 5/2009 | Manke |
| 7,549,966 B2 | 6/2009 | Fujii et al. |
| D597,482 S | 8/2009 | Kondo |
| D604,235 S | 11/2009 | Tarter |
| D605,586 S | 12/2009 | Tong |
| D606,192 S | 12/2009 | Summerer et al. |
| 7,731,672 B2 | 6/2010 | Chiang |
| 7,740,249 B1 | 6/2010 | Gao |
| D622,660 S | 8/2010 | Taniguchi |
| 7,857,729 B2 | 12/2010 | Sullivan et al. |
| D631,315 S | 1/2011 | Xue |
| 7,877,880 B2 | 2/2011 | Royle |
| 7,927,259 B1 | 4/2011 | Rix |
| 7,927,294 B2 | 4/2011 | Kamimura et al. |
| 7,963,717 B2 | 6/2011 | Seger |
| 7,996,996 B2 | 8/2011 | Hirabayashi |
| D649,657 S | 11/2011 | Petersen et al. |
| D658,759 S | 5/2012 | Marescaux et al. |
| D659,644 S | 5/2012 | Gretz |
| D666,303 S | 8/2012 | Ding |
| 8,313,450 B2 | 11/2012 | Ben-Nun |
| 8,342,187 B2 | 1/2013 | Kalman |
| D682,195 S | 5/2013 | Aglassinger |
| 8,435,194 B2 | 5/2013 | Dverin et al. |
| 8,479,616 B2 | 7/2013 | Tsai |
| 8,622,943 B2 | 1/2014 | Ben-Nun |
| 8,646,348 B2 | 2/2014 | Hung |
| D703,337 S | 4/2014 | Fuhr et al. |
| D703,480 S | 4/2014 | Lownds |
| 8,695,461 B2 | 4/2014 | Moss et al. |
| D706,433 S | 6/2014 | Fuhr et al. |
| D708,742 S | 7/2014 | Dallemagne et al. |
| 8,770,882 B2 | 7/2014 | Ersoy |
| 8,777,881 B2 | 7/2014 | Tsai |
| 8,864,143 B2 | 10/2014 | Lin |
| D722,016 S | 2/2015 | Beukema |
| 8,945,104 B2 | 2/2015 | Boone |
| 8,951,216 B2 | 2/2015 | Yoo |
| D726,495 S | 4/2015 | Ryan |
| 9,017,273 B2 | 4/2015 | Burbank et al. |
| D734,863 S | 7/2015 | Hennessey |
| D735,348 S | 7/2015 | Hennessey |
| 9,107,486 B2 | 8/2015 | Brewer et al. |
| 9,132,058 B2 | 9/2015 | Imboden et al. |
| 9,138,257 B2 | 9/2015 | Revivo |
| D740,222 S | 10/2015 | Tang |
| 9,272,837 B2 | 3/2016 | Linzell |
| D756,180 S | 5/2016 | Chen |
| D759,237 S | 6/2016 | Heath et al. |
| D759,238 S | 6/2016 | Heath et al. |
| 9,364,385 B2 | 6/2016 | Yang |
| D763,442 S | 8/2016 | Price et al. |
| 9,416,805 B2 | 8/2016 | Cascolan et al. |
| D776,612 S | 1/2017 | Chen |
| D778,439 S | 2/2017 | Håkansson et al. |
| 9,597,256 B1 | 3/2017 | Paul |
| 9,744,600 B2 | 8/2017 | Yang et al. |

(56) References Cited

U.S. PATENT DOCUMENTS

| | | |
|---|---|---|
| 9,872,813 B2 | 1/2018 | Giraud et al. |
| 9,889,066 B2 * | 2/2018 | Danby ............... A61H 23/0254 |
| D817,732 S | 5/2018 | Rettler |
| D817,869 S | 5/2018 | Lee |
| D819,221 S | 5/2018 | Lei |
| 9,981,366 B2 | 5/2018 | Todd et al. |
| D823,478 S | 7/2018 | Park |
| 10,034,813 B1 | 7/2018 | Silver |
| D826,418 S | 8/2018 | Lad |
| D837,395 S | 1/2019 | Gan |
| D838,378 S | 1/2019 | Cao |
| D840,547 S | 2/2019 | Harle et al. |
| 10,201,470 B2 | 2/2019 | Griner |
| D842,489 S | 3/2019 | Spewock |
| D842,491 S | 3/2019 | Fleming et al. |
| D843,656 S | 3/2019 | Zhang et al. |
| D844,896 S | 4/2019 | Levi et al. |
| D847,362 S | 4/2019 | Tang |
| D847,364 S | 4/2019 | Lee et al. |
| 10,252,051 B2 | 4/2019 | Nichols |
| 10,276,844 B2 | 4/2019 | Wackwitz |
| D847,990 S | 5/2019 | Kimball |
| 10,314,762 B1 | 6/2019 | Marton |
| 10,335,345 B2 | 7/2019 | Choe |
| 10,357,425 B2 | 7/2019 | Wersland |
| D855,822 S | 8/2019 | Marton |
| D858,432 S | 9/2019 | Altenburger |
| D862,382 S | 10/2019 | Altenburger |
| D866,790 S | 11/2019 | Lee |
| D867,279 S | 11/2019 | Altenburger |
| 10,557,490 B2 | 2/2020 | Wersland et al. |
| D877,351 S | 3/2020 | Wersland |
| D880,419 S | 4/2020 | Hernandez et al. |
| D880,714 S | 4/2020 | Wersland et al. |
| D880,715 S | 4/2020 | Wersland et al. |
| D880,716 S | 4/2020 | Wersland et al. |
| D884,205 S | 5/2020 | Zhuang |
| 10,702,448 B2 | 7/2020 | Wersland et al. |
| D893,738 S | 8/2020 | Zhuang |
| 10,758,027 B2 | 9/2020 | Skidmore et al. |
| 10,857,064 B2 | 12/2020 | Wersland et al. |
| 10,918,565 B2 | 2/2021 | Wersland et al. |
| 10,945,915 B2 | 3/2021 | Wersland et al. |
| 10,959,908 B2 | 3/2021 | Lee et al. |
| 10,959,911 B2 | 3/2021 | Wersland et al. |
| D919,560 S | 5/2021 | Taniguchi |
| 10,993,874 B1 | 5/2021 | Marton et al. |
| 11,160,723 B2 | 11/2021 | Wersland et al. |
| 11,478,400 B1 | 10/2022 | Marton et al. |
| 11,478,606 B1 | 10/2022 | English et al. |
| 2001/0016697 A1 | 8/2001 | Gorsen |
| 2001/0027280 A1 | 10/2001 | Huang |
| 2002/0082532 A1 | 6/2002 | Tucek et al. |
| 2002/0115947 A1 | 8/2002 | Young |
| 2002/0177795 A1 | 11/2002 | Frye |
| 2002/0183668 A1 | 12/2002 | Huang |
| 2002/0188233 A1 | 12/2002 | Denyes |
| 2003/0009116 A1 | 1/2003 | Luettgen |
| 2003/0014079 A1 | 1/2003 | Tucek |
| 2003/0028134 A1 | 2/2003 | Lev et al. |
| 2003/0094356 A1 | 5/2003 | Waldron |
| 2003/0144615 A1 | 7/2003 | Lin |
| 2003/0195443 A1 | 10/2003 | Miller |
| 2004/0176710 A1 | 9/2004 | Kennedy et al. |
| 2005/0075591 A1 | 4/2005 | Hafemann |
| 2005/0109137 A1 | 5/2005 | Hartmann |
| 2005/0113870 A1 | 5/2005 | Miller |
| 2005/0126018 A1 | 6/2005 | Haas |
| 2005/0131461 A1 | 6/2005 | Tucek et al. |
| 2005/0203445 A1 | 9/2005 | Tsai |
| 2005/0235988 A1 | 10/2005 | Hansen et al. |
| 2005/0252011 A1 | 11/2005 | Neumeier |
| 2006/0025710 A1 | 2/2006 | Schulz |
| 2006/0047315 A1 | 3/2006 | Colloca et al. |
| 2006/0074455 A1 | 4/2006 | Strandberg |
| 2006/0116614 A1 | 6/2006 | Jones et al. |
| 2006/0118841 A1 | 6/2006 | Eliason et al. |
| 2006/0123941 A1 | 6/2006 | Wadge |
| 2006/0192527 A1 | 8/2006 | Kageler |
| 2006/0211961 A1 | 9/2006 | Meyer et al. |
| 2006/0272664 A1 | 12/2006 | O'Dwyer |
| 2007/0129220 A1 | 6/2007 | Bardha |
| 2007/0144310 A1 | 6/2007 | Pozgay |
| 2007/0150004 A1 | 6/2007 | Colloca |
| 2007/0173886 A1 | 7/2007 | Rousso |
| 2007/0179414 A1 | 8/2007 | Imboden et al. |
| 2007/0270727 A1 | 11/2007 | Khorassani Zadeh |
| 2007/0282228 A1 | 12/2007 | Einav et al. |
| 2008/0077061 A1 | 3/2008 | Dehli |
| 2008/0097260 A1 | 4/2008 | Tsukada et al. |
| 2008/0103419 A1 | 5/2008 | Adamson |
| 2008/0146980 A1 | 6/2008 | Rousso et al. |
| 2008/0167588 A1 | 7/2008 | Chen |
| 2008/0169715 A1 | 7/2008 | Mills et al. |
| 2008/0177207 A1 | 7/2008 | Liao |
| 2008/0185888 A1 | 8/2008 | Beall et al. |
| 2008/0200849 A1 | 8/2008 | Hollington et al. |
| 2008/0243041 A1 | 10/2008 | Brenner et al. |
| 2008/0306417 A1 | 12/2008 | Imboden et al. |
| 2008/0312568 A1 | 12/2008 | Chen |
| 2008/0314610 A1 | 12/2008 | Meixner |
| 2009/0112134 A1 * | 4/2009 | Avni .................. A61H 23/0263 601/46 |
| 2009/0188119 A1 | 7/2009 | Oberheim |
| 2009/0270777 A1 | 10/2009 | Wu et al. |
| 2009/0309313 A1 | 12/2009 | Knorr et al. |
| 2009/0326540 A1 | 12/2009 | Estes |
| 2010/0100119 A1 | 4/2010 | Herndon |
| 2010/0137907 A1 | 6/2010 | Tsai |
| 2010/0145242 A1 | 6/2010 | Tsai |
| 2010/0160841 A1 | 6/2010 | Wu |
| 2010/0162579 A1 | 7/2010 | Naughton et al. |
| 2010/0176919 A1 | 7/2010 | Myers et al. |
| 2010/0210194 A1 | 8/2010 | Thomaschewski et al. |
| 2010/0274162 A1 | 10/2010 | Evans |
| 2010/0286569 A1 | 11/2010 | Nagano |
| 2010/0298863 A1 | 11/2010 | Hindinger et al. |
| 2011/0037431 A1 | 2/2011 | Mackle |
| 2011/0055720 A1 | 3/2011 | Potter et al. |
| 2011/0118637 A1 | 5/2011 | Lev et al. |
| 2011/0201979 A1 | 8/2011 | Voss et al. |
| 2011/0224580 A1 | 9/2011 | Leathers |
| 2011/0314677 A1 | 12/2011 | Meier et al. |
| 2012/0059294 A1 | 3/2012 | Schubert et al. |
| 2012/0065556 A1 | 3/2012 | Smith et al. |
| 2012/0078071 A1 | 3/2012 | Bohm |
| 2012/0124758 A1 | 5/2012 | Sabisch et al. |
| 2012/0161706 A1 | 6/2012 | Zhou |
| 2012/0197357 A1 | 8/2012 | Dewey et al. |
| 2012/0232445 A1 | 9/2012 | Lev et al. |
| 2012/0238922 A1 | 9/2012 | Stemple et al. |
| 2012/0253245 A1 | 10/2012 | Stanbridge |
| 2013/0014968 A1 | 1/2013 | Kehoe et al. |
| 2013/0030506 A1 | 1/2013 | Bartolone et al. |
| 2013/0046212 A1 | 2/2013 | Nichols |
| 2013/0052871 A1 | 2/2013 | Eklind |
| 2013/0085421 A1 | 4/2013 | Gillespie et al. |
| 2013/0116503 A1 | 5/2013 | Mertens et al. |
| 2013/0133210 A1 | 5/2013 | Weir |
| 2013/0138023 A1 | 5/2013 | Lerro |
| 2013/0218058 A1 | 8/2013 | Ceoldo et al. |
| 2013/0237751 A1 | 9/2013 | Alexander |
| 2013/0241470 A1 | 9/2013 | Kim |
| 2013/0261516 A1 | 10/2013 | Cilea |
| 2013/0261517 A1 | 10/2013 | Rodgers |
| 2013/0271067 A1 | 10/2013 | Yu et al. |
| 2013/0281897 A1 | 10/2013 | Hoffmann |
| 2013/0304642 A1 | 11/2013 | Campos |
| 2014/0024982 A1 | 1/2014 | Doyle |
| 2014/0031866 A1 | 1/2014 | Fuhr et al. |
| 2014/0097793 A1 | 4/2014 | Wurtz et al. |
| 2014/0101872 A1 | 4/2014 | Utsch et al. |
| 2014/0163443 A1 | 6/2014 | Young et al. |
| 2014/0180331 A1 | 6/2014 | Turner |

(56) References Cited

U.S. PATENT DOCUMENTS

| | | |
|---|---|---|
| 2014/0190023 A1 | 7/2014 | Vitantonio et al. |
| 2014/0194900 A1 | 7/2014 | Sedic |
| 2014/0200495 A1 | 7/2014 | Jones |
| 2014/0207032 A1 | 7/2014 | Dematio |
| 2014/0209594 A1 | 7/2014 | Besner |
| 2014/0221887 A1 | 8/2014 | Wu |
| 2014/0288473 A1 | 9/2014 | Matsushita |
| 2014/0305747 A1 | 10/2014 | Kumar et al. |
| 2014/0310900 A1 | 10/2014 | Curry |
| 2014/0316313 A1 | 10/2014 | Mayer et al. |
| 2015/0005682 A1 | 1/2015 | Danby |
| 2015/0042254 A1 | 2/2015 | Kato |
| 2015/0082562 A1 | 3/2015 | Kamada |
| 2015/0098184 A1 | 4/2015 | Tsai et al. |
| 2015/0119771 A1 | 4/2015 | Roberts |
| 2015/0133833 A1 | 5/2015 | Bradley et al. |
| 2015/0145297 A1 | 5/2015 | Lee |
| 2015/0148592 A1 | 5/2015 | Kanbar |
| 2015/0157528 A1 | 6/2015 | Le et al. |
| 2015/0176674 A1 | 6/2015 | Khan et al. |
| 2015/0216719 A1* | 8/2015 | DeBenedictis ........... A61F 7/00 607/108 |
| 2015/0257964 A1 | 9/2015 | Ajiki |
| 2015/0305969 A1 | 10/2015 | Giraud |
| 2015/0328081 A1 | 11/2015 | Goldenberg et al. |
| 2015/0375315 A1 | 12/2015 | Ukai |
| 2016/0000642 A1 | 1/2016 | Zipper |
| 2016/0017905 A1 | 1/2016 | Cascolan et al. |
| 2016/0030279 A1 | 2/2016 | Driscoll |
| 2016/0045661 A1 | 2/2016 | Gray et al. |
| 2016/0112841 A1 | 4/2016 | Holland |
| 2016/0113840 A1 | 4/2016 | Crunick et al. |
| 2016/0113841 A1 | 4/2016 | Godfrey et al. |
| 2016/0127129 A1 | 5/2016 | Chee et al. |
| 2016/0129186 A1 | 5/2016 | Douglas et al. |
| 2016/0136037 A1 | 5/2016 | Cai |
| 2016/0136040 A1 | 5/2016 | Li |
| 2016/0166464 A1 | 6/2016 | Douglas et al. |
| 2016/0170996 A1 | 6/2016 | Frank et al. |
| 2016/0192814 A1 | 7/2016 | Kang et al. |
| 2016/0206502 A1 | 7/2016 | Køltzow |
| 2016/0243359 A1 | 8/2016 | Sharma |
| 2016/0263732 A1 | 9/2016 | Lourenco et al. |
| 2016/0269486 A1 | 9/2016 | Gupta et al. |
| 2016/0310353 A1 | 10/2016 | Barasch |
| 2016/0311091 A1 | 10/2016 | Wang |
| 2016/0324717 A1 | 11/2016 | Burton |
| 2016/0338901 A1 | 11/2016 | Cohen |
| 2016/0346163 A1 | 12/2016 | Konik |
| 2016/0367425 A1 | 12/2016 | Wersland |
| 2017/0027798 A1 | 2/2017 | Wersland |
| 2017/0042754 A1 | 2/2017 | Fowers et al. |
| 2017/0049278 A1 | 2/2017 | Thomassen |
| 2017/0069191 A1 | 3/2017 | Erkkila |
| 2017/0119623 A1 | 5/2017 | Attarian |
| 2017/0128320 A1 | 5/2017 | Chen |
| 2017/0156974 A1 | 6/2017 | Griner |
| 2017/0156975 A1 | 6/2017 | Mills |
| 2017/0189227 A1 | 7/2017 | Brunson |
| 2017/0216136 A1 | 8/2017 | Gordon |
| 2017/0233063 A1 | 8/2017 | Zhao et al. |
| 2017/0246074 A1 | 8/2017 | Wu |
| 2017/0304144 A1* | 10/2017 | Tucker .................. A61H 7/005 |
| 2017/0304145 A1 | 10/2017 | Pepe |
| 2017/0312161 A1 | 11/2017 | Johnson et al. |
| 2017/0360641 A1 | 12/2017 | Nakata et al. |
| 2018/0008512 A1* | 1/2018 | Goldstein .......... A61H 23/0263 |
| 2018/0050440 A1 | 2/2018 | Chen |
| 2018/0078449 A1 | 3/2018 | Callow |
| 2018/0133101 A1 | 5/2018 | Inada |
| 2018/0140100 A1 | 5/2018 | Cribbs |
| 2018/0140502 A1 | 5/2018 | Shahoian et al. |
| 2018/0141188 A1 | 5/2018 | Lai |
| 2018/0154141 A1 | 6/2018 | Ahn |
| 2018/0185234 A1 | 7/2018 | Ishiguro et al. |
| 2018/0200141 A1 | 7/2018 | Wersland |
| 2018/0236572 A1 | 8/2018 | Ukai |
| 2018/0243158 A1 | 8/2018 | Loghmani |
| 2018/0263845 A1 | 9/2018 | Wersland et al. |
| 2018/0279843 A1 | 10/2018 | Paul |
| 2018/0288160 A1 | 10/2018 | Paul et al. |
| 2018/0296433 A1 | 10/2018 | Danby |
| 2018/0315499 A1 | 11/2018 | Appelbaum et al. |
| 2018/0315504 A1 | 11/2018 | Inada et al. |
| 2019/0000709 A1 | 1/2019 | Sone et al. |
| 2019/0038229 A1 | 2/2019 | Perraut |
| 2019/0066833 A1 | 2/2019 | Wicki |
| 2019/0110945 A1 | 4/2019 | Kawagoe et al. |
| 2019/0175434 A1 | 6/2019 | Zhang |
| 2019/0209424 A1 | 7/2019 | Wersland et al. |
| 2019/0216677 A1 | 7/2019 | Paul |
| 2019/0232478 A1 | 8/2019 | Zawisza et al. |
| 2019/0254921 A1* | 8/2019 | Marton ............. A61H 23/0254 |
| 2019/0254922 A1 | 8/2019 | Marton et al. |
| 2019/0314239 A1 | 10/2019 | Ci |
| 2019/0337140 A1 | 11/2019 | Shanklin |
| 2019/0350793 A1 | 11/2019 | Wersland et al. |
| 2019/0381271 A1 | 12/2019 | Jo |
| 2020/0000237 A1 | 1/2020 | Wu |
| 2020/0009010 A1 | 1/2020 | Park et al. |
| 2020/0016027 A1 | 1/2020 | Kim et al. |
| 2020/0035237 A1 | 1/2020 | Kim et al. |
| 2020/0069510 A1 | 3/2020 | Wersland et al. |
| 2020/0085675 A1 | 3/2020 | Lee et al. |
| 2020/0090175 A1 | 3/2020 | Davis et al. |
| 2020/0179210 A1 | 6/2020 | Barragan Gomez |
| 2020/0179215 A1 | 6/2020 | Lerner |
| 2020/0230012 A1 | 7/2020 | Fuhr |
| 2020/0241683 A1 | 7/2020 | Le et al. |
| 2020/0261306 A1* | 8/2020 | Pepe ................... A61H 23/006 |
| 2020/0261307 A1 | 8/2020 | Wersland et al. |
| 2020/0268594 A1 | 8/2020 | Pepe |
| 2020/0294423 A1 | 9/2020 | Blain |
| 2020/0352821 A1 | 11/2020 | Wersland et al. |
| 2020/0390644 A1 | 12/2020 | Yang |
| 2020/0397651 A1 | 12/2020 | Park et al. |
| 2020/0405570 A1 | 12/2020 | Kodama |
| 2021/0000683 A1 | 1/2021 | Cheng |
| 2021/0022951 A1 | 1/2021 | Hu |
| 2021/0022955 A1 | 1/2021 | Wersland |
| 2021/0059898 A1 | 3/2021 | Wersland et al. |
| 2021/0085555 A1 | 3/2021 | Davis et al. |
| 2021/0128402 A1 | 5/2021 | Dai |
| 2021/0330539 A1 | 10/2021 | Faussett |
| 2022/0000781 A9 | 1/2022 | Leneweit et al. |
| 2022/0007810 A1 | 1/2022 | Paspatis et al. |
| 2022/0054350 A1 | 2/2022 | Merino et al. |
| 2022/0087433 A1 | 3/2022 | Mao et al. |
| 2022/0241135 A1 | 8/2022 | Wang |
| 2023/0001131 A1 | 1/2023 | English et al. |

FOREIGN PATENT DOCUMENTS

| | | |
|---|---|---|
| CN | 86101310 A | 9/1986 |
| CN | 1432452 A | 7/2003 |
| CN | 2788807 | 6/2006 |
| CN | 201239336 Y | 5/2009 |
| CN | 201239338 Y | 5/2009 |
| CN | 201333160 Y | 10/2009 |
| CN | 201524220 U | 7/2010 |
| CN | 101888050 A | 11/2010 |
| CN | 201743890 U | 2/2011 |
| CN | 201847899 U | 6/2011 |
| CN | 301664182 S | 9/2011 |
| CN | 202161539 U | 3/2012 |
| CN | 202637439 U | 1/2013 |
| CN | 103648320 A | 3/2014 |
| CN | 203598194 U | 5/2014 |
| CN | 205163583 U | 4/2016 |
| CN | 104352341 | 7/2016 |
| CN | 104352341 B | 7/2016 |
| CN | 205459750 U | 8/2016 |
| CN | 205494357 U | 8/2016 |
| CN | 205598186 U | 9/2016 |

(56) References Cited

FOREIGN PATENT DOCUMENTS

| | | |
|---|---|---|
| CN | 106074129 A | 11/2016 |
| CN | 106236528 A | 12/2016 |
| CN | 206081000 U | 4/2017 |
| CN | 106859949 A | 6/2017 |
| CN | 207286298 U | 5/2018 |
| CN | 108543126 A | 9/2018 |
| CN | 207855923 U | 9/2018 |
| CN | 109009978 A | 12/2018 |
| CN | 109259995 A | 1/2019 |
| CN | 208405314 U | 1/2019 |
| CN | 208448086 U | 2/2019 |
| CN | 109528473 A | 3/2019 |
| CN | 209154392 U | 7/2019 |
| CN | 110868983 A | 3/2020 |
| CN | 106618998 B | 8/2020 |
| CN | 111616938 A | 9/2020 |
| CN | 111973419 A | 11/2020 |
| CN | 113143721 A | 7/2021 |
| CN | 113509366 A | 10/2021 |
| DE | 3633888 A1 | 4/1988 |
| DE | 19905199 A1 | 7/2000 |
| DE | 102015102112 A1 | 8/2015 |
| DE | 202015005257 U1 | 10/2016 |
| EP | 0436719 B1 | 5/1994 |
| EP | 1728494 A1 | 12/2006 |
| EP | 2080500 A1 | 7/2009 |
| EP | 2328255 A1 | 6/2011 |
| EP | 1728494 B1 | 1/2013 |
| GB | 2066081 A | 7/1981 |
| GB | 2262236 A | 6/1993 |
| JP | S5230553 A | 3/1977 |
| JP | S5428491 A | 3/1979 |
| JP | 1990019157 | 1/1990 |
| JP | H03218763 A | 9/1991 |
| JP | H048128 B2 | 2/1992 |
| JP | H0447440 A | 2/1992 |
| JP | 1992047440 | 4/1992 |
| JP | H04-047440 U | 4/1992 |
| JP | H0447440 U | 4/1992 |
| JP | 1995051393 | 2/1995 |
| JP | 2000189525 A | 7/2000 |
| JP | 003077837 | 6/2001 |
| JP | 2002282322 A | 10/2002 |
| JP | 2003077837 A | 3/2003 |
| JP | 2005204777 | 4/2005 |
| JP | 2006034941 A | 2/2006 |
| JP | 2006212228 A | 8/2006 |
| JP | 2008510588 A | 4/2008 |
| JP | 2008289616 A | 12/2008 |
| JP | 2010534110 | 11/2010 |
| JP | 2011502369 A | 1/2011 |
| JP | 5129032 B2 | 1/2013 |
| JP | 2013119018 A | 6/2013 |
| JP | 2014511240 A | 5/2014 |
| JP | 2015035844 A | 2/2015 |
| JP | 2015104422 A | 6/2015 |
| JP | 2018518347 A | 7/2018 |
| KR | 200313149 Y1 | 5/2003 |
| KR | 200435552 Y1 | 1/2007 |
| KR | 100752432 B1 | 8/2007 |
| KR | 20090119424 A | 11/2009 |
| KR | 101123926 | 4/2012 |
| KR | 101162978 B1 | 7/2012 |
| KR | 101406275 | 6/2014 |
| KR | 20170106550 A | 9/2017 |
| KR | 20170108550 A | 9/2017 |
| KR | 20180031683 A | 3/2018 |
| KR | 20200051098 A * | 5/2020 |
| RU | 2170567 C1 | 7/2001 |
| TW | 1359657 B | 3/2012 |
| TW | 201440753 A | 8/2015 |
| WO | WO-0119316 A2 | 3/2001 |
| WO | 2009014727 | 1/2009 |
| WO | WO-2009102279 A1 | 8/2009 |
| WO | WO-2011159317 A1 | 12/2011 |
| WO | 2013114084 | 8/2013 |
| WO | WO-2013145346 A1 | 10/2013 |
| WO | 2014118596 | 8/2014 |
| WO | 2015038005 | 3/2015 |
| WO | WO-2018012105 A1 | 1/2018 |
| WO | WO-2019186225 A1 | 10/2019 |
| WO | WO-2021050861 A1 | 3/2021 |
| WO | WO-2023172676 A2 | 9/2023 |

OTHER PUBLICATIONS

TheraGun device in Archive.org webpage https://web.archive.org/web/20151218063848/http://www.theragun.com/#intro-1 Dec. 18, 2015 (archive date).
TheraGun G1 device in YouTube video "Theragun G1: Product Overview," https://www.youtube.com/watch?v=m9ilhfMGfZ8 Apr. 18, 2017 (upload date).
TheraGun G2Pro device in YouTube video "The Theragun G2PRO: Revolutionary Percussive Therapy," https://www.youtube.com/watch?v=2p9R6VA798o Oct. 10, 2017 (upload date).
PCT/US2016/038326 International Search Report & Written Opinion dated Sep. 1, 2016.
PCT/US2018/022426 International Search Report & Written Opinion dated May 31, 2018.
AU 2016284030 Examination Report dated May 7, 2018.
JP2018-517683 Office Action received Oct. 25, 2018.
CA 2990178 Office Action received Oct. 25, 2018.
WORX Trans4mer "Safety and Operating Manual Original Instructions" for 12V Li-Ion Multi-purpose saw, WX540, WX540.3, WX540.9, 2013.
Rachel [no family name indicated], "Jigsaw Massager", Apr. 18, 2010 (https://web.archive.org/web/20100418041422/http://www.instructables.com/id/Jigsaw-Massager/).
Rockwell Trans4mer Operating Manual for Multi-purpose saw, Model RK2516/RK2516K, 2011.
PCT/US2020/031936 International Search Report & Written Opinion dated Sep. 11, 2020.
International Search Report and Written Opinion issued in PCT/US20/50385 dated Dec. 3, 2020.
International Search Report and Written Opinion issued in PCT/US21/129900 dated Oct. 6, 2021.
Defendant's Initial Invalidity Contentions, *Therabody, Inc.* v. *Tzumi Electronics LLC et al.*, Case No. SDNY-1-21-CV-07803 (PGG)(RWL), dated Aug. 17, 2022; 16 pages.
Description of Therabody GI Device, available at: https://www.therabody.com/us/en-us/faq/theragun-devices/faq-devices-1.html?fdid=faq&csortb1=sortOrder&csortd1=1 (last visited Feb. 15, 2023).
Visual Description of Hyper Ice, Inc. Raptor Device, "RAPTOR Solutions 1.3 Prone," available at: https://www.youtube.com/watch?v=611tRqdwPU8&t=156s (last visited Feb. 15, 2023); 1 page.
Holly Riddle, "Theragun vs. Hyperice vs, Hydragun: Massage Gun Showdown (Buyer's Guide]," ChatterSource: Health & Wellness, Mar. 9, 2021, available at: https://www.chattersource.com/article/massage-gun/ (ast visited Feb. 17, 2023); 14 pages.
Anthony Katz, "The RAPTOR: Helps Patients and Saves Your Most Valuable Tool . . . Your Hands," DC Aligned: MeyerDC, Dec. 9, 2015, available at: http://news.meyerdc.com/community/vendor-spotlight/the-raptor-helps-patients-saves-your-most-valuable-tool-your-hands/ (last visited Feb. 15, 2023); 5 pages.
Visual Description of Hyper Ice, Inc. Raptor Device, "Osteopatia Haidy Ortale—Raptor Massage," available at: https://www.youtube.com/watch?v=plyW8FBowVs (last visited Feb. 15, 2023); 1 page.
Amazon: "OIVO Xbox One Controller Charger Dual Charging Station Updated Strap, Remote Charger Dock-2 Rechargeable Battery Packs Included," OIVO, Sep. 6, 2018, Especially annotated figures, Retrieved from Entire Document, 11 Pages.
Amazon: "PowerA Joy Con & Pro Controller Charging Dock Nintendo Switch," PowerA, Oct. 31, 2017, Especially annotated figures, Retrieved from Entire Document, 10 Pages.
Amazon: "Theragun G3PRO Percussive Therapy Device, White, Handheld Deep Muscle, Treatment Massager & Muscle Stimulator for Pain Relief, Recovery, Enhance Performance & Energize The

(56) References Cited

OTHER PUBLICATIONS

Body," Feb. 13, 2019, Shown on pp. 1, 2 p. Retrieved from URL: https://www.amazon.com/dp/B07MJ2MCT3/ref=nav_timeline_asin ?_ encoding=UTF8&psc=1.
Bardwell D., "Wahl's Massage Products—Meant for Life's Big Pains," DougBardwell.com, Apr. 6, 2016, 7 Pages, [Retrieved On Jun. 3, 2021] Retrieved from URL: https://dougbardwell.com/db/2016/04/06/wahls-massage-products-meant-for-lifes-big-pains/.
Collins D., "External Rotor Motor Basics: Design and Applications," Jun. 6, 2018, 03 Pages.
Collins D., "FAQ: What are Hall Effect Sensors and What Is Theirs Role In Dc Motors?," Jan. 11, 2017, 03 Pages.
Digi-Key's North American Editors: "How to Power and Control Brushless DC Motors," Dec. 7, 2016, 09 Pages.
Extended European Search Report for European Application No. 16815104.1, dated Jan. 23, 2019, 08 Pages.
Extended European Search Report for European Application No. 18832213.5, dated Jul. 21, 2021, 11 Pages.
Extended European Search Report for European Application No. 18832923.9, dated Apr. 23, 2021, 7 Pages.
Extended European Search Report for European Application No. 20720323.3, dated Sep. 9, 2021, 10 Pages.
Extended European Search Report for European Application No. 20802710.2, dated May 10, 2022, 9 Pages.
Extended European Search Report for European Application No. 20802804.3, dated Apr. 28, 2022, 8 Pages.
Extended European Search Report for European Application No. 21178300.6, dated Oct. 19, 2021, 9 Pages.
Extended European Search Report for European Application No. 21178311.3, dated Sep. 23, 2021, 5 Pages.
International Preliminary Report on Patentability for International Application No. PCT/US2016/038326, dated Jan. 4, 2018, 8 Pages.
International Preliminary Report on Patentability for International Application No. PCT/US2018/022426, dated Sep. 26, 2019, 9 Pages.
International Preliminary Report on Patentability for International Application No. PCT/US2018/039599, dated Jan. 23, 2020, 8 Pages.
International Preliminary Report on Patentability for International Application No. PCT/US2018/040795, dated Jan. 23, 2020, 7 Pages.
International Preliminary Report on Patentability for International Application No. PCT/US2019/067624, dated Jul. 8, 2021, 11 Pages.
International Preliminary Report on Patentability for International Application No. PCT/US2020/017645, dated Aug. 26, 2021, 11 Pages.
International Preliminary Report on Patentability for International Application No. PCT/US2020/031339, dated Nov. 18, 2021, 11 Pages.
International Preliminary Report on Patentability for International Application No. PCT/US2020/031936, dated Nov. 18, 2021, 14 Pages.
International Preliminary Report on Patentability for International Application No. PCT/US2020/050385, dated Mar. 24, 2022, 12 Pages.
International Preliminary Report on Patentability for International Application No. PCT/US2020/050399, dated Jan. 13, 2022, 6 Pages.
International Preliminary Report on Patentability for International Application No. PCT/US2020/054773, dated Apr. 21, 2022, 8 Pages.
International Preliminary Report on Patentability for International Application No. PCT/US2020/054842, dated Apr. 21, 2022, 7 Pages.
International Preliminary Report on Patentability for International Application No. PCT/US2020/063426, dated Jun. 16, 2022, 06 Pages.
International Preliminary Report on Patentability for International Application No. PCT/US2021/022500, dated Oct. 6, 2022, 6 Pages.
International Preliminary Report on Patentability for International Application No. PCT/US2021/029900, dated Nov. 10, 2022, 9 Pages.
International Preliminary Report on Patentability for International Application No. PCT/US2021/029903, dated Nov. 10, 2022, 7 Pages.
International Search Report and Written Opinion for International Application No. PCT/US2018/039599, dated Sep. 24, 2018, 9 Pages.
International Search Report and Written Opinion for International Application No. PCT/US2018/040795, dated Sep. 24, 2018, 8 Pages.
International Search Report and Written Opinion for International Application No. PCT/US2019/067624, dated Feb. 3, 2020, 13 Pages.
International Search Report and Written Opinion for International Application No. PCT/US2020/017645, dated May 20, 2020, 13 Pages.
International Search Report and Written Opinion for International Application No. PCT/US2020/031339, dated Jun. 10, 2020, 12 Pages.
International Search Report and Written Opinion for International Application No. PCT/US2020/031347, dated Aug. 3, 2020, 9 Pages.
International Search Report and Written Opinion for International Application No. PCT/US2020/050399, dated Feb. 4, 2021, 11 Pages.
International Search Report and Written Opinion for International Application No. PCT/US2020/054773, dated Jan. 12, 2021, 9 Pages.
International Search Report and Written Opinion for International Application No. PCT/US2020/054842, dated Jan. 11, 2021, 8 Pages.
International Search Report and Written Opinion for International Application No. PCT/US2020/063426, dated Feb. 26, 2021, 09 Pages.
International Search Report and Written Opinion for International Application No. PCT/US2021/022500, dated Apr. 20, 2021, 7 Pages.
International Search Report and Written Opinion for International Application No. PCT/US2021/029903, dated Jul. 28, 2021, 8 Pages.
International Search Report and Written Opinion for International Application No. PCT/US2022/028309, dated Sep. 8, 2022, 10 Pages.
International Search Report and Written Opinion for International Application No. PCT/US2022/076238, dated Jan. 23, 2023, 12 Pages.
Machine translation from Espacenet of written description and claims for CN106074129A, 9 pages (2016).
Machine translation from Espacenet of written description and claims for CN111616938A, 5 pages (2020).
Machine translation from Espacenet of written description and claims for CN111973419A, 7 pages (2020).
Machine Translation of Written Description and Claims for WO2013145346A1 (Year: 2013).
Massage Expert: "Nursal Deep Percussion Massager Review - 6 Interchangeable Nodes," Jan. 4, 2021, 6 Pages, [Retrieved on Jun. 3, 2021] Retrieved from URL: https://www.massageexpert.net/nursal-deep-percussion-massager-review/.
McFarland M., "Segway Was Supposed to Change the World, Two Decades Later, It Just Might," CNN Wire Service, Oct. 30, 2018, 7 Pages.
Partial Supplementary European Search Report for European Application No. 18832213.5, dated Apr. 20, 2021, 12 Pages.
Supplementary European Search Report for European Application No. 19904459.5, dated Apr. 15, 2021, 04 Pages.
TESTBERICHTE.DE: "Naipo Handheld Percussion Massager with Heating (MGPC 5000)," amazon.de, 7 Pages, [Retrieved on Jun. 3, 2021] Retrieved from URL: https://www.testberichte.de/p/naipo-tests/handheld-percussion-massager-with-heating-mgpc-5000-testbericht.html, See also a YouTube Review of this Device dated May 21, 2018 at https://www.youtube.com/watch?v=bi_QCJA3D9k.

(56) References Cited

OTHER PUBLICATIONS

WORX Trans4mer "Safety and Operating Manual Original Instructions" for 12V Li-Ion Multipurpose saw, WX540, NX540.3, WX540.9, 16 pages (2013).

Youtube: "Unboxing: Joy-Con & Pro Controller Charging Dock for Nintendo Switch," Crusherbad64, Especially demonstration 8:30-8:55, (This reference is Being Used to Show Greater Details of Product not Clearly Disclosed in 'PowerA'), Feb. 26, 2018, Retrieved from entire document, 1 Page.

Notice of First Examination Opinion directed to Chinese Patent Application No. 202180041926.3, dated Jul. 7, 2023; 16 pages.

\* cited by examiner

| | PROTOCOL 1 | | | |
|---|---|---|---|---|
| STEP | 1 | 2 | 3 | 4 |
| TIME(M) | 0:30 | 0:15 | 0:30 | 0:45 |
| SPEED (RPM) | 1550 | 2100 | 2200 | 2400 |
| AMPLITUDE | 2 | 3 | 1 | 4 |
| ATTACHMENT | DAMPENER | SMALL BALL | DAMPENER | LARGE BALL |
| FORCE | 1 | 3 | 3 | 2 |
| TEMPERATURE (°C) | 21 | 26 | 29 | 32 |
| GRIP | 1 | 1 | 1 | 1 |

*FIG. 24*

| PROTOCOL: SHIN SPLINTS | | | | |
|---|---|---|---|---|
| STEP | 1 | 2 | 3 | 4 |
| TIME(M) | 1:00 | 1:00 | 1:00 | 1:00 |
| SPEED (RPM) | 1500 | 1500 | 2000 | 2000 |
| AMPLITUDE | 1 | 1 | 3 | 3 |
| ATTACHMENT | DAMPENER | DAMPENER | DAMPENER | DAMPENER |
| FORCE | 2 | 2 | 3 | 3 |
| TEMPERATURE (°C) | 21 | 21 | 24 | 24 |
| GRIP | REVERSE | REVERSE | BASE | BASE |
| ARM POSITION | 1 | 1 | 1 | 1 |
| BODY PART | R. SHIN | L. SHIN | R. CALF | L. CALF |

FIG. 25

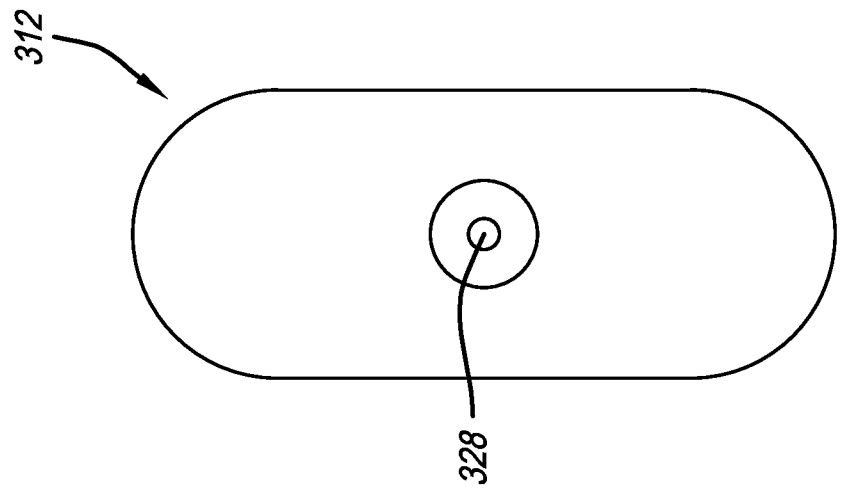
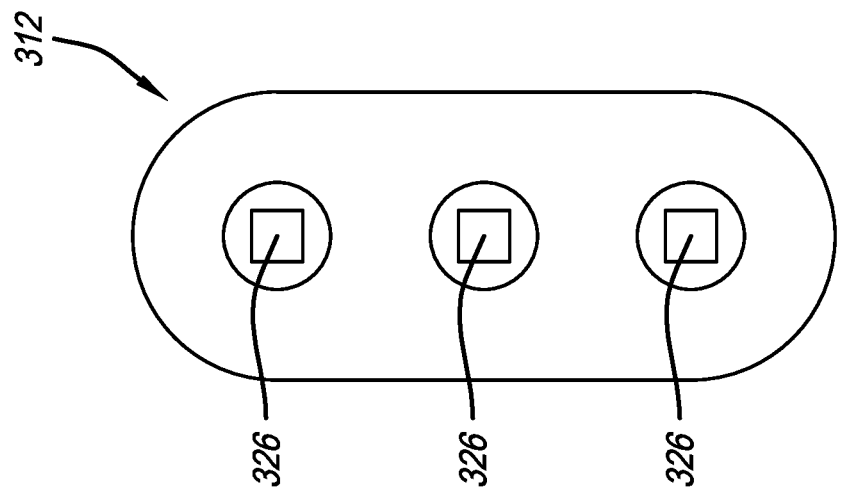
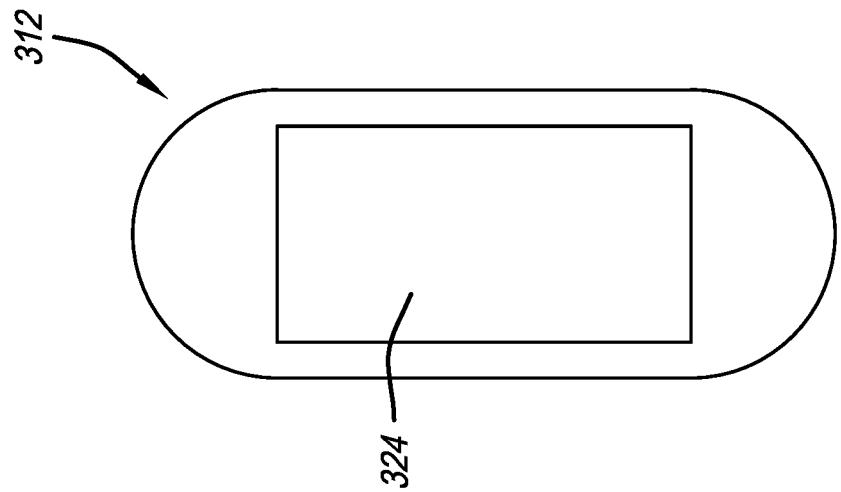

PERCUSSIVE THERAPY DEVICE WITH INTERCHANGEABLE MODULES

CROSS-REFERENCE TO RELATED APPLICATIONS

This application is a continuation-in-part of U.S. patent application Ser. No. 17/244,239, filed Apr. 29, 2021, which is a continuation-in-part of U.S. patent application Ser. No. 17/018,099, filed Sep. 11, 2020, which is a continuation-in-part of U.S. patent application Ser. No. 16/869,402, filed May 7, 2020, now U.S. Pat. No. 10,857,064, which is a continuation-in-part of U.S. patent application Ser. No. 16/796,143, filed Feb. 20, 2020, now U.S. Pat. No. 10,940,081, which claims the benefit of U.S. Provisional Application No. 62/844,424, filed May 7, 2019, U.S. Provisional Application No. 62/899,098, filed Sep. 11, 2019 and U.S. Provisional Application No. 62/912,392, filed Oct. 8, 2019. U.S. patent application Ser. No. 16/869,402 is also a continuation-in-part of U.S. patent application Ser. No. 16/675,772, filed Nov. 6, 2019, now U.S. Pat. No. 10,702,448, which claims the benefit of U.S. Provisional Application No. 62/785,151, filed on Dec. 26, 2018. U.S. patent application Ser. No. 17/244,239 also claims the benefit of U.S. Provisional Application No. 63/133,951, filed Jan. 5, 2021 and U.S. Provisional Application No. 63/017,472, filed Apr. 29, 2020. This application is also a continuation-in-part of U.S. patent application Ser. No. 17/705,300, filed Mar. 26, 2022, which is a continuation-in-part of U.S. patent application Ser. No. 17/361,966, filed Jun. 29, 2021, which claims the benefit of U.S. Provisional Application No. 63/133,530, filed Jan. 4, 2021, U.S. Provisional Application No. 63/065,348, filed Aug. 13, 2020, and U.S. Provisional Patent Application No. 63/045,365, filed Jun. 29, 2020. This application also claims the benefit of U.S. Provisional Application No. 63/185,927, filed May 7, 2021. All applications listed above are incorporated by reference herein in their entireties.

FIELD OF THE INVENTION

The present invention relates generally to massage devices and more particularly to a percussive therapy device that includes interchangeable modules.

BACKGROUND OF THE INVENTION

Percussive massage devices are known for providing percussive therapy. However, a percussive massage or therapy device that also includes the ability to include other technologies that are interchangeable may be beneficial.

SUMMARY OF THE PREFERRED EMBODIMENTS

In accordance with a first aspect of the present invention there is provided a percussive therapy device includes a housing, an electrical source, a motor positioned in the housing, a switch for activating the motor, and a push rod assembly operatively connected to the motor and configured to reciprocate in response to activation of the motor. A massage attachment is removably received on a distal end of the push rod assembly at a first location. The percussive therapy device also includes an attachment module associated with the housing of the percussive therapy device at a second location. The second location is different than the first location. The attachment module is configured to provide an active effect. In a preferred embodiment, the attachment module is connected to and removable from the housing of the percussive therapy device. In another preferred embodiment, the attachment module is not configure to be removable from the housing by a user of the percussive therapy device.

The active effect can be one or more of cold therapy, heat therapy, LED light therapy, photobiomodulation therapy, obtaining biometric data of the user, angular position data of the percussive therapy device, and linear position data of the percussive therapy device. In a preferred embodiment, the housing includes a first electrical connector and the attachment module includes a second electrical connector in electrical communication with the first electrical connector. Connection of the first and second electrical connectors provides electrical communication between the electrical source and the attachment module. Connection of the first and second electrical connectors may also provide data communication between the percussive therapy device and the attachment module.

In a preferred embodiment, at least a portion of the attachment module surrounds at least a portion of the push rod assembly. In a preferred embodiment, the attachment module includes a central opening, and at least a portion of the push rod assembly is configured to reciprocate within and relative to the attachment module. Preferably, the attachment module is connected to and removable from the housing of the percussive therapy device at the same time the massage attachment is received on the distal end of the push rod assembly. However, the attachment module can also be used or connected to the housing when the massage attachment is not connected to the distal end of the push rod assembly.

In accordance with another aspect of the present invention there is provided a method of using a percussive therapy device that includes obtaining the percussive therapy device, placing a removable massage attachment on a distal end of the push rod assembly at a first location, securing an attachment module to the housing of the percussive therapy device at a second location, where the first location is different than the second location, operating the percussive therapy device to reciprocate the massage attachment, massaging a body part of the user using the massage attachment, and using the attachment module to provide an active effect to one of the first body part or a second body part of the user.

In accordance with another aspect of the present invention there is provided a percussive therapy device that includes a housing, an electrical source, a motor positioned in the housing, a switch for activating the motor, a push rod assembly operatively connected to the motor and configured to reciprocate in response to activation of the motor, and at least one of an angular position sensor configured to obtain angular position data of the percussive therapy device and a linear position sensor configured to obtain linear position data of the percussive therapy device.

In a preferred embodiment, the device includes an attachment module configured to be operatively connected to the percussive therapy device and including the at least one of an angular position sensor and the linear position sensor. Preferably, the angular position sensor is configured to sense variations in angular position of the percussive therapy device in accordance with three axes of rotation. Preferably, the linear position sensor is configured to sense movement of the percussive therapy device in accordance with three linear axes. The device may be configured to transmit at least one of the angular position data and the linear position data to a remote device. In an embodiment, a graphical representation of the at least one of the angular position data and the linear position data is generated. Preferably, the device is configured to receive at least one protocol configured to provide at least one therapeutic effect.

In a preferred embodiment, the device includes a portion of the housing that surrounds at least a portion of the push rod assembly. The attachment module may be configured to be operatively connected to the portion of the housing surrounding the push rod assembly. The attachment module may include a wireless connection module configured to transmit to and receive data from the percussive therapy device or a remote device.

In accordance with another aspect of the present invention there is provided a method of providing at least one therapeutic effect to a user that includes obtaining a percussive therapy device including a housing, an electrical source, a motor positioned in the housing, a switch for activating the motor, a push rod assembly operatively connected to the motor and configured to reciprocate in response to activation of the motor, operating the percussive therapy device to provide the at least one therapeutic effect to the user, obtaining at least one of angular position data in accordance with three axes of rotation and linear position data in accordance with three linear axes, and recommending an adjustment to at least one of an angular position and a linear position of the percussive massage device in response to at least one of the angular position data and the linear position data. The method can also include obtaining an attachment module configured to be operatively connected to the percussive therapy device.

In a preferred embodiment, the method includes obtaining force magnitude data to determine a magnitude of force an attachment of the percussive therapy device is exerting on the user, and recommending an adjustment to a force magnitude of the percussive therapy device in response to the force magnitude data. The method can include determining whether the attachment of the percussive therapy device is in contact with the user.

In accordance with another aspect of the present invention there is provided a percussive therapy device that includes a housing, an electrical source, a motor positioned in the housing, a switch for activating the motor, a push rod assembly operatively connected to the motor and configured to reciprocate in response to activation of the motor, a gyroscope configured to obtain angular position data of the percussive therapy device, an accelerometer configured to obtain linear position data of the percussive therapy device, a force meter configured to obtain force magnitude data proportional to a force an attachment of the percussive therapy device is exerting on the user, and at least one remote device configured to receive the angular position data, the linear position data, and the force magnitude data. The device may include an attachment module comprising at least one of the gyroscope and the accelerometer.

In a preferred embodiment, a recommendation is provided to the user to adjust at least one of an angular position of the percussive therapy device, a linear position of the percussive therapy device, and a force magnitude of the percussive therapy device in response to at least one of the angular position data, the linear position data, and the force magnitude data. The recommendation may be provided to the user via the at least one remote device.

In accordance with another aspect of the present invention there is provided an attachment module configured to be operably connected with a percussive therapy device that includes a housing, a wireless connection module, and at least one sensor configured to obtain at least one of biometric data of the user and information regarding operation of the percussive therapy device. The sensor may be a thermal sensor configured to obtain a temperature reading of a first body part of the user. In a preferred embodiment, the housing includes a securement portion that is configured to secure the attachment module to an outside of a housing of the percussive therapy device. Preferably, the sensor includes at least one of a force meter, a gyroscope, and an accelerometer.

In a preferred embodiment, the wireless connection module is configured to transmit to and receive data from at least one of the percussive therapy device and a remote device.

In a preferred embodiment, the sensor is a thermal sensor configured to obtain a temperature reading of a first body part of the user, and the attachment module includes a gyroscope configured to obtain angular position data of the attachment module, and an accelerometer configured to obtain linear position data of the attachment module.

In a preferred embodiment, the present invention is embodied in a percussive massage device that includes a removable module that may be installed or positioned in the bottom portion, belly or third handle portion of the device. The module is received in a modular space defined in the housing and in the interior of the third handle portion.

Different modules have or include different capabilities or technologies and include different components, as described herein, and can be used as desired by the user.

In a preferred embodiment, different interchangeable attachment modules can be used to provide therapeutic benefits to the user or can be used to gather health data from the user. For example, a module can include sensors or other technology that are capable of recognition of the passive foam attachments on the distal end of the reciprocating shaft (e.g., dampener, cone, ball, etc.), providing heating or cooling, far infrared therapy, muscle temperature determination, oximeter, heartrate sensor, electric muscle stimulation, bloodflow sensor, blood pressure sensor, an eye motion sensor, a microphone, an electroencephalogram sensor, a muscle activity sensor, an electrocardiography sensor, a photoplethysmography sensor, a pressure sensor, and a touch sensor, etc. The module can also include features such as a gyroscope for determining angular movement of the device and/or an accelerometer for determining linear movement of the device. One or more of any of these technologies can be included in an attachment module.

In a preferred embodiment, the module is secured in place with one or more magnets and it is electrically and data connected and communicated to the main PCB of the device. Preferably, the device recognizes the type of module that has been installed and triggers the different protocols and functionalities associated with the attached module, for example red light therapy. In a preferred embodiment, the gathered data can be used to turn the percussive massage device into a telemedicine type product, thereby allowing a medical professional to determine any issues or diagnose the user of the device or for a computer or the like to recognize any issues or anomalies and provide a notification to the user, their doctor or other entity or organization.

In an exemplary embodiment, the percussive massage device includes a far infrared module thereon. The far infrared module is configured to emit far infrared radiation that provides therapy to a user's skin and muscles. For example, infrared light therapy has been known to improve blood circulation and skin complexion; expand capillaries, which stimulates increased blood flow, regeneration, circulation and oxygen; strengthen the cardiovascular system; improve detoxification; stimulate wound healing, relaxation and pain/aches management; boost immunity and provide cancer support. It should be appreciated that the infrared light therapy is different than using infrared for determining temperature. Those of ordinary skill in the art would understand that the wavelengths are different for determining temperature and providing therapy. Far-infrared radiation is found on the wavelength spectrum at 15-1000 μm. Typically, only IR wavelengths between 0.7 μm and 20 μm are used for temperature measurement. Furthermore, temperature measurement only uses a beam. Whereas the far infrared therapy described herein directs the light over a larger area of a user's skin.

Thus, the description herein referencing gyroscopes, accelerometers, attachments, male or female attachment members, or sensors or actuators within or without the housing is instructive and within the scope of the attachment. For example, a heating element may be implemented in the attachment to utilize far infrared radiation to penetrate skin and muscle to a certain depth. This treatment can result in muscle recovery. The heating element may be, for example, a peltier device and related technology.

It will be appreciated that any of the technologies or features discussed herein that can be included in a removable module can also be included permanently within the device. For example, a far infrared panel may be disposed on or in a bottom surface of the bottom or third handle portion of the housing such that it can direct the light emitted from the infrared lights (e.g., LED or the like) into or near the path of the percussive massage attachment of the device. There may be some overlap between the area (of the user's skin) contacted by the attachment and the area on which the light emitted from the panel shines. This allows the infrared light to shine on or contact the area that the attachment contacts, when the attachment is on its upstroke during reciprocation.

BRIEF DESCRIPTION OF THE DRAWINGS

The invention may be more readily understood by referring to the accompanying drawings in which:

FIG. 24 is a chart showing steps of Protocol 1 in accordance with a method of performing a routine for a percussive massage device;

FIG. 25 is a chart showing steps of a "Shin Splints" protocol in accordance with a method of performing a routine for a percussive massage device;

FIG. 52A shows an attachment module with heat therapy as an active effect;

FIG. 52B shows an attachment module with LED light therapy as an active effect;

FIG. 52C shows an attachment module with temperature sensing as an active effect;

Like numerals refer to like parts throughout the several views of the drawings.

DETAILED DESCRIPTION OF THE PREFERRED EMBODIMENTS

Figure 1:
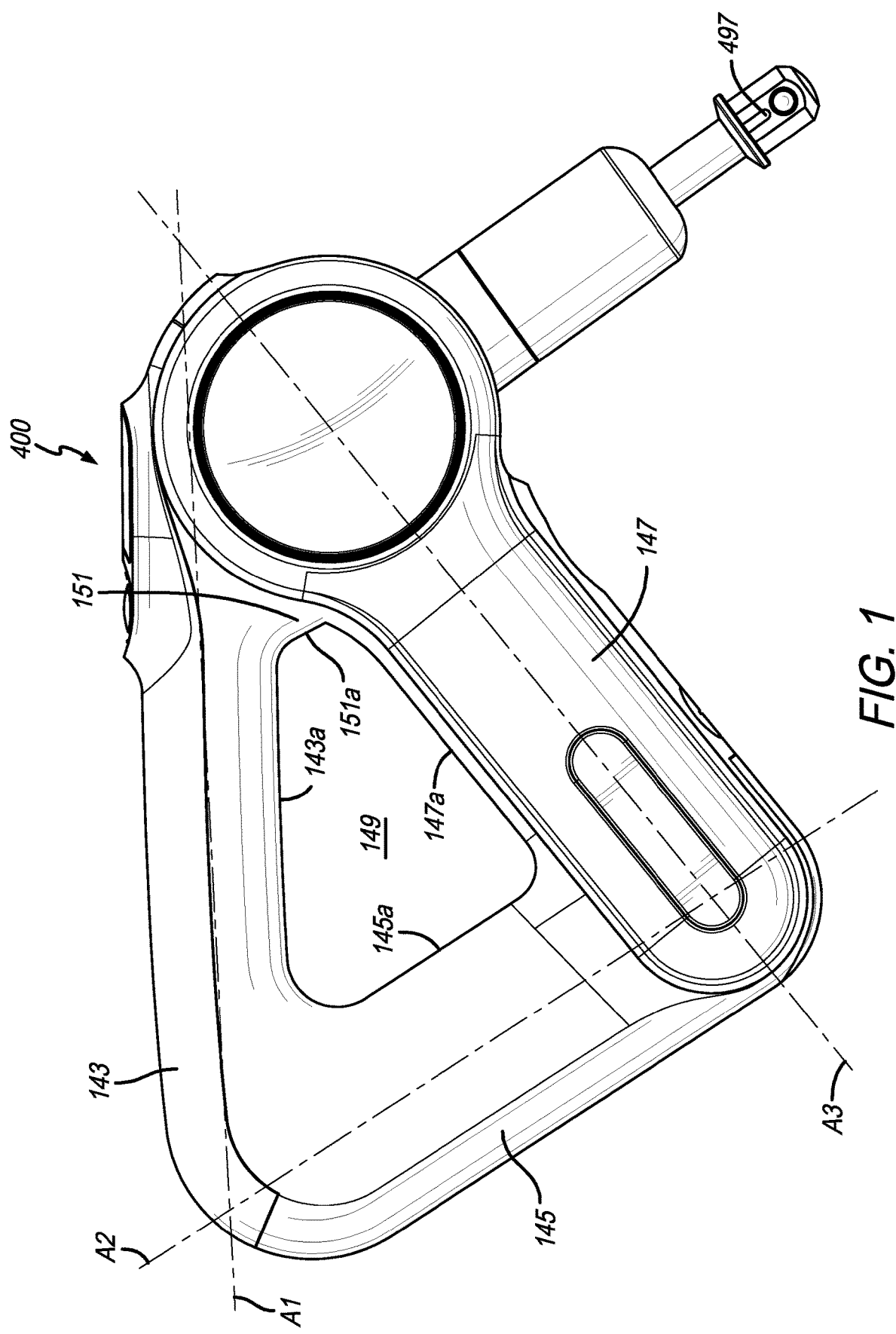
FIG. 1 is a side elevational view of a percussive massage device in accordance with a preferred embodiment of the present invention.

The following description and drawings are illustrative and are not to be construed as limiting. Numerous specific details are described to provide a thorough understanding of the disclosure. However, in certain instances, well-known or conventional details are not described in order to avoid obscuring the description. References to one or another embodiment in the present disclosure can be, but not necessarily are, references to the same embodiment; and, such references mean at least one of the embodiments.

Reference in this specification to "one embodiment" or "an embodiment" means that a particular feature, structure, or characteristic described in connection with the embodiment is included in at least one embodiment of the disclosure. Appearances of the phrase "in one embodiment" in various places in the specification do not necessarily refer to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," and "below" used herein are merely for ease of description and refer to the orientation of the components as shown in the figures. It should be understood that any orientation of the components described herein is within the scope of the present invention.

While many embodiments are described herein, at least some of the described embodiments provide an apparatus, system, and method for a reciprocating treatment device.

Figure 19:
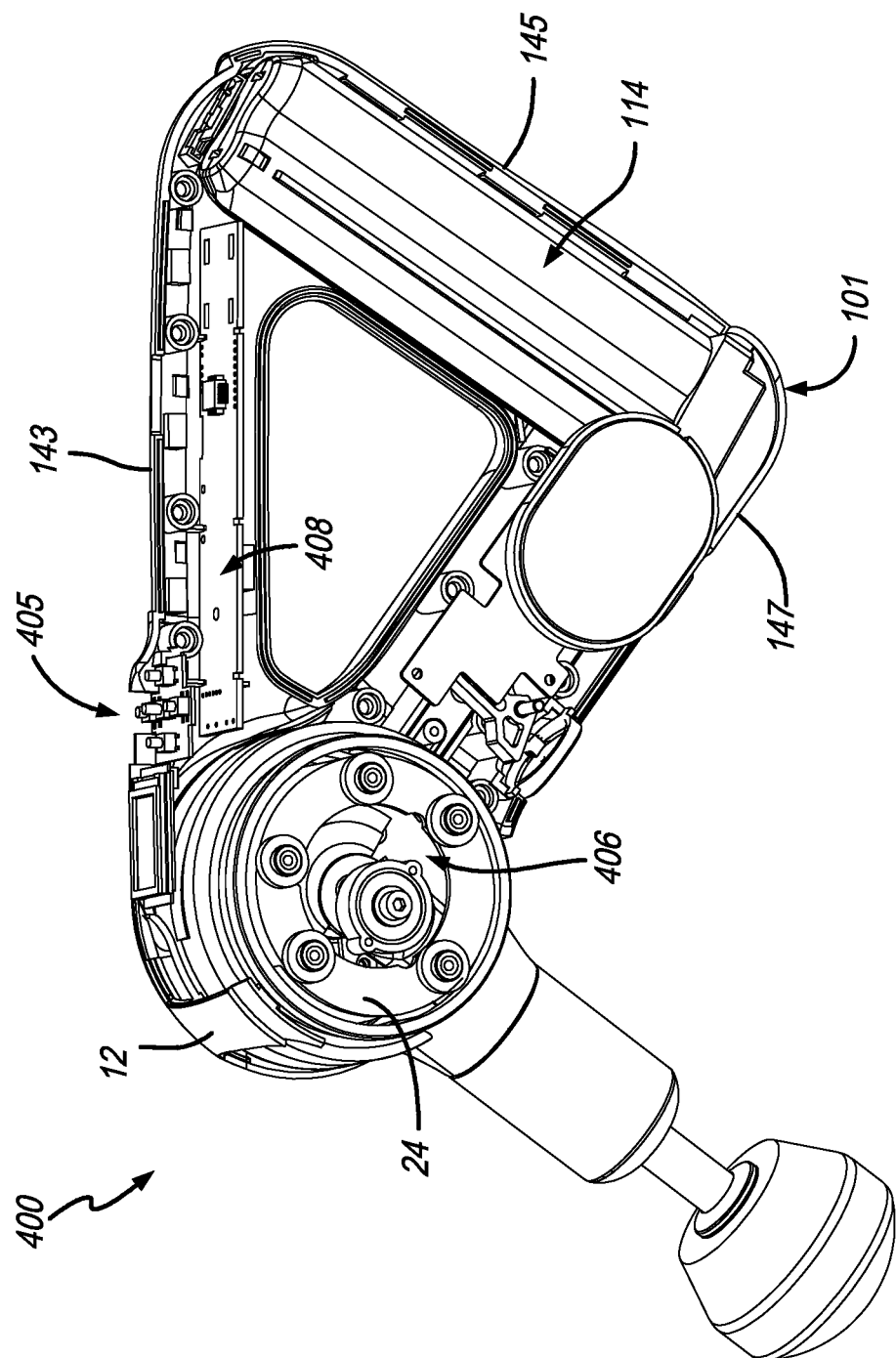
FIG. 19 is a perspective view of the percussive massage device with a portion of the housing removed.

FIG. 1 shows an embodiment of a percussive massage device 400 that includes a rechargeable battery (and replaceable or removable battery) 114 (FIG. 19). As shown in FIG. 1, in a preferred embodiment, the percussive massage device 400 includes three handle portions (referred to herein as first handle portion 143, second handle portion 145 and third handle portion 147) that cooperate to define a central or handle opening 149. All of the handle portions are long enough that they are configured such that a person can grasp that particular handle portion to utilize the device. The ability to grasp the different handle portions allows a person (when using the device on their own body) to use the device on different body parts and from different angles, thus providing the ability to reach body parts, such as the back, that might not be possible without the three handle portions.

As shown in FIG. 1, the first handle portion 143 defines a first handle portion axis A1, the second handle portion 145 defines a second handle portion axis A2 and the third handle portion 147 defines a third handle portion axis A3 that cooperate to form a triangle. In a preferred embodiment, the battery 114 is housed in the second handle portion 145 and the motor 406 (FIG. 19) is housed in the third handle portion 147.

In a preferred embodiment, the first handle portion 143 has an interior edge 143a, the second handle portion 145 has an interior edge 145a and the third handle portion 147 has an interior edge 147a, which all cooperate to at least partially define the handle opening 149. As shown in FIG. 1, in a preferred embodiment, the first handle portion 143 includes a finger protrusion 151 that includes a finger surface 151a or fourth interior surface that extends between the interior edge 143a of the first handle portion and the interior edge 147a of the third handle portion 147 and at least partially defines the handle opening 149. In use, a user can place their index finger against the finger surface 151a. The finger protrusion and surface provide a feedback point or support surface such that when a user places their index finger against the surface it helps the user with control and comfort of using the device. In a preferred embodiment, at least a portion of the finger surface 151a is straight, as shown in FIG. 1 (as opposed to the other "corners" of the handle opening 149 being rounded).

As shown in FIG. 1, with the finger surface 151a being straight, the first handle portion interior surface, second handle portion interior surface, third handle portion interior surface and finger surface cooperate to define a quadrilateral with radii or rounded edges between each of the straight surfaces.

Figure 2:
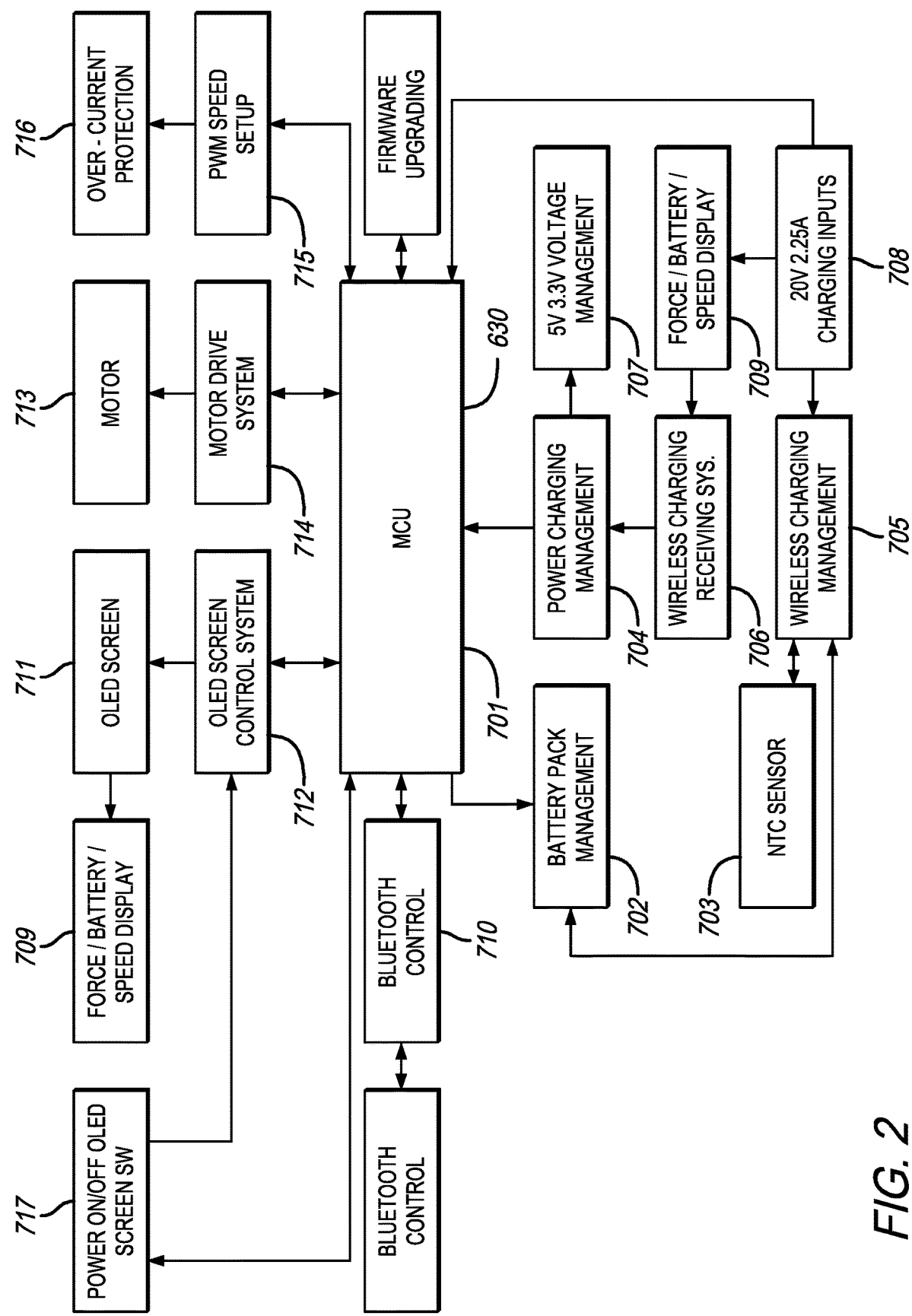
FIG. 2 is a block diagram showing interconnected components of a percussive massage device with a force meter.

FIGS. 2-20 show embodiments in accordance with a percussion massage device with a force meter. FIG. 2 is a block diagram showing interconnected components of a percussive therapy device with a force meter 400. In an embodiment, the percussive therapy device with force meter 400 includes a microcontroller unit 701, a battery pack management unit 702, an NTC sensor 703, a power charging management unit 704, a wireless charging management unit 705, a wireless charging receiving system 706, a voltage management unit 707 (5V 3.3V Voltage Management in drawings), battery charging inputs 708 (20V 2.25A Charging Inputs in drawings), a display 709 (Force/Battery/Speed Display in drawings), a wireless control unit 710 (Bluetooth Control in drawings), an OLED screen 711, an OLED screen control system 712, a motor 713, a motor drive system 714, a PWM speed setup unit 715, an over-current protection unit 716, and a power switch unit 717 (Power On/Off OLED Screen SW in drawings). In the embodiment shown in accordance with FIG. 2, each block in the diagram is shown as a separate component. In alternative embodiments, however, certain components may be combined without departing from the scope of the present disclosure.

The microcontroller unit 701, in an embodiment, is a microcontroller unit including a processor, a memory, and input/output peripherals. In other embodiments, however the microcontroller unit 701 is an ST Microelectronics STM32F030K6 series of microcontroller units, STM32F030C8T6 series of microcontrollers, STM32F030CCT6 series of microcontrollers, or an equivalent microcontroller.

One of ordinary skill would understand that the memory of the microcontroller unit 701 is configured to store machine-readable code for processing by the processor of the microcontroller unit 701. Various other configurations may exist depending on whether the designer of the percussive massage device with force meter 400 desires to implement the machine-readable code in software, firmware, or both. In an embodiment, the machine-readable code is stored on the memory and configured to be executed by a processor of the microcontroller 701. In an embodiment, the machine-readable code is stored on computer-readable media.

The battery pack management unit 702, in an embodiment, is implemented in firmware or software and configured to be used in connection with the microcontroller unit 701. In this embodiment, the firmware or software is stored in memory (not shown) and configured to be obtainable by the microcontroller unit 701. The battery pack management unit 702 may also be a combination of firmware, software, and hardware, in another embodiment. The battery pack management unit 702 is coupled with the NTC sensor 703. The NTC sensor 703 is a negative temperature coefficient thermistor used by the battery pack management unit 702 to sense temperature of the battery pack. For example, the NTC sensor 703 is a thermistor with B value of 3950+/−1%, and a resistance of 10 kn. In another example, the thermistor has a resistance of 100 kn. One of ordinary skill in the art would recognize that a thermistor is a resistor whose resistance is dependent upon temperature. In other embodiments, however, the NTC sensor 703 may be another type of temperature sensing device or component used in connection with the battery pack management unit 702.

The power charging management unit 704, in an embodiment, is implemented in firmware or software and configured to be used in connection with the microcontroller unit 701. Similarly to the battery pack management unit 702, the power charging management unit 704 firmware or software is stored in memory (not shown) and configured to be obtainable by the microcontroller unit 701. The power charging management unit 704 may also be a combination of firmware, software, and hardware, in another embodiment. In various embodiments, the power charging management unit 704 is configured to charge a battery pack via a direct connection or through an external charger, such as when configured to be operable with rechargeable batteries.

The wireless charging management unit 705, in an embodiment, is coupled to the battery pack management unit 702 and the battery charging inputs 708. In other embodiments, the battery or battery pack is charged using other conventional methodologies, such as, for example, charging the battery or battery pack using a wire or cord coupled to the battery charging inputs 708.

The wireless charging receiving system 706, in an embodiment, is coupled to the power charging management unit 704 and the display 709. The wireless charging receiving system 706 includes one or more of firmware, software, and hardware. In an embodiment, the wireless charging receiving system 706 is configured to receive information pertaining to battery capacity, charging metrics, and other information pertaining to wireless charging, and to pass along the information to the power charging management unit 704. The wireless charging receiving system 706 preferably includes a wireless charging pad used to charge the percussive massage device with force meter 400. One of ordinary skill in the art would understand that a variety of wireless charging devices may be utilized to wirelessly charge the percussive massage device with force meter 400. As one example, the Qi wireless charging standard and related devices may be utilized to wirelessly charge the percussive massage device with force meter 400.

The voltage management unit 707, in an embodiment, is a DC voltage regulator that steps down 5 volt to 3.3 volt power for use by the microcontroller unit 701. The voltage management unit 707 may also perform additional functions for management of 3.3 volt power for use by the microcontroller unit 701. In an embodiment, the voltage management unit 707 is implemented using a series of electronic components such as, for example, implementing a resistive divider using electronic components. In another embodiment, the voltage management unit 707 is a stand-alone voltage regulator module and/or device designed to step down voltage from 5 volts to 3.3 volts. One of ordinary skill in the art would understand the various methodologies and devices available to step down 5 volts to 3.3 volts.

The battery charging inputs 708, in an embodiment, are interfaces by which a wire or cord may be inserted for charging the percussive massage device with force meter 400. For example, a standardized barrel connector is the battery charging inputs 708. In another example, the battery charging inputs 708 is a USB connector. Other more specialized charging methodologies may require a particular battery charging input not described above.

The display 709, in an embodiment, displays a series of LEDs depicting an amount of force applied by the percussive massage device with force meter 400. In an alternative embodiment, the display 709 displays a series of LEDs depicting the current battery or battery pack charge of the percussive massage device with force meter 400. In yet another embodiment, the display 709 displays a series of LEDs depicting the current speed of the percussive massage device with force meter 400. One of ordinary skill in the art would recognize that while LEDs have been specified in the above-referenced embodiments, other embodiments not using LEDs are within the scope of this disclosure, such as, for example, liquid crystal displays, OLEDs, CRT displays, or plasma displays. One of ordinary skill in the art would also understand that it may be advantageous in an embodiment utilizing a battery or battery pack to use low-power options to ensure battery power longevity. In an embodiment, the display 709 is a 128×64 pixel OLED display.

The wireless control unit 710 is a wireless connectivity device that may be implemented in a wireless microcontroller unit. In an embodiment, the wireless control unit 710 is a Bluetooth transceiver module configured to couple, via Bluetooth, to a remote device. In an embodiment, the Bluetooth module is a Bluetooth Low-Energy (BLE) module configured to be run in broadcast mode. The wireless control unit 710 is coupled to the microcontroller unit 701. In an embodiment, the remote device is a smartphone having an embedded Bluetooth module. In an alternative embodiment, the remote device is a personal computer having Bluetooth connectivity. In other embodiments, other wireless connectivity standards besides the Bluetooth wireless standard may be utilized. It will be appreciated that the Bluetooth connectivity or other wireless connectivity may be described herein as being implemented in a wireless connection device. The wireless connection device can be a separate module, can be included in the MCU or other component of the device, or can be a separate chip. In summary, the percussive therapy device including a wireless connection device means that the percussive massage device can connect to another electronic device wirelessly (e.g., a phone, tablet, computer, computer, voice controlled speaker, regular speaker, etc.). One of ordinary skill in the art would recognize that low-power wireless control modules may be advantageous when the percussive massage device with force meter 400 is utilizing a battery or battery pack.

The OLED screen 711 and the OLED screen control system 712, in an embodiment, are configured to display substantially the same information as the display 709 referenced above. The OLED screen 711 is coupled to the OLED screen control system 511. The OLED screen control system 712 is coupled to the microcontroller unit 701, the OLED screen 711, and the power switch unit 717. In an embodiment, the display 709 and the OLED screen 711 may be redundant and it may only be necessary to utilize one or the other.

The motor 713, in an embodiment, is a brushless direct current (BLDC) motor. The motor 713 and the motor drive system 714, in an embodiment, are configured to vary the speed (i.e., rotational motion) that may be converted to reciprocal motion. In other embodiments, the motor 713 is a brushed DC motor, a brushed AC motor, or a brushless AC motor. One of ordinary skill in the art would understand that choosing a brushless or brushed motor, or direct current or alternating current, may vary depending on the application and intended size, battery power, and use.

The PWM speed setup unit 715, in an embodiment, is used to control pulse width modulation utilized to drive the motor 713. The PWM speed setup unit 715 is coupled to the microcontroller unit 701 and the over-current protection unit 716. One of ordinary skill in the art would understand that pulse width modulation is one way to vary the average power applied to the motor 713, resulting in varying speed as desired. In alternative embodiments, one of ordinary skill in the art would understand that there are a variety of methods to vary the speed of a brushless DC motor. For example, voltage to the motor 713 may be controlled in other non-PWM methods.

The over-current protection unit 716, in an embodiment, may be a feature of an integrated system-in-package to prevent damage caused by high currents to the motor. In other embodiments, the over-current protection unit 716 is implemented using a series of electronic components configured to protect the motor from excessively high current.

The power switch unit 717, in an embodiment, is configured to turn on and turn off the percussive massage device with force meter 400. The power switch unit 717 is coupled to the OLED screen control system 712 and the microcontroller unit 701. In an embodiment, the power switch unit 717 is the switch 405.

Figure 3:
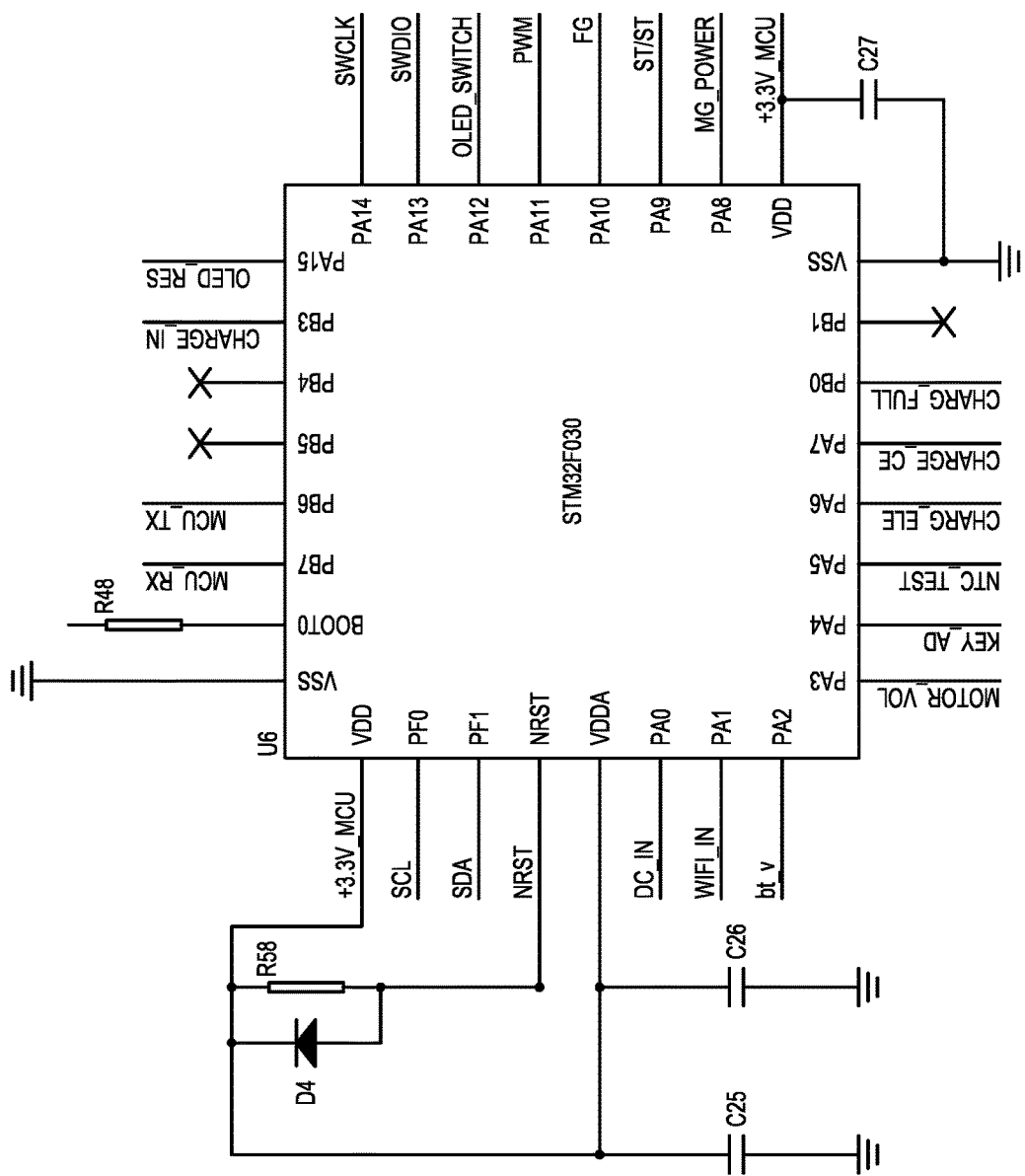
FIG. 3 is a circuit diagram of a microcontroller unit with pin outputs in accordance with one embodiment.

FIG. 3 shows a circuit diagram of the microcontroller unit 701 with pin outputs. In this embodiment, the STM32F030K6 series of microcontroller units is utilized. The circuit diagram depicts +3.3 volt power being provided to the VDD inputs of the microcontroller unit 701. Input PA3 is labeled "Motor_VOL", the voltage of the motor 713. Input PA2 is "bt_v", the battery or battery pack voltage. The microcontroller unit is configured to receive analog voltage on inputs PA2 and PA3 and to convert it to digital voltage using the microcontroller's analog-to-digital converter. In this embodiment, the analog-to-digital converter is a 12-bit ADC. One of ordinary skill in the art would understand that other microcontrollers may utilize voltage sensing and analog-to-digital converters to perform similar functions. In yet other embodiments, an analog-to-digital converter module separate from a microcontroller may be utilized.

Figure 4:
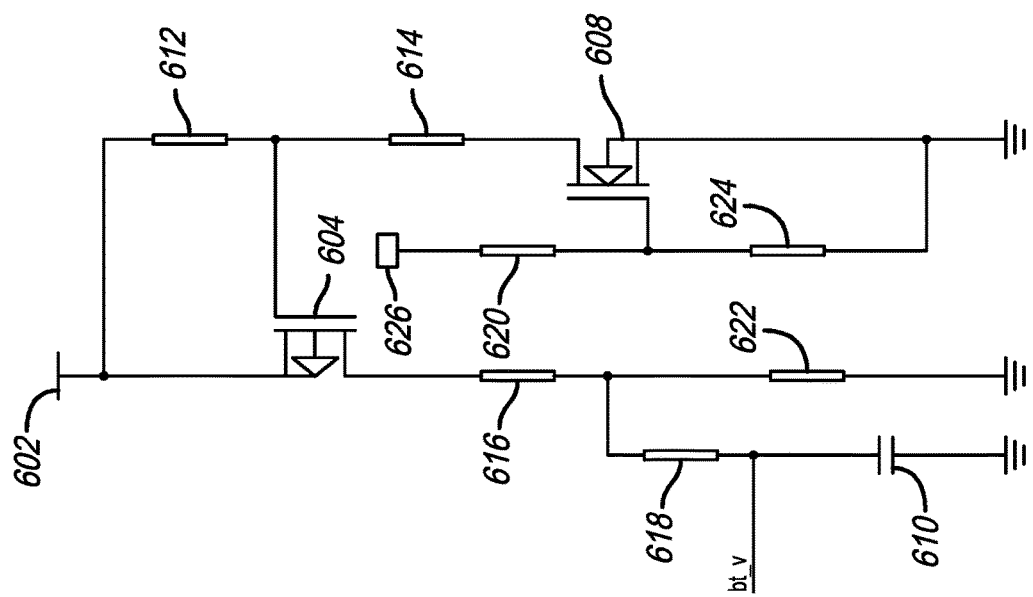
FIG. 4 is a circuit diagram used for battery voltage detection in accordance with one embodiment.

FIG. 4 shows a circuit diagram used for battery voltage detection. In this embodiment, +BT, the positive battery terminal 602, is coupled to a circuit consisting of a P-channel MOSFET 604, an N-Channel MOSFET 608, 0.1 µF capacitor 610, 100 kΩ resistors 612, 614, 68 kΩ resistor 616, 1 kΩ resistors 618, 620, and 10 kΩ resistors 622, 624. The circuit is configured to provide an input analog voltage of the battery or battery pack, or bt_v, to the microcontroller unit 701 of FIG. 2. In other embodiments, voltage of the battery or battery pack may be achieved using a voltage reader coupled to the terminals of the battery or battery pack.

Figure 5:
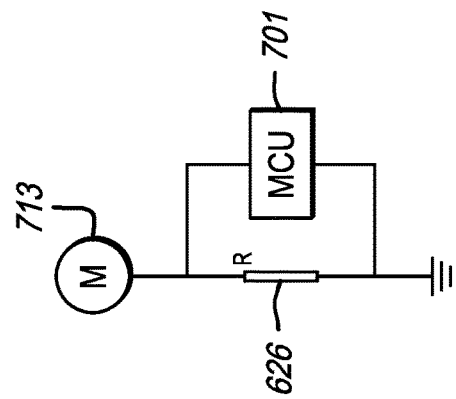
FIG. 5 is a circuit diagram for detection and measurement of voltage of the motor of the percussive massage device in accordance with one embodiment.

FIG. 5 shows a circuit diagram for detection and measurement of voltage of the motor 713 of the percussive massage device. In this embodiment, voltage sensing resistor 626 is coupled in parallel with the microcontroller unit 701, and coupled to the motor 713. In an embodiment, the voltage sensing resistor has a value of 0.0025Ω. The circuit depicted in FIG. 5 is configured to provide the Motor_VOL input into the microcontroller unit 701 of FIG. 2. In an embodiment, the input analog voltage is amplified. In another embodiment, the voltage of the motor 713 is measured or sensed using a separate series of electronic components or a standalone device and input into a microprocessor for use with the method of displaying a force on the percussive massage device.

Figures 6, 7:
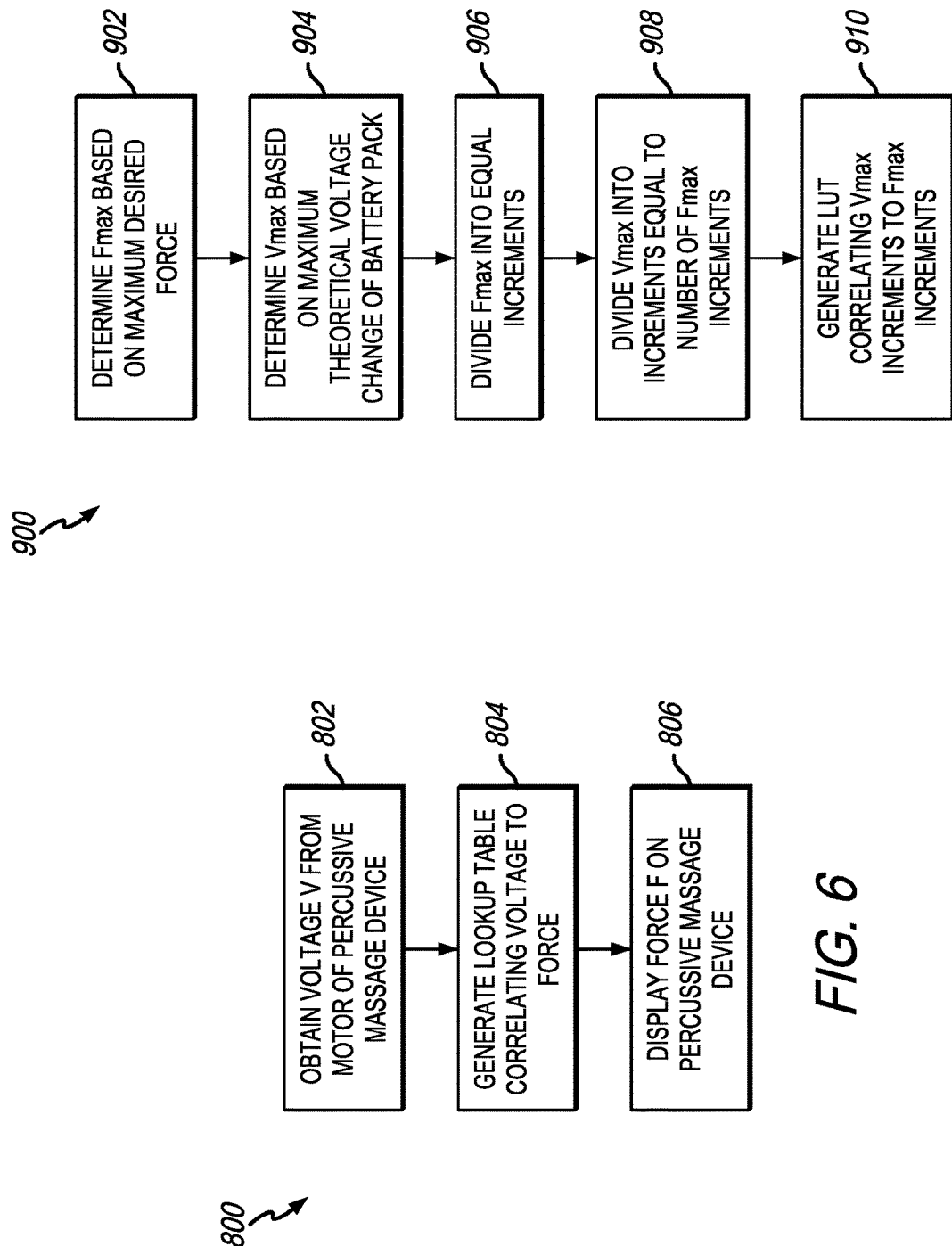
FIG. 6 is a flow diagram showing a method of detecting force applied by the percussive massage device in accordance with a preferred embodiment.
FIG. 7 is a flow diagram showing a method of generating a lookup table correlating voltage to force in accordance with a preferred embodiment.

FIG. 6 is a flow diagram showing a method 800 of detecting force applied by the percussive massage device in accordance with a preferred embodiment. At Step 802, a voltage magnitude V is obtained. In an embodiment, voltage magnitude V is an analog voltage obtained by using the circuit disclosed in FIG. 2. In that circuit, a block curve signal from the motor 713 (i.e., a Hall effect sensor) is simulated in the circuit as current using the resistor R, which is placed in parallel with the microcontroller unit 701. In other embodiments, voltage that corresponds to the current operating speed of the motor 713 may be generated in a variety of other ways. The voltage magnitude V may be input to a microcontroller unit 701 that converts analog voltage to digital voltage using an analog-to-digital converter, such as that implemented in the STM32F030K6 microcontroller unit. The STM32F030K6 microcontroller unit coverts analog voltage magnitude to a digital code corresponding to the 12-bit ADC (i.e., 0 to 4096). The digital code represents a voltage magnitude corresponding to the original voltage magnitude V obtained.

At Step 804, a lookup table is generated that correlates voltage V to force magnitude F. In an embodiment, the lookup table is generated using a method 900 of generating a lookup table correlating voltage to force. For example, the force magnitude F may be expressed in pounds of force. In an alternative embodiment, the force magnitude F may be expressed in Newtons of force.

At Step 806, the force magnitude F corresponding to voltage magnitude V is displayed on the percussive massage device with force meter 400. In an embodiment, a series of LED lights may be utilized to depict varying amounts of force as the force is being applied by the percussive massage device with force meter 400. Thus, as the amount of force magnitude F increases, more LEDs on the series of LED lights will be lit. Preferably, the series of LED lights consists of 12 LED lights.

FIG. 7 is a flow diagram showing a method 900 of generating a lookup table correlating voltage to force. At Step 902, a maximum magnitude of force, $F_{MAX}$, is determined. The magnitude of $F_{MAX}$ may be determined by assessing the maximum desired force to apply using the percussive massage device with force meter 400. As an example, $F_{MAX}$ is 60 pounds of force.

At Step 904, a maximum magnitude of voltage, $V_{MAX}$, is determined. The magnitude of $V_{MAX}$ may be determined by assessing the maximum theoretical voltage change possible by the percussive massage device with force meter 400. As an example, $V_{MAX}$ is 1.8 volts.

At Step 906, $F_{MAX}$ is divided into equal increments. Using the above example from Step 902, 60 pounds of force is divided into 60 one-pound increments.

At Step 908, $V_{MAX}$ is divided into the same amount of increments as determined in Step 906 above. Thus, using the above example from Step 904, 1.8 volts is divided into 60 0.03-volt increments.

Figure 8:
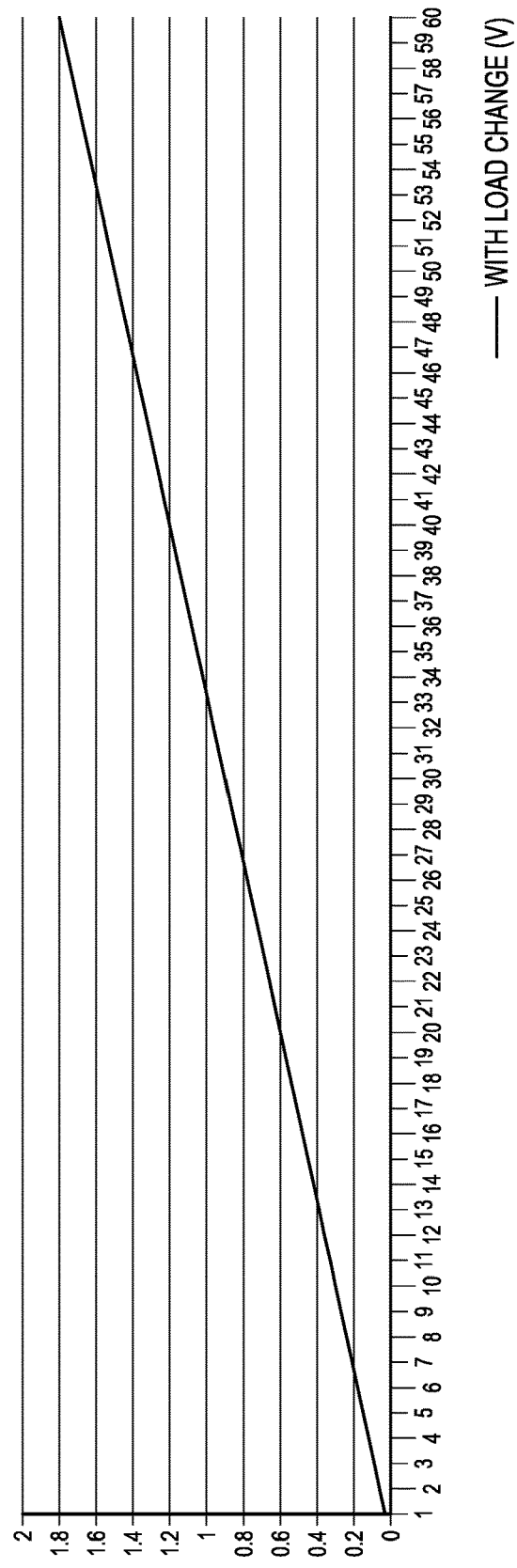
FIG. 8 is a graph plotting a lookup table for use by a method of detecting force applied by the percussive massage device that was generated by correlating voltage to force in accordance with a preferred embodiment.

At Step 910, a lookup table (LUT) is generated that correlates the increments of pounds of force with the increments of voltage. This necessarily creates a linear relationship between force and voltage. FIG. 8 is a graph plotting the LUT for use by the method of detecting force of FIG. 6 that was generated using the specific example identified in FIG. 7. The graph depicts calculated force that was calculated using the method 900.

A problem may arise in that the theoretical maximum voltage assumption at Step 904 in the method 900 is inaccurate. It may also be the case that as the percussive massage device with force meter 400 is used, the maximum available voltage degrades over time. In other words, the battery or battery pack voltage may decrease.

Figure 9:
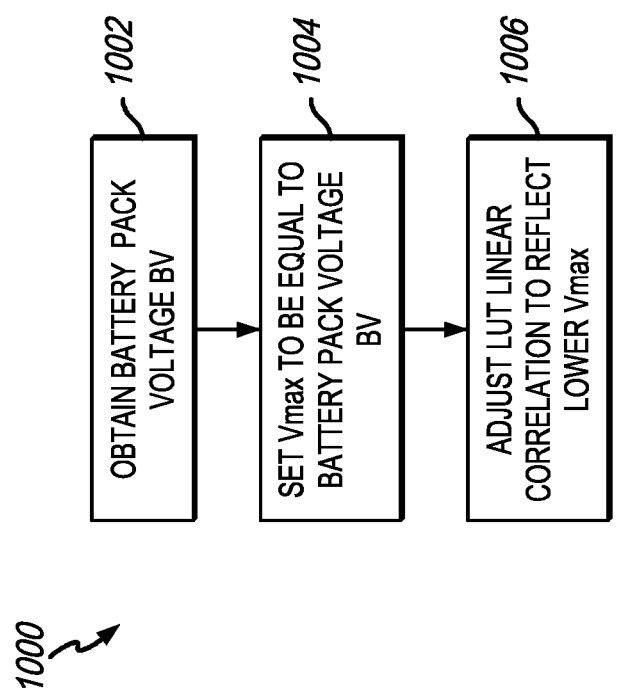
FIG. 9 is a flow diagram showing a method of calibrating a lookup table according to a preferred embodiment.

Accordingly, a method 1000 of calibrating the LUT generated by method 900 may be advantageous. FIG. 9 is a flow diagram showing a method 1000 of calibrating a LUT. At Step 1002, battery pack voltage BV is obtained. In an embodiment, battery pack voltage magnitude BV is an analog voltage obtained by using the circuit disclosed in FIG. 4. In that circuit, the battery pack voltage magnitude BV may be input to a microcontroller unit 701 that converts analog voltage to digital voltage using an analog-to-digital converter, such as that implemented in the STM32F030K6 microcontroller unit. The STM32F030K6 microcontroller unit coverts analog voltage magnitude to a digital code corresponding to the 12-bit ADC (i.e., 0 to 4096). The digital code represents a voltage magnitude corresponding to the original battery pack voltage magnitude BV obtained.

Figure 10:
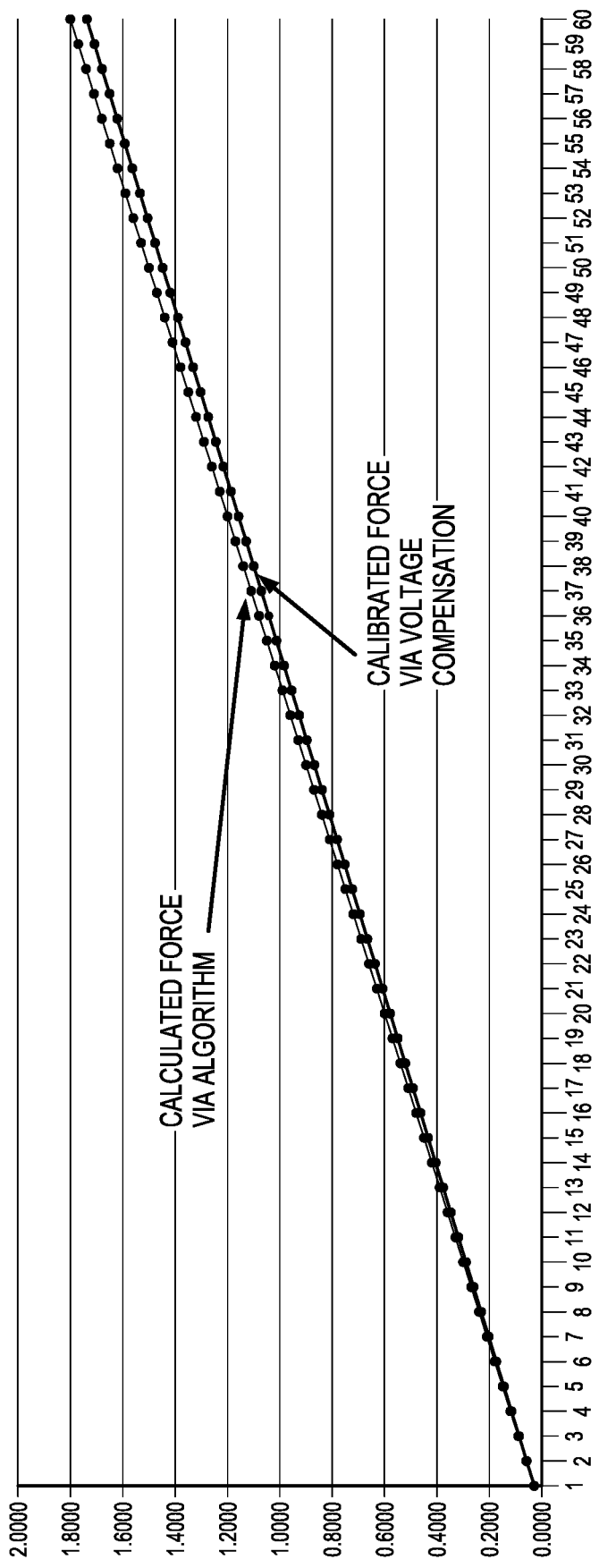
FIG. 10 is a graph plotting a lookup table generated by a method of detecting force applied by the percussive massage device against a lookup table calibrated by using a method of calibrating a lookup table according to a preferred embodiment.

At Step 1004, $V_{MAX}$ is set to the actual battery voltage magnitude BV output. As an example, may decrease from 1.8 volts to 1.74 volts, a 0.6 volt decrease. At Step 1006, the LUT linear correlation is adjusted to reflect the lower $V_{MAX}$. FIG. 10 is a graph plotting the LUT calculated by the method 900 against the LUT calibrated by using the method 1000. The LUT resulting from method 1000 depicts a calibrated force rather than a calculated force.

Figure 11:
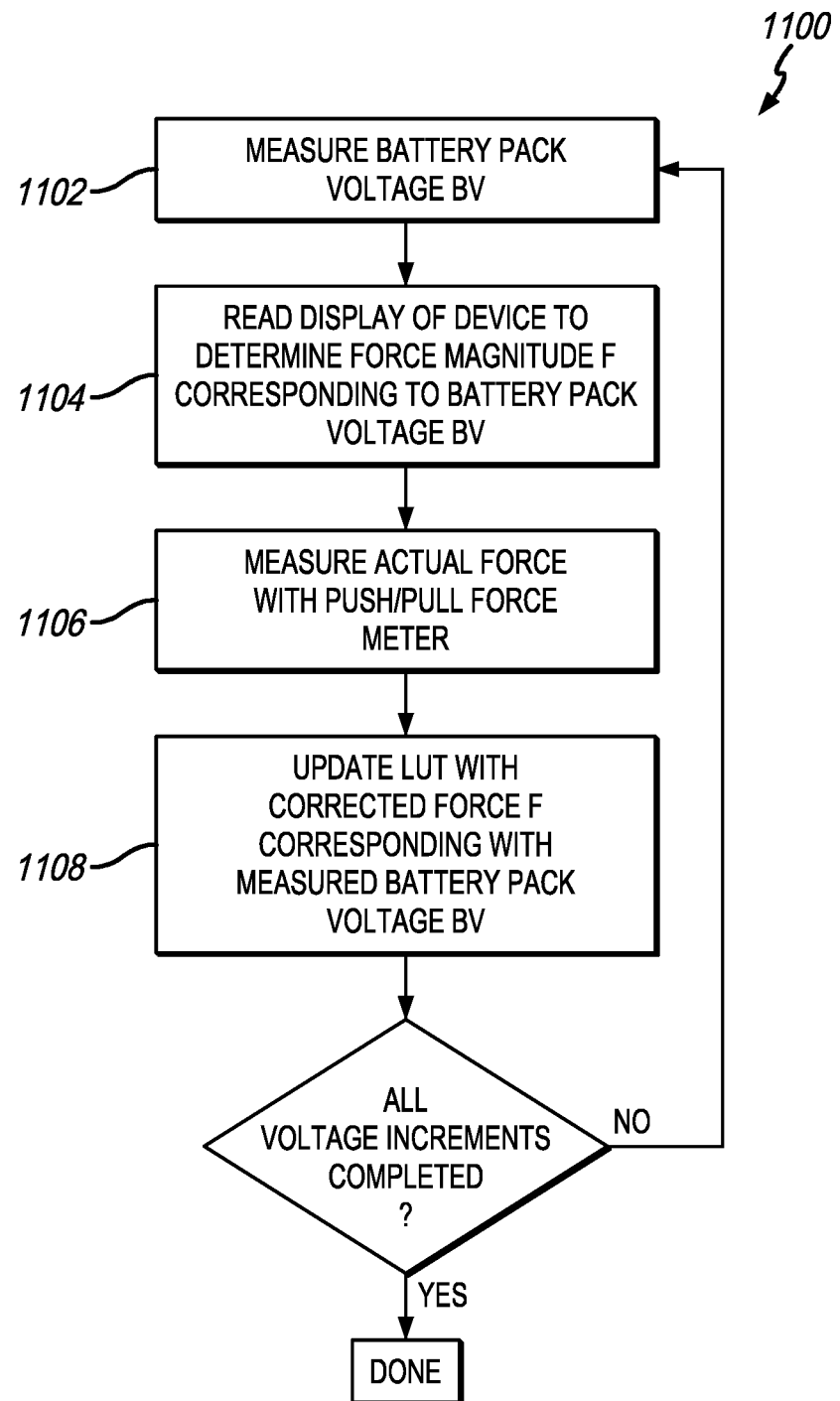
FIG. 11 is a flow diagram showing a method of calibrating a lookup table.

FIG. 11 is a flow diagram showing a method 1100 of calibrating a LUT. The method 1100 may be performed after the method 900, or entirely separately from the method 900. At Step 1102, battery pack voltage BV is measured. In an embodiment, the measurement is done without applying any force from the percussive massage device with force meter 400. In an embodiment, the battery pack voltage BV is measured using an external voltage meter. In another embodiment, the battery pack and/or microcontroller unit 701 have embedded solutions for directly measuring battery pack voltage BV.

At Step 1104, the display on the percussive massage device with force meter 400 that displays the force magnitude F is read to determine the force magnitude F corresponding to the measured battery pack voltage BV.

Figure 12:
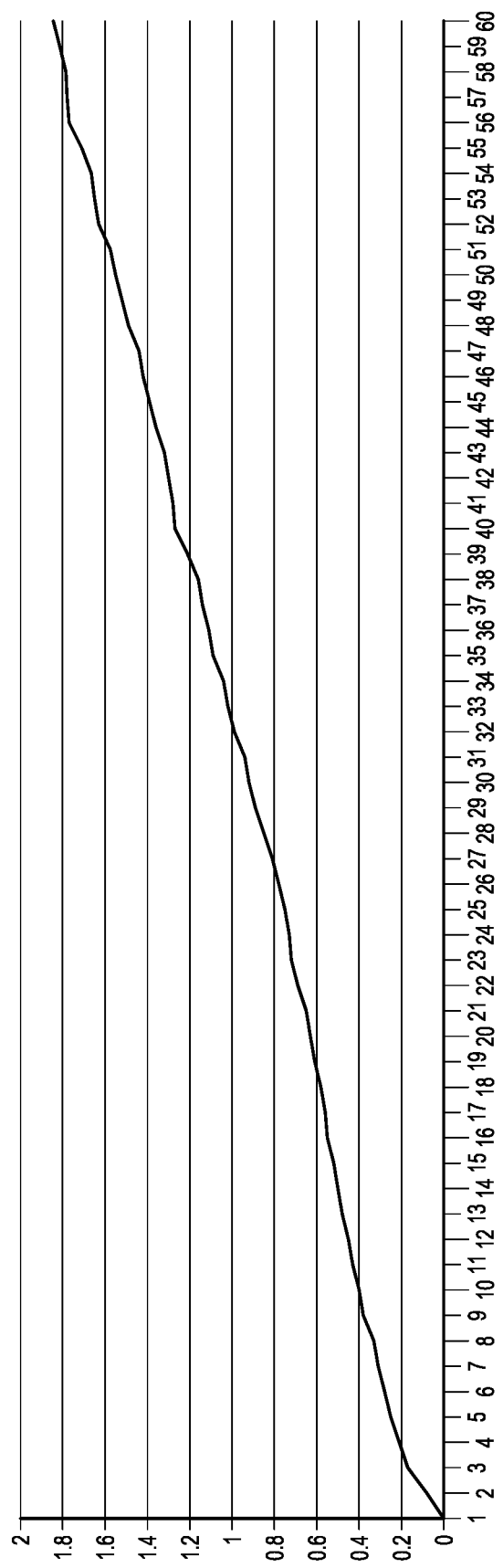
FIG. 12 is a graph plotting a lookup table after being calibrated in accordance with a preferred embodiment.

At Step 1106, a force meter is used to measure actual force being applied. In an embodiment, the force meter is a push/pull force meter. The direct measurement of force allows calibration of the LUT by comparing the displayed force magnitude F with the measured actual force. At Step 1108, the LUT is updated with a corrected force corresponding with the measured battery pack voltage BV. After Step 1108, Steps 1102-1106 are repeated for each successive voltage increment. In the embodiment depicted in accordance with the method 900, Steps 1102-1106 are repeated for every 0.03-volt increment. FIG. 12 is a graph plotting the LUT calculated by the method 1100 after all 3-volt increments had been updated.

Figures 13, 14:
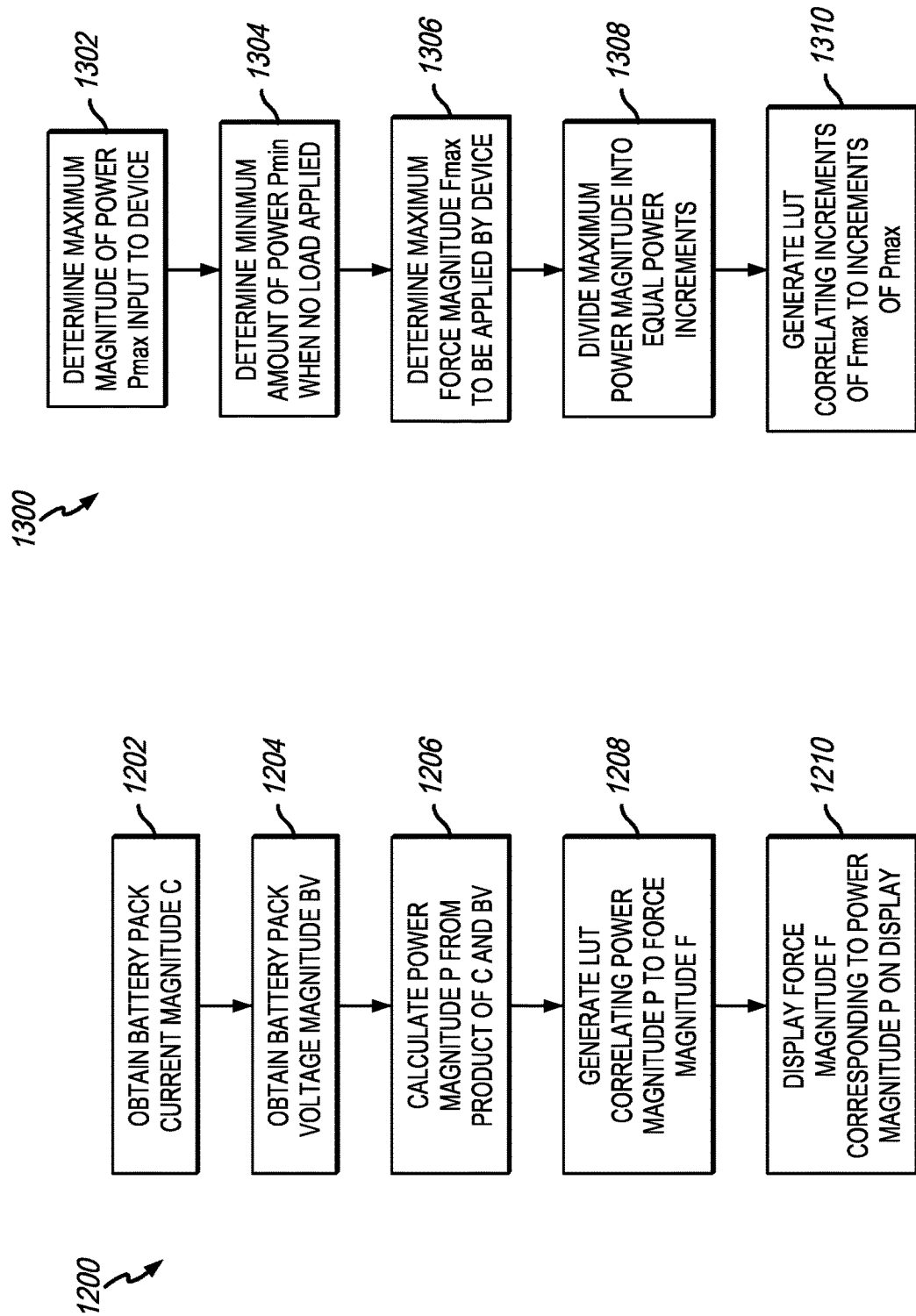
FIG. 13 is a flow diagram showing a method of detecting force applied by a percussive massage device in accordance with a preferred embodiment.
FIG. 14 is a flow diagram showing a method of generating a lookup table correlating power to force in accordance with a preferred embodiment.

FIG. 13 is a flow diagram showing a method 1200 of detecting force applied by a percussive massage device in accordance with a preferred embodiment. At Step 1202, current magnitude C of a battery pack is obtained. In an embodiment, current magnitude C is input into the microcontroller unit 701. At Step 1204, voltage magnitude BV of a battery pack is obtained. In an embodiment, voltage magnitude BV is input into the microcontroller unit 701. At Step 1206, power is calculated using the product of C and BV. In an embodiment, the microcontroller unit 701 is configured to calculate power by multiplying C and BV. At Step 1208, a lookup table is generated that correlates power magnitude P to force magnitude F. In an embodiment, the lookup table is generated using a method 1300 of generating a lookup table correlating power to force. For example, the power magnitude P may be expressed in watts. In an alternative embodiment, force magnitude F may be expressed in pounds of force or Newtons of force.

At Step 1210, the force magnitude F corresponding to power magnitude P is displayed on the percussive massage device with force meter 400. In an embodiment, a series of LED lights may be utilized to depict varying amounts of force as the force is being applied by the percussive massage device with force meter 400. Thus, as the amount of force magnitude F increases, more LEDs on the series of LED lights will be lit. Preferably, the series of LED lights consists of 12 LED lights.

FIG. 14 is a flow diagram showing a method 1300 of generating a lookup table correlating power to force. At Step 1302, a maximum magnitude of power, $F_{MAX}$, is determined. A theoretical maximum magnitude of power, however, is not a reasonable assumption if the total effective power may be calculated. Equation 1 may be utilized to determine Total Maximum Effective Power ($EP_{MAX}$).

Total $EP_{MAX} = P_{MAX} \times \text{TotalEP}$  Equation 1:

Equation 2 may be utilized to calculate Total EP, which is then input into Equation 1 above.

Total $EP = EP_{BATTERY} \times EP_{PCBA} \times EP_{MOTOR}$  Equation 2:

where Total EP, $EP_{BATTERY}$, $EP_{PCBA}$, and $EP_{MOTOR}$ are all expressed in percentages, and where PCBA is a printed circuit board assembly.

In an embodiment, EP (Battery) is 85%, EP (PCBA) is 95%, and EP (Motor) is 75%. Thus, using Equation 2, Total EP is 85%*95%*75%=60.5625%.

In this embodiment, $P_{MAX}$ is calculated by multiplying the maximum voltage $V_{MAX}$ and the maximum amperage $C_{MAX}$ of the battery pack such as in Equation 3. $P_{MAX}$ is then input into Equation 1.

$P_{MAX} = V_{MAX} \times C_{MAX}$

In this embodiment, $V_{MAX}$ is 16.8 volts and $C_{MAX}$ is 20 amperes. Thus, $P_{MAX}$ is 336 watts.

Turning back now to Equation 1, if $P_{MAX}$ is 336 watts and Total EP is 60.5625%, then Total $EP_{MAX}$ is 203 watts.

At Step 1304, a minimum amount of power $P_{MIN}$, is determined. It will be recognized by one of ordinary skill in the art that the power without any force being applied (i.e., no load) will be non-zero. Thus, $P_{MIN}$ of 12 watts is assumed. One of ordinary skill will also understand that the value of is equivalent to the rated power without load, which may be derived from $V_{MAX}$ and $C_{MIN}$.

At Step 1306, a maximum magnitude of force, $F_{MAX}$, is determined. The magnitude of $F_{MAX}$ may be determined by assessing the maximum desired force to apply using the percussive massage device with force meter 400. As an example, $F_{MAX}$ is 60 pounds of force.

At Step 1308, Total $EP_{MAX}$ is divided into equal increments. In an embodiment, Total $EP_{MAX}$ is divided in 3 watt increments per one pound of force, starting at $P_{MIN}$ (12 watts). It will be recognized by one of ordinary skill in the art that if $F_{MAX}$ is 60 pounds of force, the total desired force output of the percussive massage device with force meter 400, then 60 pounds of force correlates to 189 watts, within the calculated Total $EP_{MAX}$.

Figure 15:
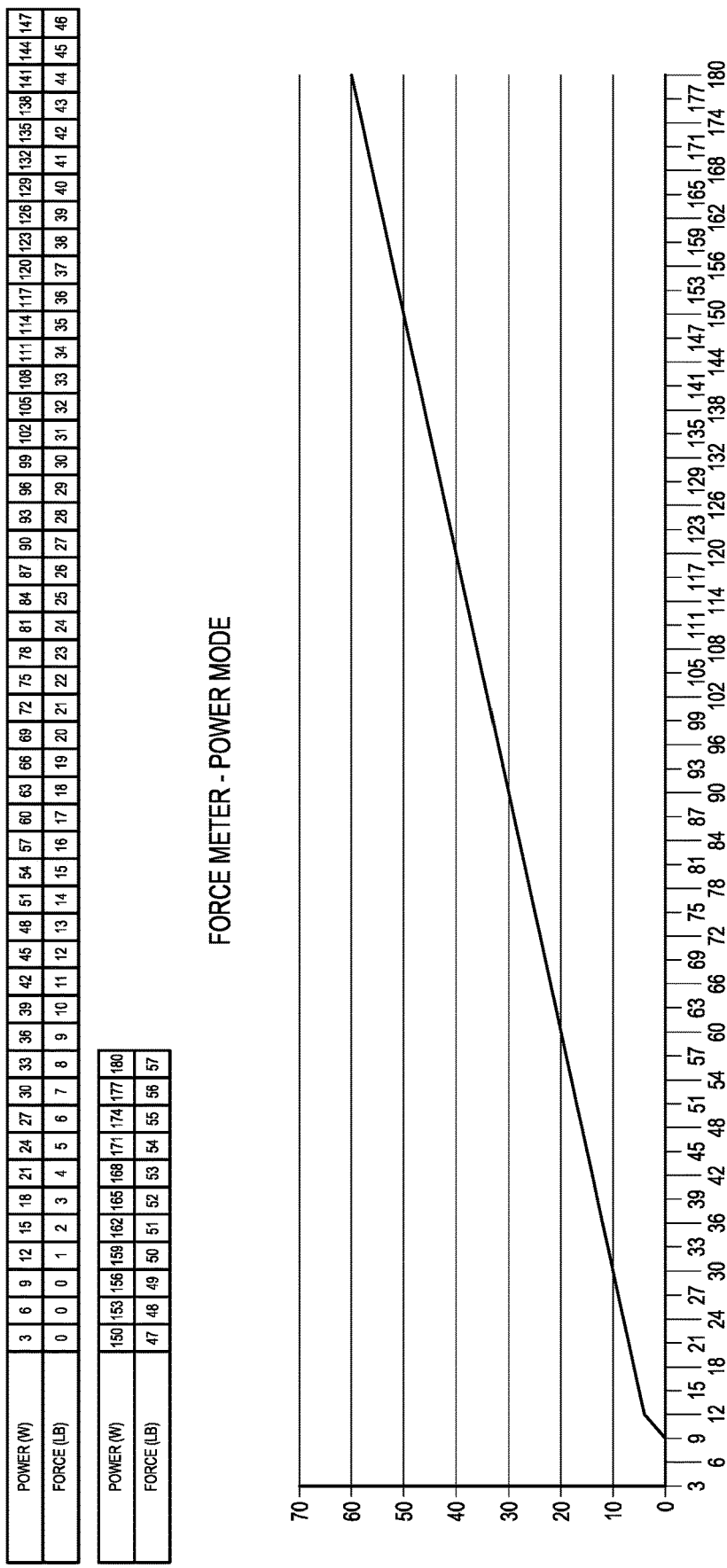
FIG. 15 is a graph plotting a lookup table for use by a method of detecting force of that was generated by correlating power to force in accordance with a preferred embodiment.

At Step 1310, a LUT is generated that correlates the increments of pounds of force with the increments of power in watts. This necessarily creates a linear relationship between force and voltage. FIG. 15 is a graph plotting the LUT for use by the method of detecting force of FIG. 13 that was generated using the specific example identified in FIG. 10. The graph depicts calculated force that was calculated using the method 1200.

Similarly to the method 900, a problem may arise in that the measured voltage of the battery pack at Step 1204 in the method 1200 is inaccurate. It may also be the case that as the percussive massage device with force meter 400 is used, the maximum available voltage degrades over time. In other words, the battery or battery pack voltage may decrease.

Figure 16:
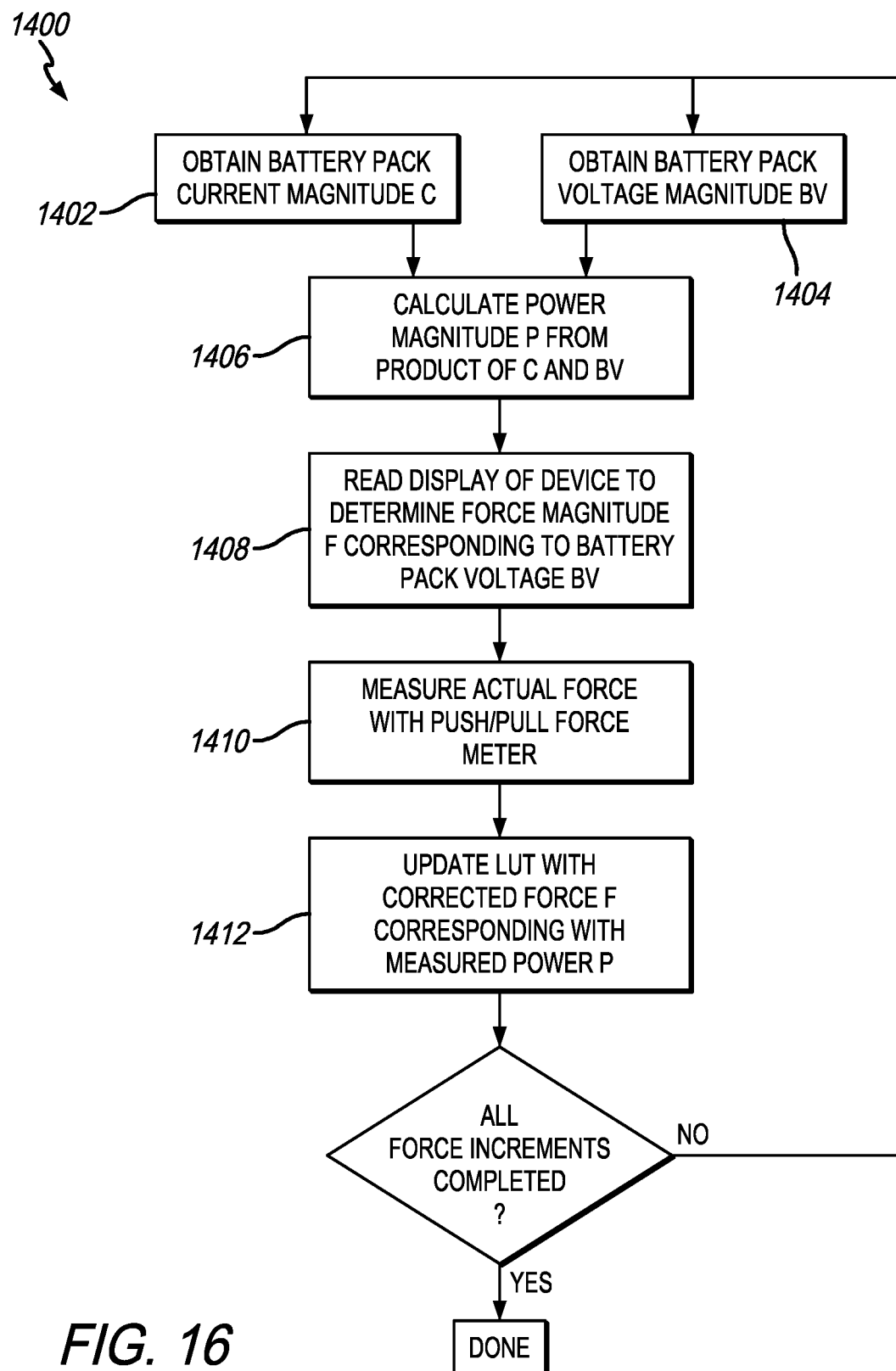
FIG. 16 is a flow diagram showing a method of calibrating a lookup table in accordance with a preferred embodiment.

FIG. 16 is a flow diagram showing a method 1400 of calibrating a LUT. The method 1400 may be performed after the method 900 or the method 1200, or entirely separately from the method 900 or the method 1200. At Step 1402, current magnitude C of a battery pack is obtained. In an embodiment, current magnitude C is input into the microcontroller unit 701.

At Step 1404, battery pack voltage BV is measured. In an embodiment, the measurement is done without applying any force from the percussive massage device with force meter 400. In an embodiment, the battery pack voltage BV is measured using an external voltage meter. In another embodiment, the battery pack and/or microcontroller unit 701 have embedded solutions for directly measuring battery pack voltage BV. At Step 1406, power is calculated using the product of C and BV. In an embodiment, the microcontroller unit 701 is configured to calculate power by multiplying C and BV.

Figure 17:
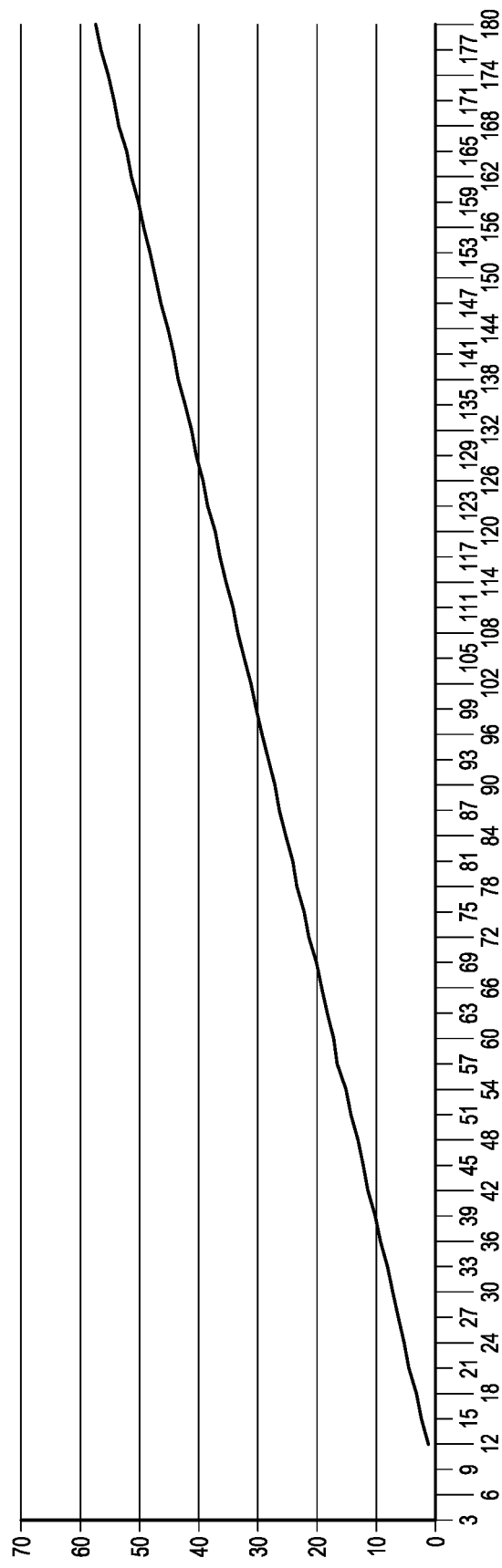
FIG. 17 is a graph plotting a lookup table after being calibrated in accordance with a preferred embodiment.

At Step 1408, the display on the percussive massage device with force meter 400 that displays the force magnitude F is read to determine the force magnitude F corresponding to the calculated power. At Step 1410, a force meter is used to measure actual force being applied. In an embodiment, the force meter is a push/pull force meter. The direct measurement of force allows calibration of the LUT by comparing the displayed force magnitude F with the measured actual force. At Step 1412, the LUT is updated with a corrected force corresponding with the measured power. After Step 1412, Steps 1402-1410 are repeated for each power or force increment. In the embodiment depicted in accordance with the method 900, Steps 1402-1410 are repeated for every 3-watt increment. FIG. 17 is a graph plotting the LUT calculated by the method 1400 after all 3-watt increments had been updated.

Figure 18:
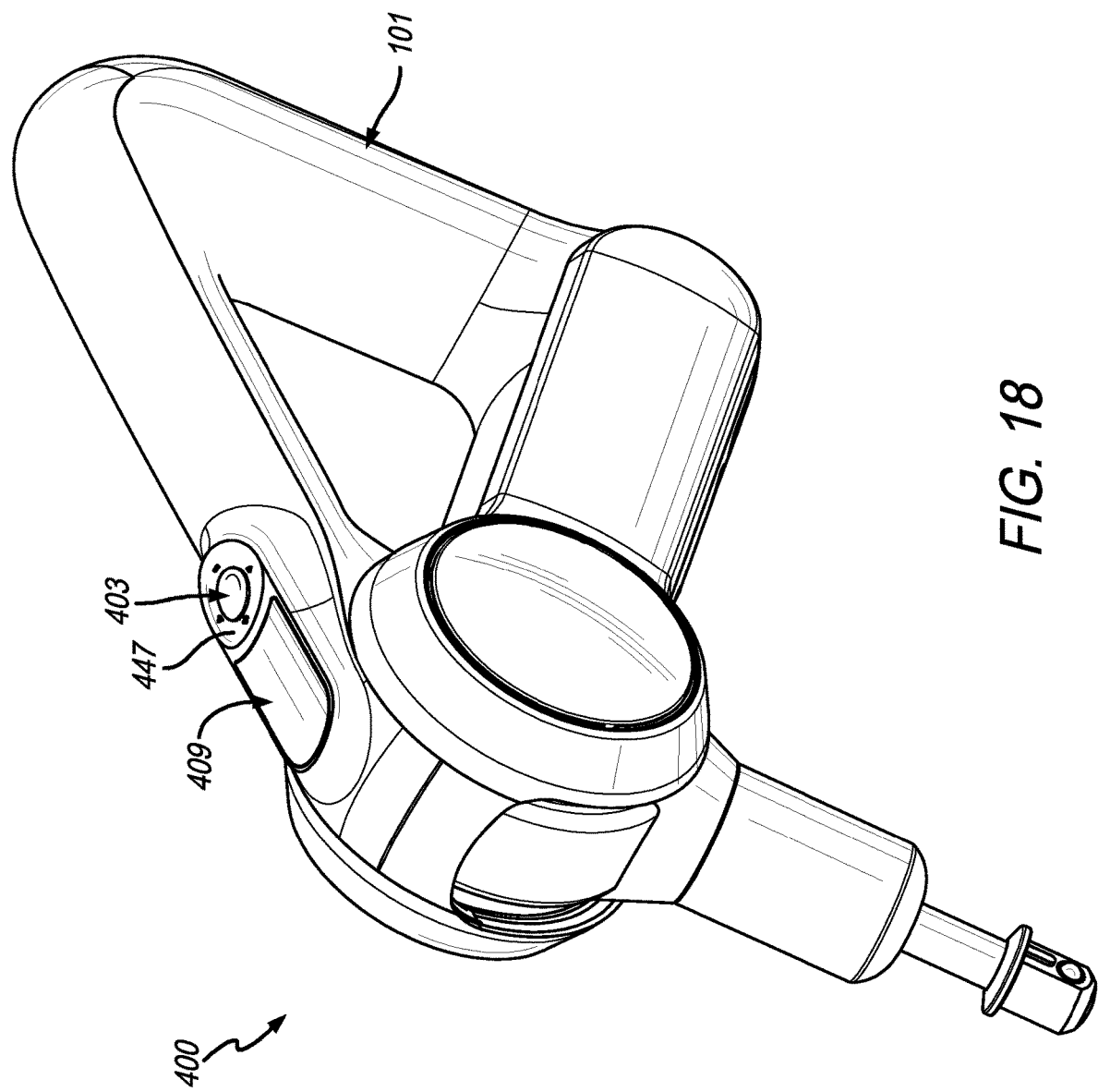
FIG. 18 is a perspective view of a percussive massage device in accordance with a preferred embodiment of the present invention.
Figure 20:
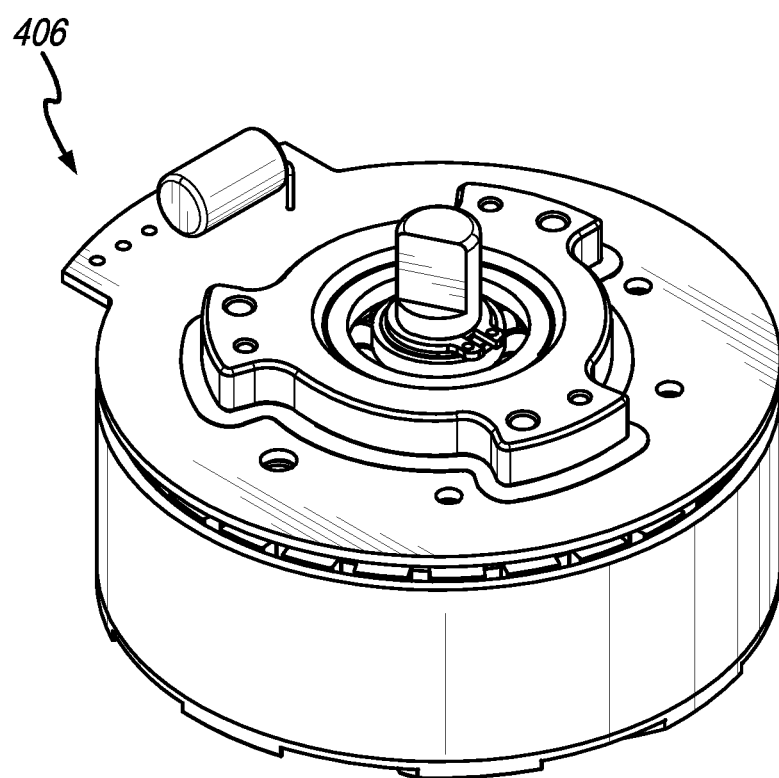
FIG. 20 is a perspective view of the motor.

FIGS. 18-19 show an exemplary percussive massage device 400 that embodies the features disclosed herein. Generally, the percussive massage device 400 includes a housing 101, an electrical source or battery pack 114, a motor 406 positioned in the housing 101, and a switch 405 for activating the motor 406. The electronics (see printed circuit board 408 in FIG. 19) includes the controller that is configured to obtain a voltage of the motor, generate a lookup table correlating voltage to force applied by the percussive massage device, and display a force magnitude corresponding to the obtained voltage using the lookup table. FIG. 20 is a perspective view of the motor 406.

Figure 21:
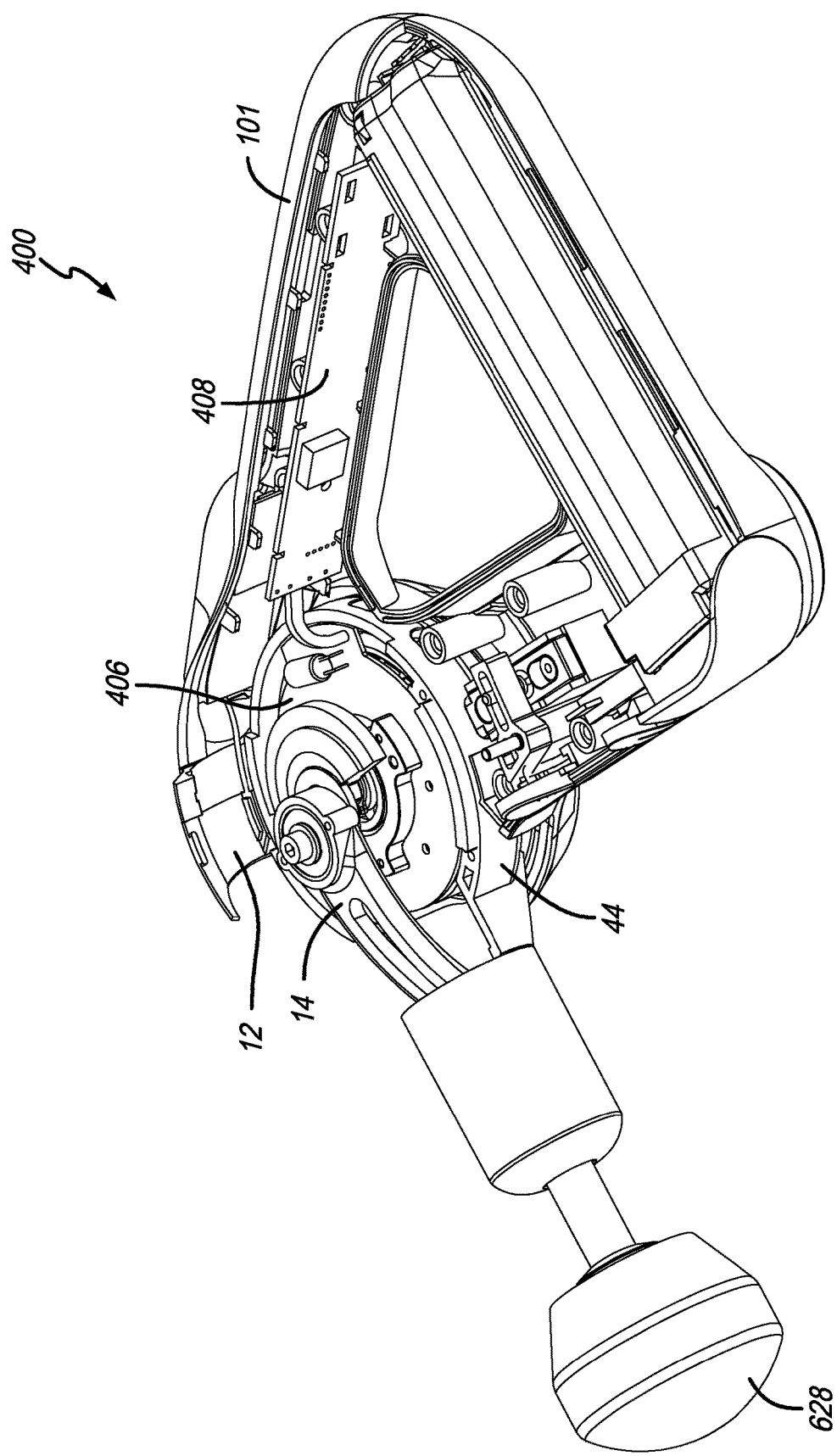
FIG. 21 is a perspective view of the percussive massage device of FIG. 18 with a portion of the housing removed.
Figure 22B:
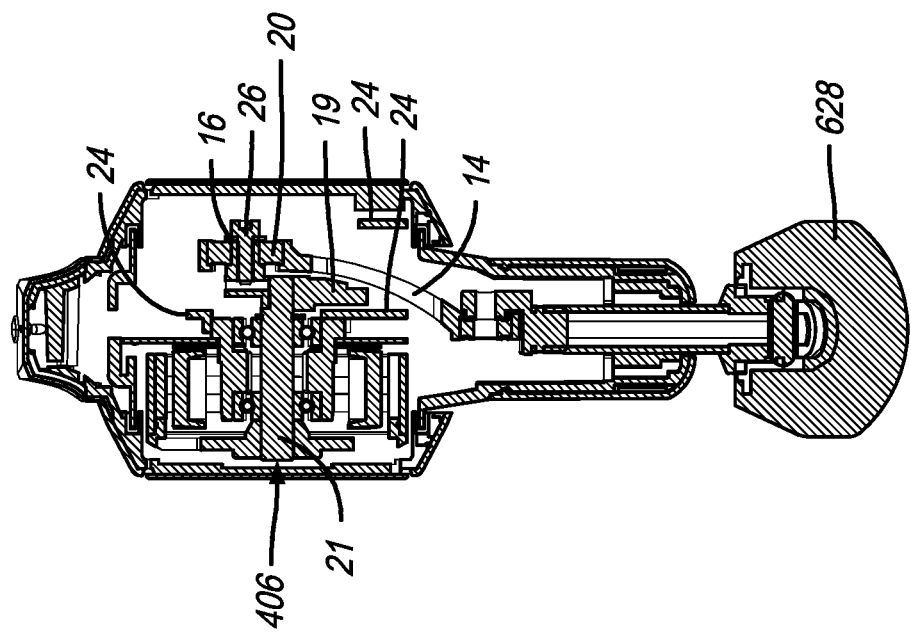
FIGS. 22A and 22B are cross sectional views of the head portion and motor.
Figure 22A:
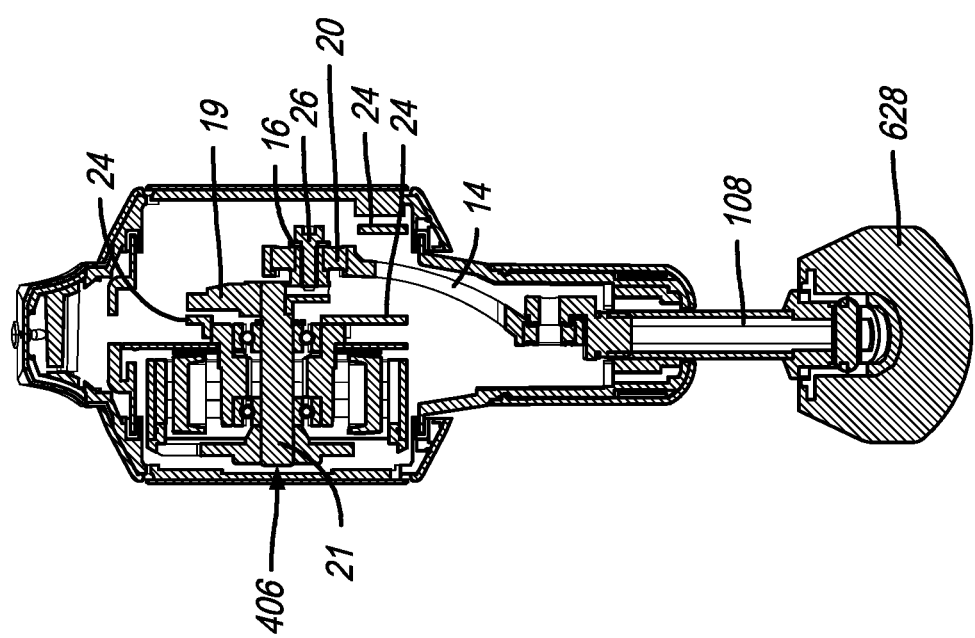
Figure 23:
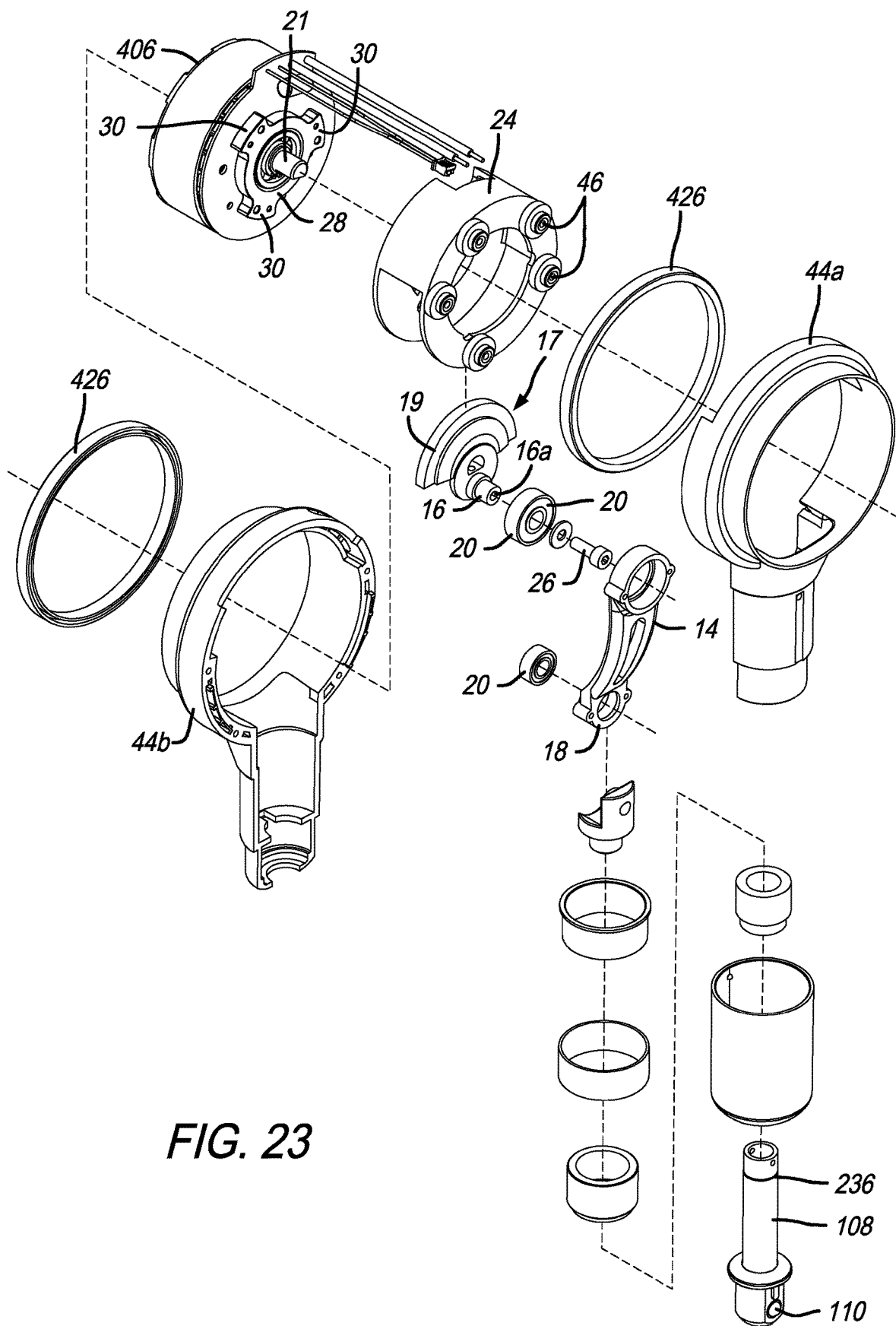
FIG. 23 is an exploded view of some of the internal components of percussive massage device of FIG. 18.

As shown in FIGS. 21-23, in a preferred embodiment, the motor 406 is located in the head portion 12. The percussive massage device 400 can include a rotatable arm that is part of rotation housing 44. The motor 406 is located in the rotation housing 44, which is housed with the head portion 12 of the housing 101. In another embodiment, the rotation capability can be omitted.

In a preferred embodiment, the device includes a push rod or shaft 14 that is connected directly to a shaft 16 that is rotated by the motor 406 and the motor shaft 21 extending therefrom. The shaft 16 can be part of a counterweight assembly 17 that includes a counterweight 19. In a preferred embodiment, the push rod 14 is L-shaped or includes an arc shape, as shown in FIGS. 22A-22B. Preferably, the point where the push rod 14 is connected to the shaft 16 is offset from the reciprocating path that the distal end 18 of the push rod 14 (and the massage attachment 628) travel. This capability is provided by the arc or L-shape. It should be appreciated that the push rod 14 is designed such that it can transmit the force at least partially diagonally or in an arc along its shape instead of vertically so the motor can be located at or near the middle of the device, otherwise a large protrusion would be necessary to keep the shaft in the center with the motor offset therefrom (and positioned in the protrusion). The arc also allows the push rod 14 to have a close clearance with the motor, as shown in FIGS. 22A and 22B and allows the outer housing to be smaller than similar prior art devices, therefore making the device 400 lower profile. FIG. 22A shows the push rod 14 at the bottom dead center of its travel and FIG. 22B shows the push rod 14 at the top dead center of its travel. Preferably one or more bearings 20 are included at the proximal end of the push rod 14 where it connects to the motor to counteract the diagonal forces and preventing the push rod 14 from moving and touching the motor 406. The bearing 20 is received on shaft 16 and a threaded fastener 26 is received in a co-axial opening 16a in shaft 16. The proximal end of the push rod 14 is received on bearing 20. These components are all shown in FIG. 23.

In a preferred embodiment, device 400 includes a number of dampening components that are made of an elastomer or the like and damp vibrations to keep the device relatively quiet. For example, as shown in FIG. 23, device 400 includes dampening rings 426 (similar to inner suspension rings 219) that surround the rotation housing 44 (with first and second rotation housing halves 44a and 44b) and help dampen the sound of vibration between the rotation housing and outer housing 101.

Figure 23A:
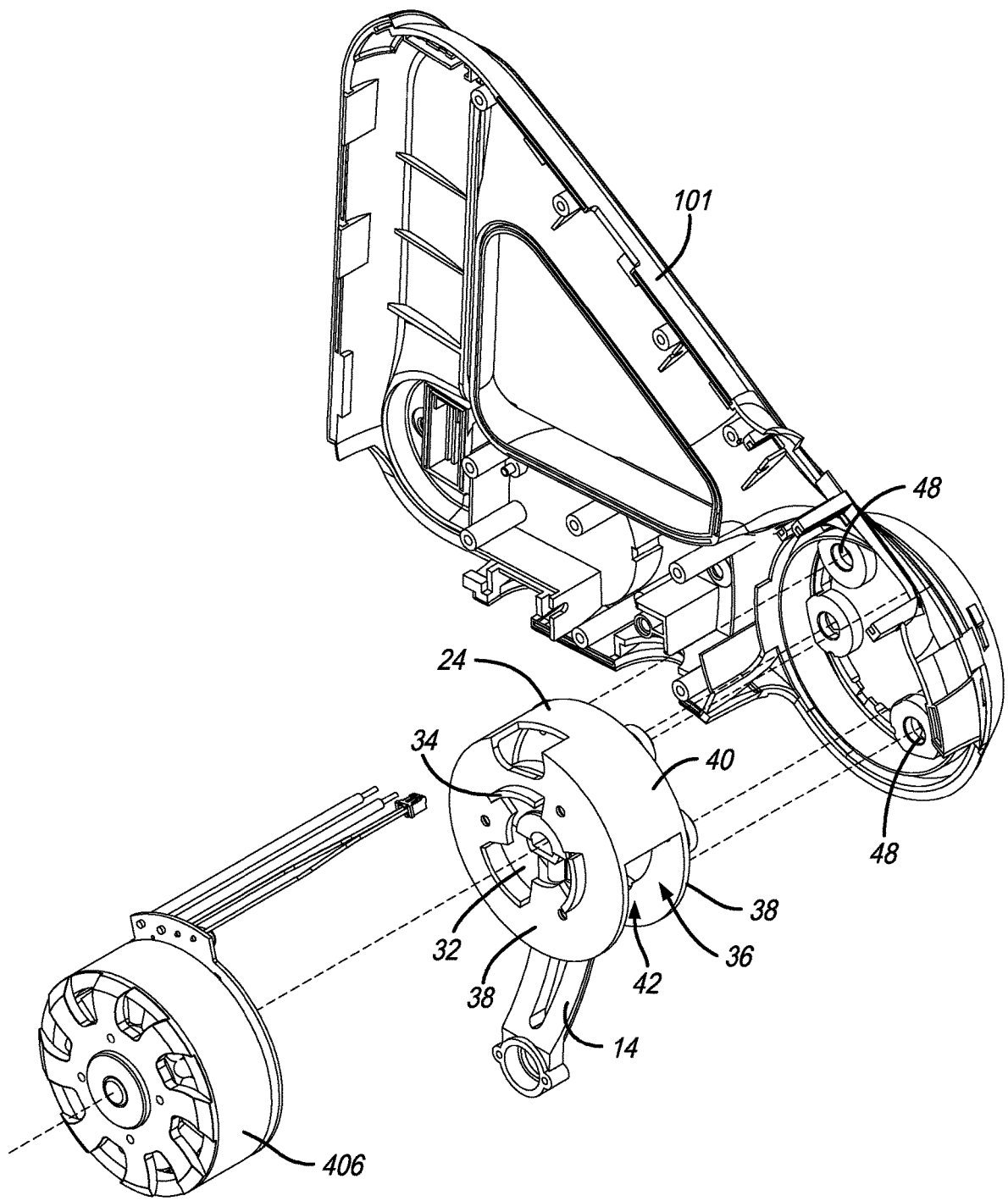
FIG. 23A is an exploded view of the motor and motor mount.

As shown in FIGS. 23 and 23A, the device 400 preferably also includes a motor mount 24 that secures the motor 406 in place and is secured to the housing 101. Motor 406 includes a receiving member 28 with three protrusions 30 (and number between one and ten can be included) that is received in a protrusion opening 32 defined in the motor mount 24 (in first wall 38). Flanges 34 extending from the motor mount 24 help keep the protrusions 30 in place. The motor 406 is preferably secured via threaded fasteners or the like to the motor mount 24. Motor shaft 21 extends into the motor mount interior 36, which is defined between first and second walls 38 and a side 40 that extends part of the way around the circumference. The counterweight assembly 17, proximal end of the push rod 14 and related components for converting the rotation of the motor shaft 21 to reciprocating motion are position in the motor mount interior 36. The push rod 14 extends downwardly out of the motor mount interior and through a push rod opening 42 in the side 40. In a preferred embodiment, the motor mount 24 is connected directly to the housing 101 via fasteners 46 that are secured to mounting members 48 in the housing (see FIG. 23A). It will be appreciated that the term push rod assembly used herein includes any of the components discussed herein or combinations thereof, e.g., push rod 14, output shaft 108, that extend from the rotating motor shaft 21 or the like that provides reciprocating motion and includes the attachment on the distal end thereof. The push rod assembly also includes the male connector 110 (and any related components) or any other connector at the end of the reciprocating components that allows connection of an attachment to be used for massage or therapy.

In a preferred embodiment, the device 400 is associated with and can be operated by an app or software that runs on a mobile device such as a phone, watch or tablet (or any computer). The app can connect to the device 400 via bluetooth or other wireless connection protocol. The app can have any or all of the following functions. Furthermore, any of the functions discussed herein can be added to the touch screen/scroll wheel or button(s) capability directly on the device. If the user walks or is located too far away from the device, the device will not work or activate. The device can be turned on an off using the app as well as the touch screen or button on the device. The app can control the variable speeds (e.g., anywhere between 1750-3000 RPM). A timer can be implemented so the device stops after a predetermined period of time.

In a preferred embodiment the device, via the app or the touch screen and other functional buttons, etc. includes different treatment protocols or routines associated therewith. During the routine, the device can vary different aspects or outputs of the device or make changes based on time, speed (frequency), amplitude (stroke), arm position, force, temperature, grip (i.e., which handle portion to grip), attachment (e.g., cone, ball, dampener, etc.) and body part. The device (via the app, touch screen, haptic feedback or audibly via a speaker) can also prompt the user to make some of these changes at certain points throughout the routine, e.g., arm position, grip, attachment changes and body part changes. One of ordinary skill in the art will understand that, depending upon the particular design of the device, one or more of these outputs are applicable, while in other devices, all options described are applicable.

When the start of the protocol is selected, the device runs through a preprogrammed routine. For example, the device may operate at a first RPM for a first period of time and then operate at a second RPM for a second period of time and/or at a first amplitude for a first period of time and then operate at a second amplitude for a second period of time. The routines can also include prompts (e.g., haptic feedback) for letting the user to know to move to a new body part. These routines or treatments can be related to recovery, blood flow increase, performance, etc. and can each include a preprogrammed routine or protocol. These routines can also help facilitate certain activities, such as sleep, interval training, stairs, post-run, post-workout, recovery, wellness, post-core exercise, high intensity (plyometric) workouts, among others. The routines can also assist in providing relief and recovery from ailments such as plantar fasciitis, "tech neck," muscle cramps, jet lag, sciatica, carpal tunnel, knots, and shin splints, among others. The routines can also prompt or instruct the user to switch attachments (e.g., attachment 628 shown in FIG. 21) or positions of the arm or rotation housing. The prompts can include sounds, haptic feedback (e.g., vibration of the device or mobile device), textual instructions or visual representation such as a graphic or picture on the app or touch screen, etc. For example, the app may instruct the user to start with the ball attachment with the arm in position two. Then the user hits start and the device runs at a first frequency for a predetermined amount of time. The app or device then prompts the user to begin the next step in the routine and instructs the user to change to the cone attachment and to place the arm in position 1 (e.g., see the arm position in FIG. 18). The arm can include any number of positions, e.g., 1-10 positions or 1-3 positions or 1-2 positions. The user hits start again and the device runs at a second frequency for a predetermined amount of time. The protocol can be divided into steps where, at each step, varied outputs are predetermined or specified.

Referring again to FIGS. 18-19, in a preferred embodiment, the device 400 includes a housing 101, an electrical source 114, a motor 406 positioned in the housing 101, a switch 405 (which can be any of the touch screen 409, rocker button 447, button 403 or any other switch or button) for activating the motor 406, and a routine controller 630. The device 400 is configured to mate with an attachment 628. The attachment can be, for example, the attachment 628 shown in FIG. 21. The attachment is affixed to the male connector 110 so that the shaft or push rod assembly 108 moves the attachment reciprocally in accordance with a specified amplitude. For example, the amplitude is depicted in FIGS. 22A and 22B, where FIG. 22A shows the attachment at a maximum extended position and FIG. 22B shows the attachment at a minimum extended position. The distance between maximum and minimum extended positions can, in an embodiment, define the amplitude.

The routine controller 630 is configured to perform a routine in connection with one or more specified protocols. The routine controller 630 can be, for example, the microcontroller unit 701 depicted in FIG. 2. The routine controller 630 can also be a standalone microcontroller separate from the microcontroller 701. The routine controller can step through different steps of a specified protocol designed to target specified muscle groups and to provide certain therapeutic effects, as described herein.

FIG. 24 is a table showing an example of a protocol in accordance with a preferred embodiment. Protocol 1 is divided into four steps, each depicting a specified time, speed, amplitude, attachment, force, temperature, and grip. At Step 1, the device 400 is activated for 30 seconds at a speed of 1550 RPM. A routine controller 630 may be utilized to turn on the percussive massage device and implement a speed of the attachment 628 of 1550 RPM. One of ordinary skill in the art would understand that the speed of the attachment 628 is directly proportional to the speed of the motor 406. The amplitude of the percussive massage device is set to be 2 in accordance with Protocol 1. This may translate to a specified distance that an attachment 628 moves while in use, as described above. Step 1 also specifies a dampener attachment affixed to the device 400, a force of "1" be applied by the device 400, and a temperature of 21° C. be applied to the attachment.

One of ordinary skill in the art would understand that the force to be applied by the device 400 may depend upon the pressure exerted by the user in pressing the attachment onto a person's body part. As described more fully herein, the force to be applied by the device 400 may be the target force. In an embodiment where the user provides pressure to exert a particular force upon a person's body part, the routine controller 630 may adjust the output of the device 400 to ensure that the force actually applied by the attachment is the target force. The routine controller 630 may also be configured to provide feedback to the user to increase or decrease pressure on a person's body part to meet the target force. Each of these embodiments is applicable to each of the steps of a given protocol, including in Steps 2-4 below, as well as Steps 1-4 of the protocol shown in FIG. 25.

Step 1 also specifies that the device 400 is to be operated using grip 1. Grip 1, for example, may be a grip on the first handle portion 143, otherwise referred to as a "regular" or "standard" grip. Grip 2, for example, may be a grip on the third handle portion 147, otherwise referred to as a "reverse" grip. An "inverse" grip can also be used on third handle portion 147. Grip 3, for example, may be a grip shown on the second handle portion 145, otherwise referred to as a "base" grip.

At Step 2, Protocol 1 specifies that the device 400 be activated for 15 seconds at 2100 RPM, with an amplitude of "3", a force of "3", and a temperature of 26° C. Step 2 specifies that the small ball attachment 628 be used, and that the device 400 is to be operated using grip 1. Step 2 therefore requires that the dampener attachment in Step 1 be replaced by the small ball attachment, but specifies that the same grip is to be used.

At Step 3, Protocol 1 specifies that the device 400 be activated for 30 seconds, at 2200 RPM, with an amplitude of "1", a force of "3", and a temperature of 29° C. Step 3 specifies that the dampener attachment 628 be used, and that the device 400 is to be operated using grip 1. Step 3 therefore requires that the small ball attachment in Step 2 be replaced by the dampener attachment, but specifies that the same grip is to be used.

At Step 4, Protocol 1 specifies that the device 400 be activated for 45 seconds, at 2400 RPM, with an amplitude of "4", a force of "2", and a temperature of 32° C. Step 3 specifies that the large ball attachment be used, and that the device 400 is to be operated using grip 1. Step 3 therefore requires that the dampener attachment in Step 2 be replaced by the large ball attachment, but specifies that the same grip is to be used. It will be appreciated that Protocol 1 is provided as an example to the reader of many of the different outputs that can be changed during a myriad of treatment protocols that can be provided or developed. It will be further appreciated that any one or more of the outputs can be a part of a protocol or routine and any of the outputs discussed herein can be omitted. For example, a protocol may only include time and speed or only time speed and force, or only time, speed and grip or any other combination of the outputs described herein.

FIG. 25 is a table showing an example of a "Shin Splints" protocol in accordance with a preferred embodiment. Like Protocol 1, the Shin Splints protocol is divided into four steps, each depicting a specified time, speed, amplitude, attachment, force, temperature, and grip, but also specifying a particular arm position and body part to which to apply the attachment. At Step 1, the device 400 is activated for 1 minute at a speed of 1500 RPM, with an amplitude of "1", a force of "2", and a temperature of 21° C. Step 1 specifies that the dampener attachment be used, and that the device 400 is to be operated using grip 2 ("Reverse"), to the right shin.

Step 1 also specifies the arm position to be used is arm position 1. One of ordinary skill in the art would understand that the numbers of arm position (e.g., 1, 2, 3, 4, etc.) are predetermined arm positions intended to be used during a particular protocol. The part of the body to which the attachment 628 is to be applied is one of the factors in determining an optimal arm position. The arm position, however, may be determined by the user and is not required to otherwise implement a protocol. As discussed above, a "standard" grip may be utilized with arm position to apply to specific parts of the body, a "reverse" grip may be utilized with arm position to apply to specific parts of the body, and a "base" grip may be utilized with arm position to apply to specific parts of the body. One of ordinary skill in the art would recognize that the any arm position in combination with the particular grip 143, 145, 147 may vary depending on the application. One of ordinary skill in the art will understand that setting the arm position of a device 400 depends upon the specific device. For example, certain devices may allow a user to adjust arm position while others do not. For those that do not, this step does not apply. In other embodiments, this step may be performed during execution of the steps of the particular protocol.

At Step 2, the Shin Splints protocol specifies that the device 400 be activated for 1 minute at 1500 RPM, with an amplitude of "1", a force of "2", and a temperature of 21° C. Step 2 specifies that the dampener attachment be used, and that the device 400 is to be operated using grip 2 ("Reverse"), at an arm position 1, to the left shin. Step 2 therefore uses the same attachment, grip, and arm position as Step 1, but is applied to the other shin.

At Step 3, the Shin Splints protocol specifies that the device 400 be activated for 1 minute at 2000 RPM, with an amplitude of "3", a force of "3", and a temperature of 24° C. Step 2 specifies that the dampener attachment be used, and that the device 400 is to be operated using grip 3 ("Base"), at an arm position 1, to the right calf. Step 3 therefore requires that the user change grips from "reverse" to "base" grips, but specifies that the same attachment and arm position be used.

At Step 4, the Shin Splints protocol specifies that the device 400 be activated for 1 minute at 2000 RPM, with an amplitude of "3", a force of "3", and a temperature of 24° C. Step 2 specifies that the dampener attachment be used, and that the device 400 is to be operated using grip 3 ("Base"), at an arm position 1, to the left calf. Step 2 therefore uses the same attachment, grip, and arm position as Step 1, but is applied to the other calf.

Figure 26A:
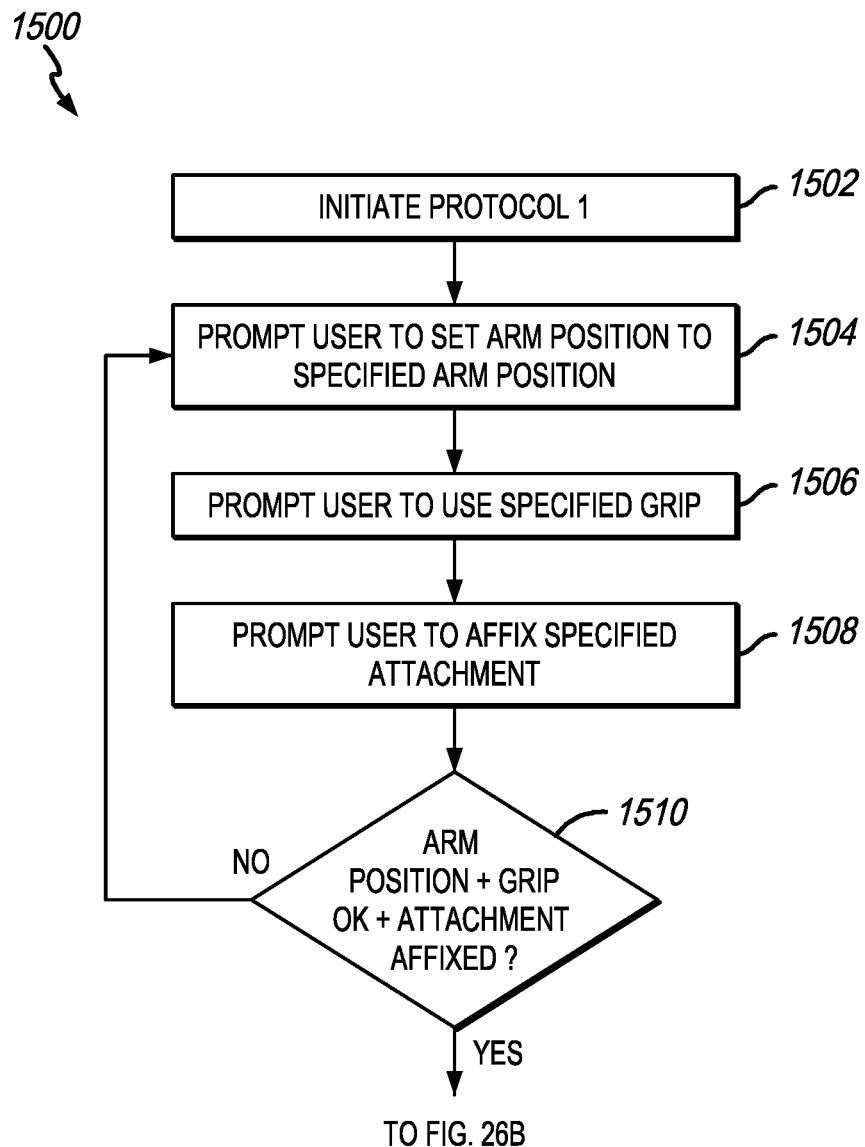
FIGS. 26A, 26B, 26C, and 26D are methods of performing a routine for a percussive massage device.
Figure 26B:
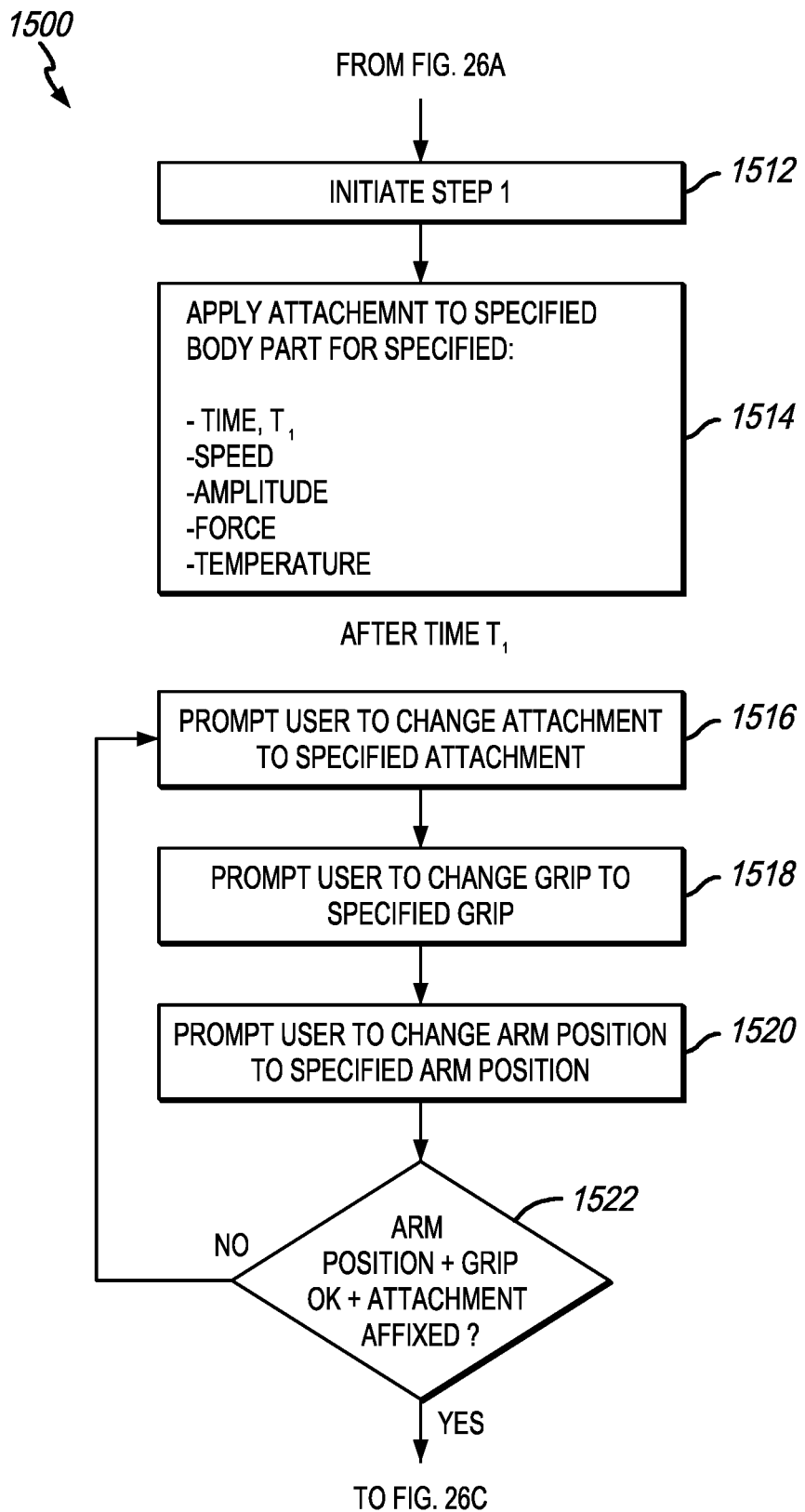
Figure 26C:
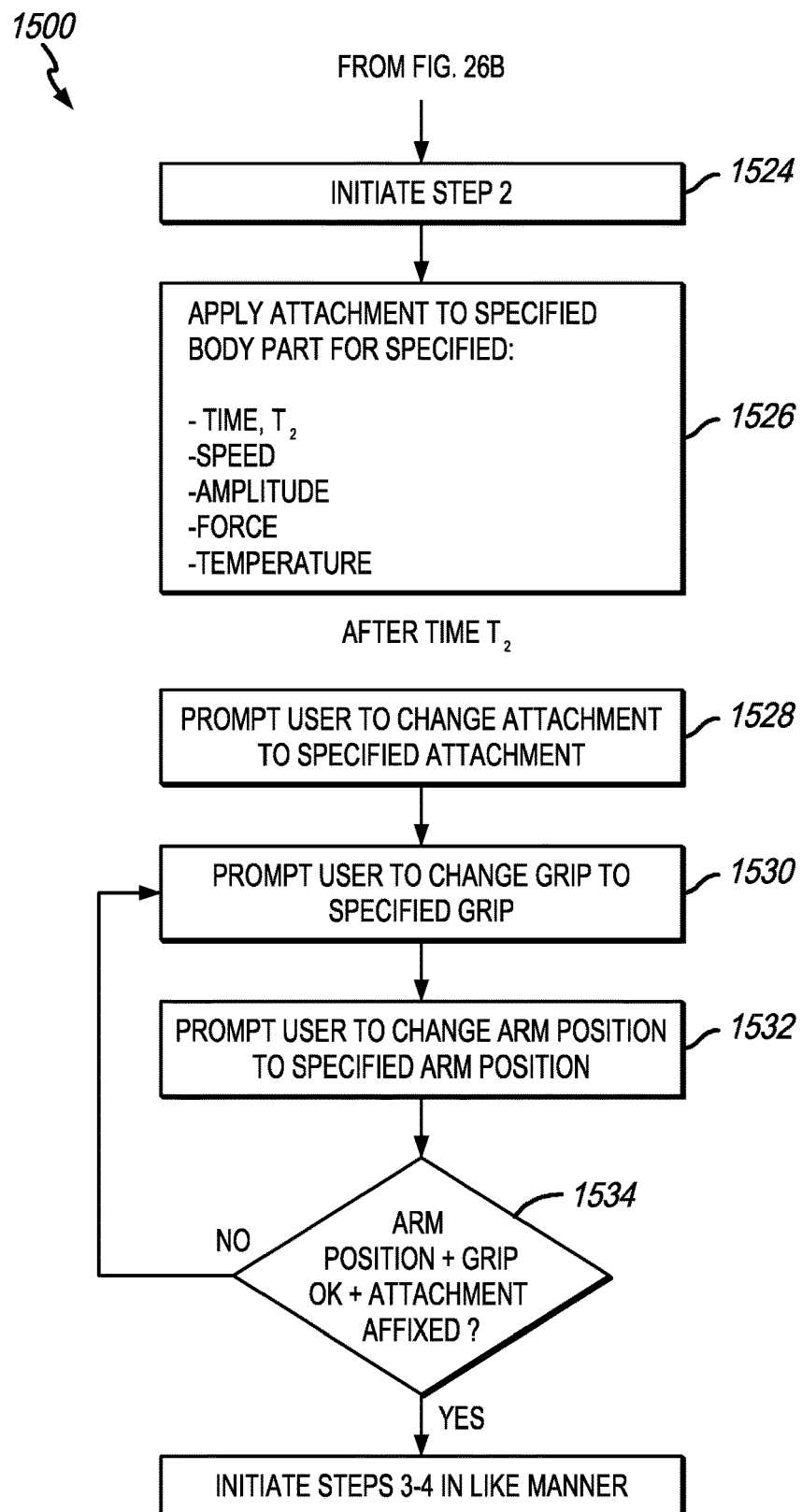

FIGS. 26A-C are a series of flow diagrams showing a method 1500 of executing a routine for a percussive massage device.

FIG. 26A is a flow diagram showing an exemplary protocol initiation. At Step 1502, Protocol 1 is initiated. Protocol 1, for example, is the Protocol 1 depicted in FIG. 24 or the "Shin Splints" Protocol depicted in FIG. 25. One of ordinary skill in the art would understand that Protocol 1 depicted in FIG. 24 does not include all of the outputs that are specified in the Shin Splints Protocol depicted in FIG. 25, and thus, not all steps of the method 1500 apply to the Protocol 1 depicted in FIG. 24.

At Step 1504, a user is prompted to set the arm position to the specified arm position. The user may be the person using the device 400 on their own body or on the body of another person. The arm position specified in the Shin Splints Protocol is arm position 1, for example.

At Step 1506, the user is prompted to use a specified grip or handle portion 143, 145, 147 on the device 400. The grip specified in the Shin Splints Protocol is the third handle portion 147, for example. As described herein, the grip may vary depending on the particular protocol or step.

At Step 1508, the user is prompted to affix a specified attachment to the device 400. As described herein, the attachment may vary depending on the particular protocol or step.

At Step 1510, the method determines whether the arm position and the grip position 143, 145, 147 are configured appropriately and whether the attachment 628 is affixed. Step 1510 may involve a prompt to the user by haptic feedback, application interface, or touch screen (among other types of prompts) in which the user is asked to proceed when the appropriate arm position, grip, and attachment are ready. In other embodiments, the device 400 may sense that the arm position and grip are appropriate and that an attachment is affixed before proceeding automatically. In an embodiment, Step 1510 is repeated until the arm position, grip, and attachment are ready.

FIG. 26B is a flow diagram showing an exemplary Step 1 of the protocol, continuing the method 1500 where FIG. 26A left off.

At Step 1512, Step 1 of the protocol is initiated. Step 1, for example, is Step 1 depicted in FIGS. 24 and 25, for example.

At Step 1514, the method 1500 applies a specified time period ($T_1$) in which the device 400 is activated, a speed of the attachment, an amplitude of the attachment, a force of the attachment, and a temperature of the attachment. In an embodiment, one or more of these outputs of the device 400 are applied. These outputs may be applied by the routine controller 630. One of ordinary skill in the art would understand that a user's implementation of the device 400 on a body part is not required to apply certain of these outputs. For example, the time period, speed, amplitude, and temperature are not necessarily dependent upon a user applying pressure to a body part. On the other hand, the force applied by the attachment 628 may require a user to exert pressure on a body part for a target force (or a target force range) to be reached. Further, the temperature may vary depending on whether the attachment 628 is applied to a body part, or not, and to which body part it is applied. Thus, the temperature may need to be adjusted during application of the attachment 628 to reach a desired temperature predetermined by the protocol. In another embodiment, the temperature may be adjusted by a user.

After time period $T_1$, the user may be prompted to change the attachment 628, arm position, and/or grip position 143, 145, 147. These outputs may need to be implemented prior to the start of Step 2 of a protocol. In the Shin Splints Protocol depicted in FIG. 25, the attachment 628, arm position and grip position 143, 145, 147 remain the same. At Step 1516, after time period $T_1$, the user is prompted to set the arm position to the specified arm position. The user may be the person using the device 400 on their own body or on the body of another person.

At Step 1518, the user is prompted to use a specified grip 143, 145, 147 on the device 400. As described herein, the grip may vary depending on the particular protocol or step.

At Step 1520, the user is prompted to affix a specified attachment 628 to the device 400. As described herein, the attachment 628 may vary depending on the particular protocol or step.

At Step 1522, the method determines whether the arm position and the grip position 143, 145, 147 are configured appropriately and whether the attachment 628 is affixed. This step and all other like steps are optional. Step 1510 may involve a prompt to the user by haptic feedback, application interface, or touch screen (among other types of prompts) in which the user is prompted to move to the next step in the routine and/or requested to proceed when the appropriate arm position, grip, and attachment are ready. In other embodiments, the device 400 may sense that the arm position and grip are appropriate and that an attachment is affixed before proceeding automatically. In an embodiment, Step 1522 is repeated until the arm position, grip, and attachment are ready.

FIG. 26C is a flow diagram showing an exemplary Step 2 of the protocol, continuing the method 1500 where FIG. 26B left off.

At Step 1524, Step 2 of the protocol is initiated. Step 2, for example, is Step 2 depicted in FIGS. 44 and 45, for example.

At Step 1526, the method 1500 applies a specified time period ($T_2$) in which the device 400 is activated, a speed of the attachment, an amplitude of the attachment, a force of the attachment, and a temperature of the attachment. In an embodiment, one or more of these outputs of the device 400 are applied. These outputs may be applied by the routine controller 630. One of ordinary skill in the art would understand that a user's implementation of the device 400 on a body part is not required to apply certain of these outputs. For example, the time period, speed, amplitude, and temperature are not necessarily dependent upon a user applying pressure to a body part. On the other hand, the force applied by the attachment 628 may require a user to exert pressure on a body part for a target force to be reached. Further, the temperature may vary depending on whether the attachment 628 is applied to a body part, or not, and to which body part it is applied. Thus, the temperature may need to be adjusted during application of the attachment 628 to reach a desired temperature predetermined by the protocol. In another embodiment, the temperature may be adjusted by a user.

After time period $T_2$, the user may be prompted to change the attachment 628, arm position and/or grip position 143, 145, 147. These outputs may need to be implemented prior to the start of Step 3 of a protocol. In the Shin Splints Protocol depicted in FIG. 25, the attachment 628 and arm position remain the same, but the grip 143, 145, 147 is adjusted to the base grip. At Step 1528, after time period $T_2$, the user is prompted to set the arm position to the specified arm position. The user may be the person using the device 400 on their own body or on the body of another person.

At Steps 1528-1534, therefore, steps substantially the same as Steps 1516-1522 are performed. After Step 1534, Steps 3-4 are initiated in substantially the same manner as Steps 1-2. For example, Steps 3 and 4 may be Steps 3 and 4 of the Protocol 1 depicted in FIG. 24 or the Shin Splints Protocol depicted in FIG. 25. Furthermore, Step 1534 can be omitted in a device where none of the grip, arm position or attachment can be sensed by the device. In this embodiment, the given protocol simply moves from step 1 to step 2 prompting the user to make a change (but regardless of whether the user has actually made a change).

Figure 26D:
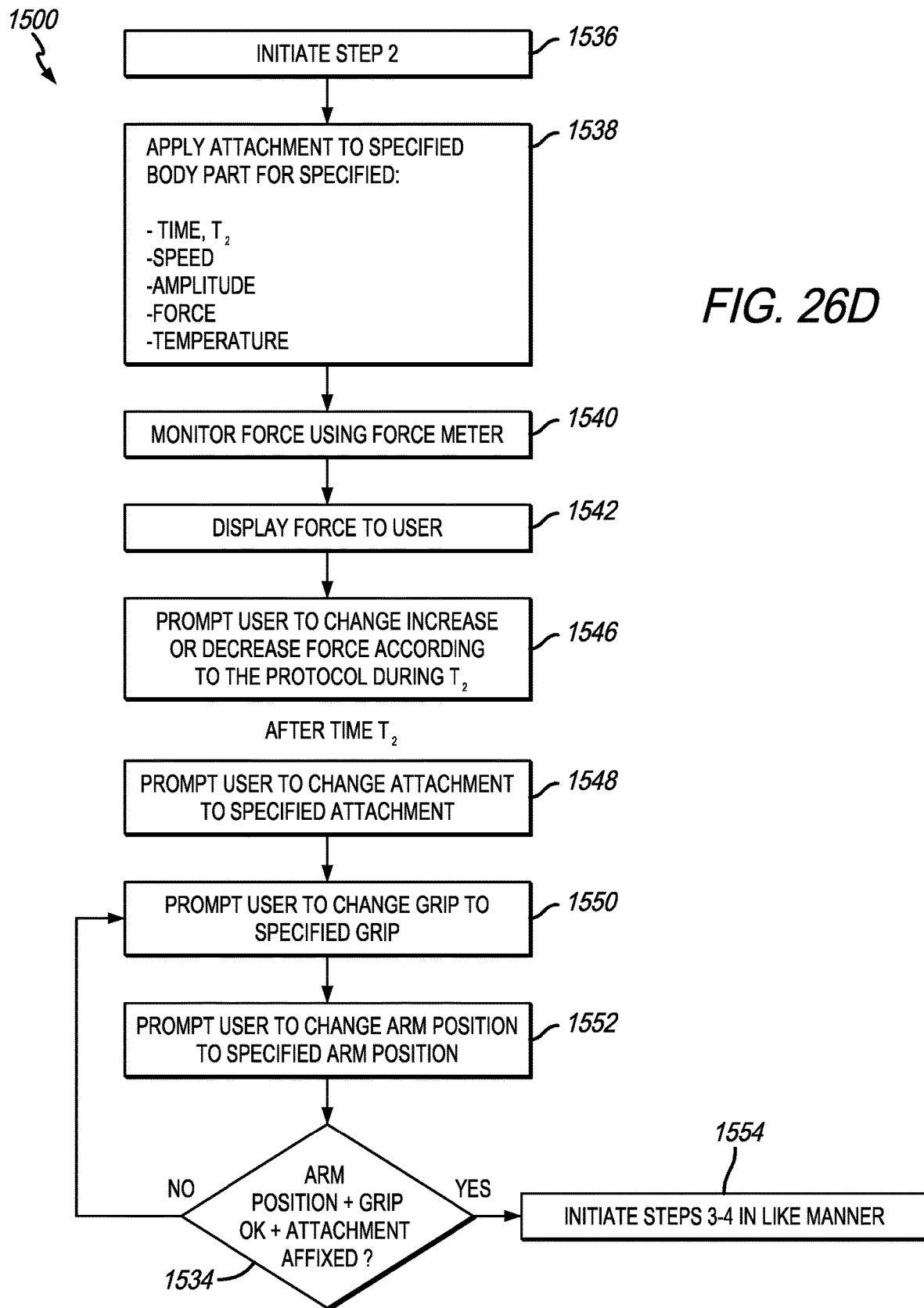

As an alternative to FIG. 26C, FIG. 26D is a flow diagram depicting an alternative Step 2 of a protocol. In the alternative Step 2, a force meter adjustment is implemented.

Steps 1536-1538 are performed substantially the same as Steps 1524-1526 in previous Step 2 above.

At Step 1540, the force being applied by the attachment 628 is monitored. In the embodiment shown in FIG. 26D, the method 1500 utilizes the force meter 400 to monitor the force actually being applied by the user.

At Step 1542, the force is displayed to the user. In an embodiment, the force is displayed on an application interface 1584 such as a graphical user interface. In other embodiments, individual use or combined use of the application interface 1584, touch screen 1582, the OLED screen 711, or the like, may be used to display the force.

Figure 28:
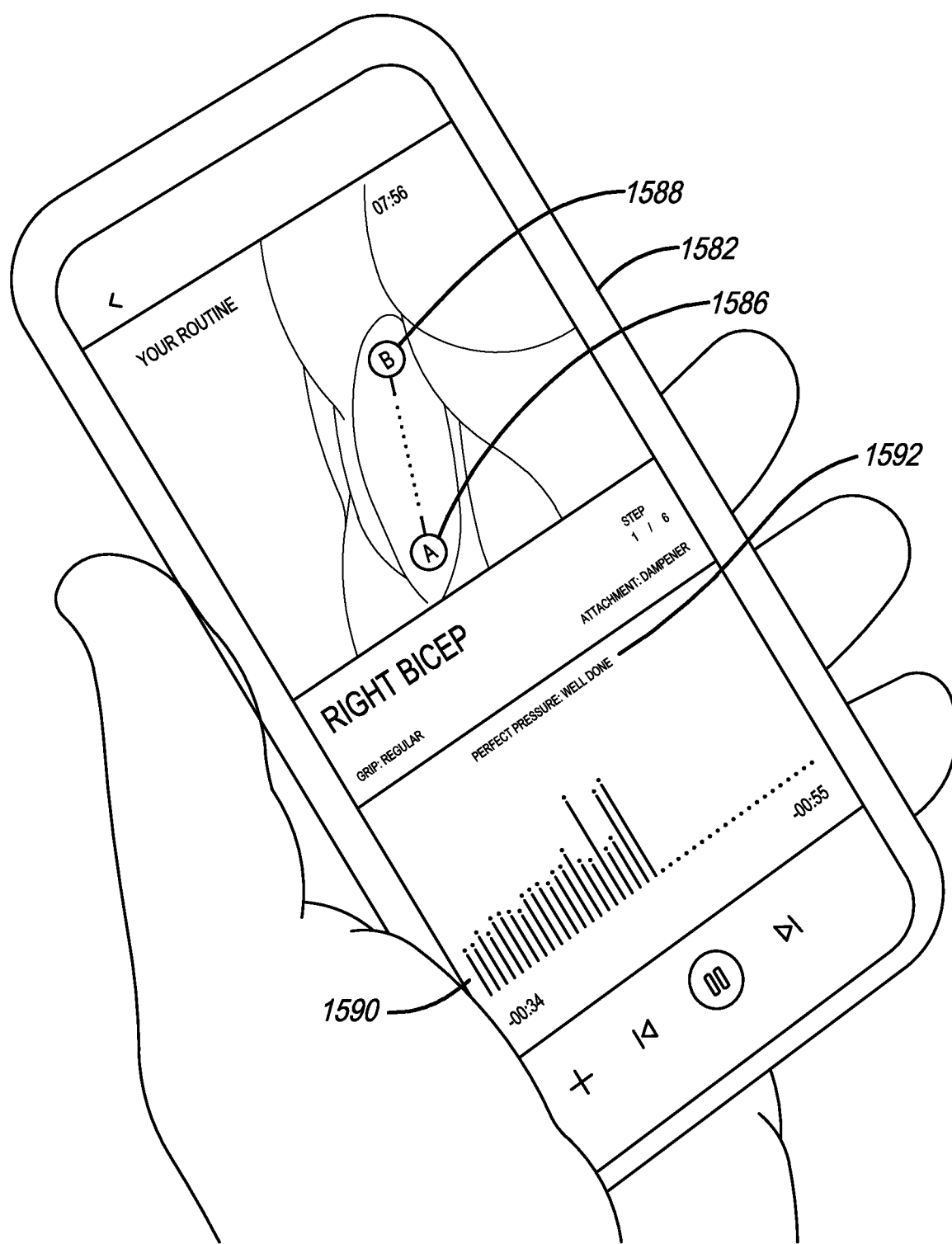
FIG. 28 is a front view of a graphical user interface showing a "Right Bicep" protocol.

At Step 1546, the user is prompted to increase or decrease the force being applied to a body part according to the specified protocol during $T_2$. FIG. 28 is a diagram showing a touch screen 1582 in accordance with an exemplary embodiment of the display of the force. A force display 1590 shows an exemplary embodiment of Step 1546. The force display 1590 shows a series of force measurements over the course of the "Right Bicep" step of a protocol. A force display prompt 1592 is used to display a message to the user such as "PERFECT PRESSURE: WELL DONE" when the force applied by the attachment 628 matches or corresponds to a target force predetermined by the protocol. In this embodiment, the force display prompt 1592 may recite "INCREASE PRESSURE" or the like if the measured force applied by the attachment 628 is lower than the target force predetermined by the protocol. Consequently, if the measured force applied by the attachment 628 is higher than the target force predetermined by the protocol, then the force display prompt 1592 may recite "DECREASE PRESSURE" or the like. The user may then adjust the pressure the user is exerting on the body part to either increase pressure or decrease pressure according to the force display prompt 1592 so that the measured force is equivalent or substantially equivalent to the target force.

After time period $T_2$, the user may be prompted to change the attachment 628, arm position and/or grip position 143, 145, 147. These outputs may need to be implemented prior to the start of Step 3 of a protocol. In the Shin Splints Protocol depicted in FIG. 25, the attachment 628 and arm position remain the same, but the grip 143, 145, 147 is adjusted to the base grip. At Step 1528, after time period $T_2$, the user is prompted to set the arm position to the specified arm position. The user may be the person using the device 400 on their own body or on the body of another person.

At Steps 1548-1552, therefore, steps substantially the same as Steps 1516-1522 are performed. After Step 1534, Steps 3-4 are initiated in substantially the same manner as Steps 1-2. For example, Steps 3 and 4 may be Steps 3 and 4 of the Protocol 1 depicted in FIG. 24 or the Shin Splints Protocol depicted in FIG. 25.

Figure 27:
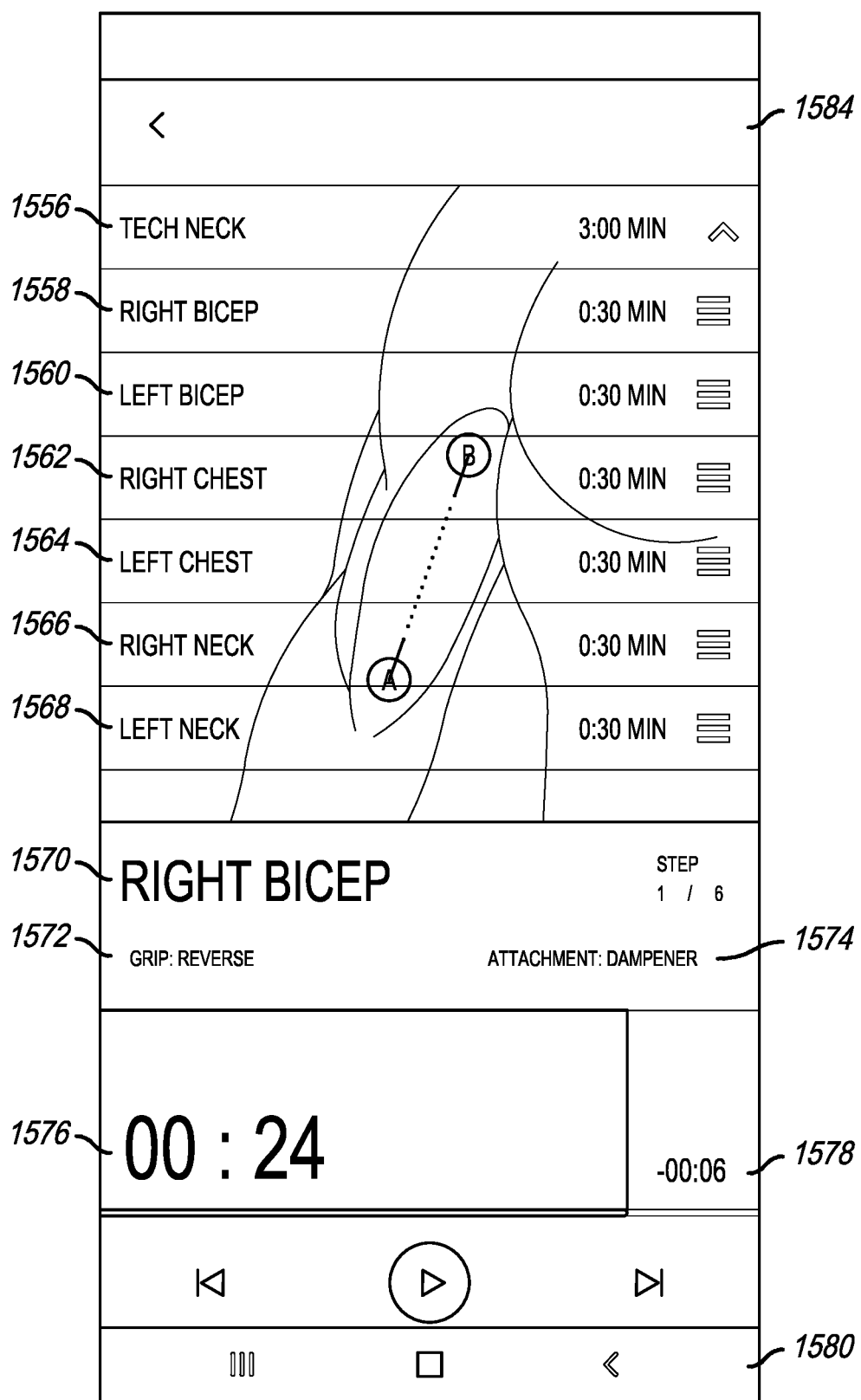
FIG. 27 is a front view of a graphical user interface showing a "Right Bicep" protocol.

FIG. 27 is a diagram in accordance with an exemplary embodiment of an application interface 1584. At the top of the interface 1584, a protocol field 1556 is displayed to the user. In this embodiment, the protocol field 1556 is "TECH NECK." The protocol title 1556 also shows the overall time period of the protocol.

The next portion of the interface 1584 shows step fields 1558-1568 of the protocol that are displayed to the user. In this embodiment, the step fields identify the title of the step and time period of the step. For example, step field 1558 is titled "RIGHT BICEP" (where the treatment will be provided) and the time period of activation is "0:30 MIN."

The interface 1584 also includes a current step field 1570 that identifies the current step title 1570, a grip title display 1572, and an attachment title display 1574.

The interface 1584 also includes a time display 1576 and a time remaining display 1578 to show the user how much time has occurred during that step and the time remaining in that step. Finally, the interface 1584 includes a control field 1580 to play, skip back, and skip forward from step to step.

As described above, FIG. 28 shows a touch screen 1582 on a mobile device. The touch screen 1582 displays a graphic depicting a starting point 1586 "A" and an end point 1588 "B" (thereby defining a treatment path) showing the user where to apply the attachment 628 to the specified body part. In FIG. 27, the display instructs the user to move the attachment from the lower portion of the right bicep to the upper portion of the right bicep (the treatment path) during the current step. In some embodiments, during a single step, the user may be prompted or shown on the graphical user interface more than one treatment path (or a first treatment path and a second treatment path) on the same body part/muscle or on different body parts/muscles. For example, during the right bicep step, the user may be prompted to first move the device along the path shown in FIG. 28, but, during the same thirty second step may also be prompted or shown a path that is parallel to the path shown in FIG. 28.

Figure 29:
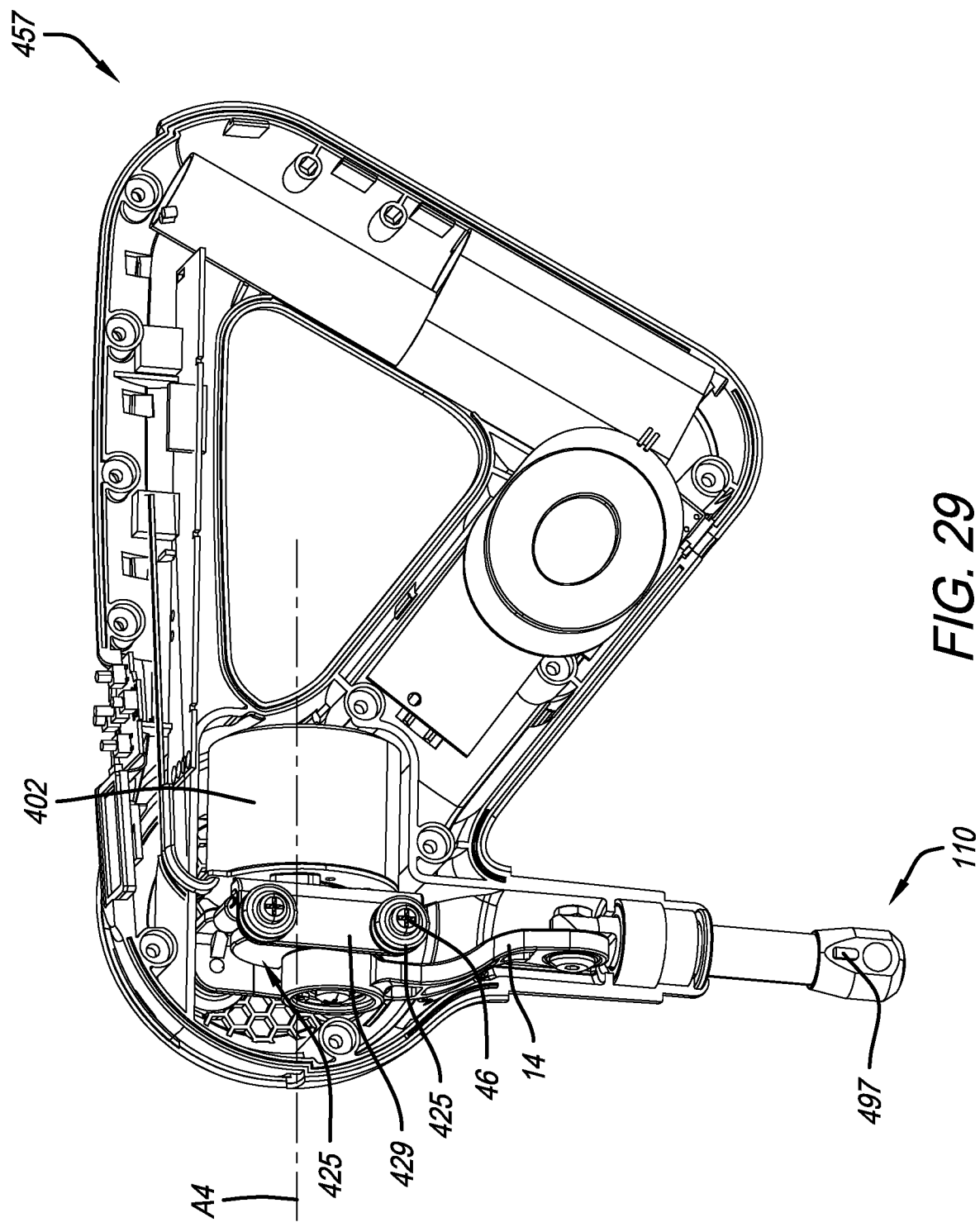
FIG. 29 is perspective view of a percussive massage device with a portion of the housing removed and showing the motor mount orienting the motor shaft axis extending longitudinally.
Figure 30:
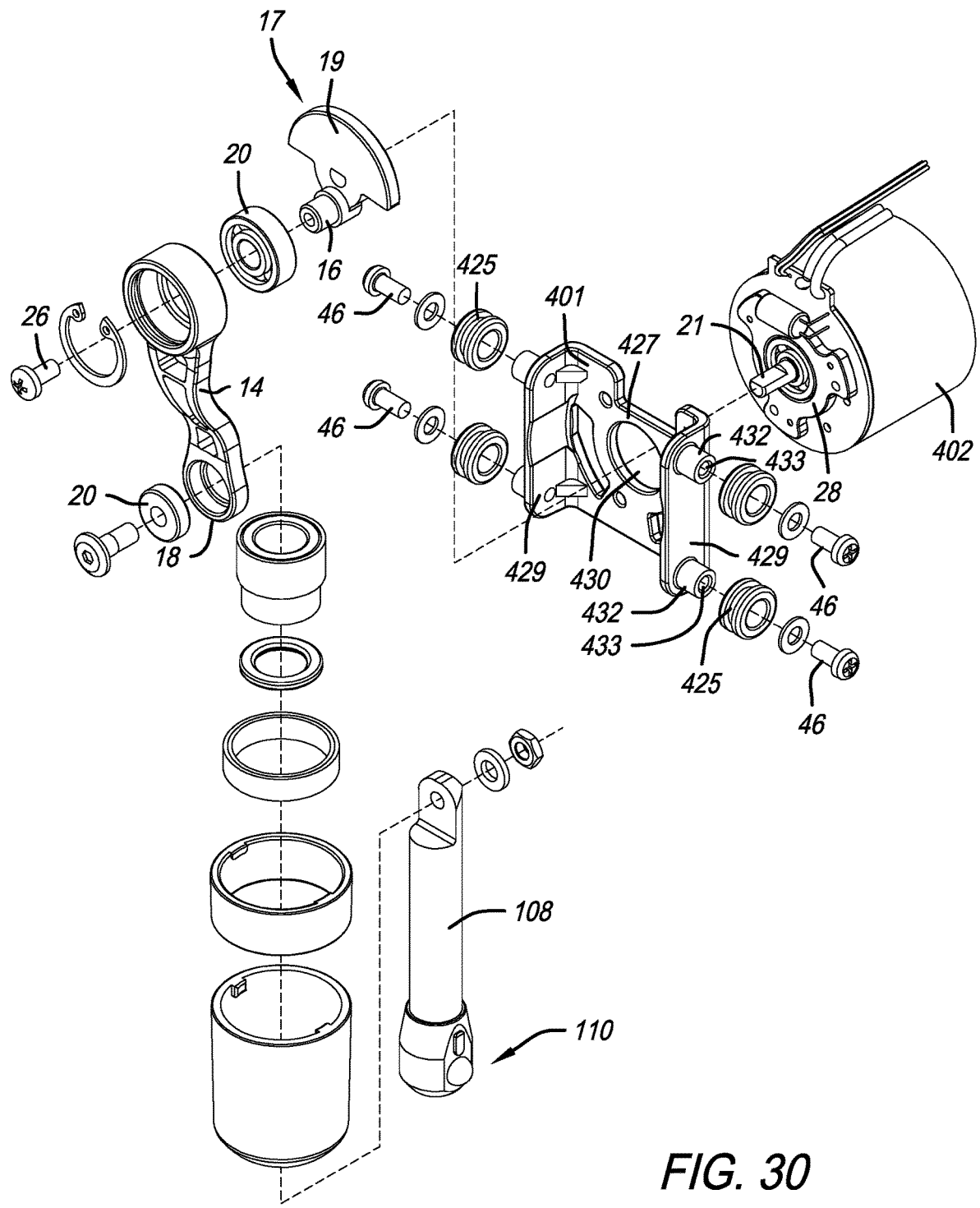
FIG. 30 is an exploded perspective view of the motor mount, motor and other components from FIG. 29.
Figure 31:
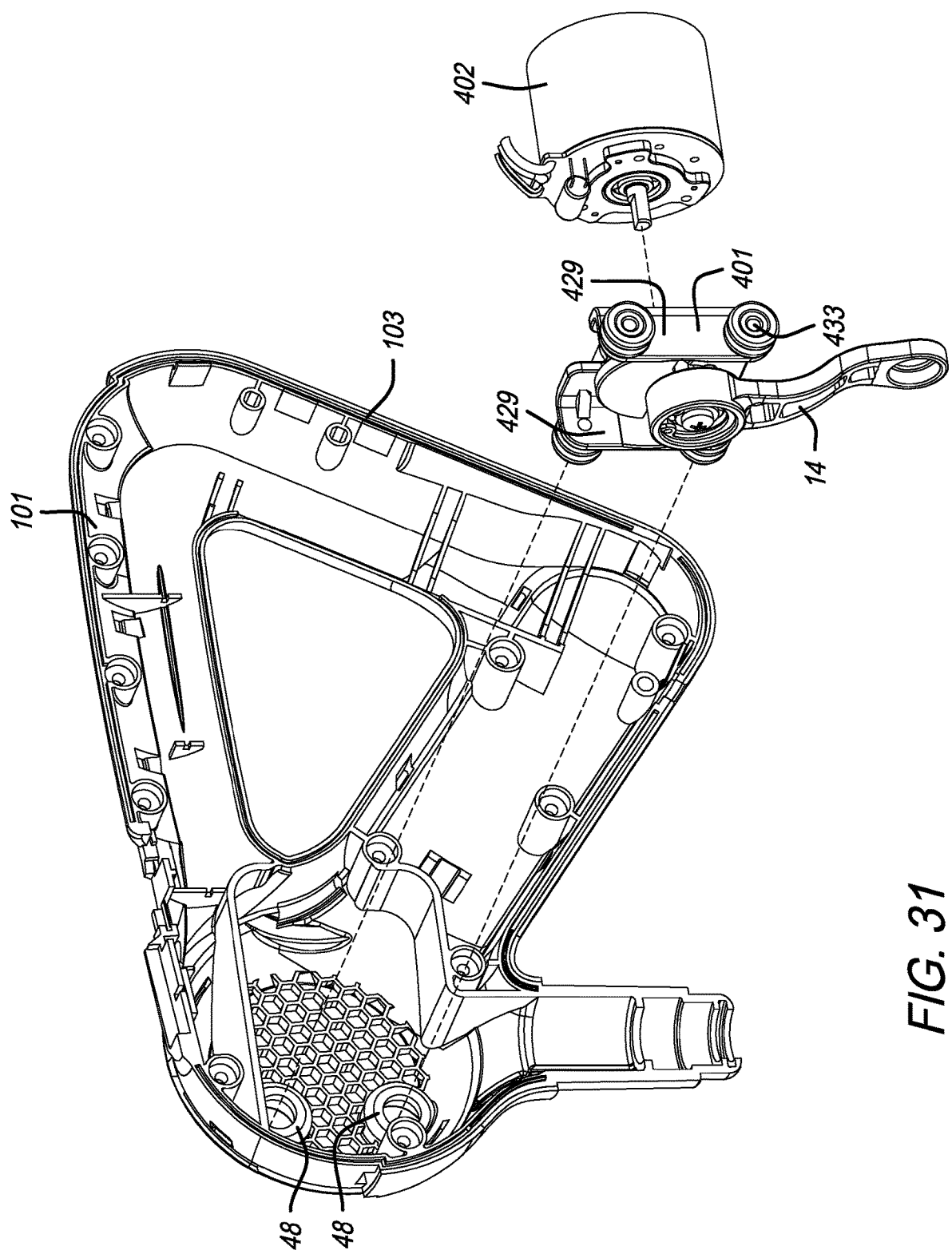
FIG. 31 is a perspective view showing the motor and motor mount exploded out of the housing.
Figure 32:
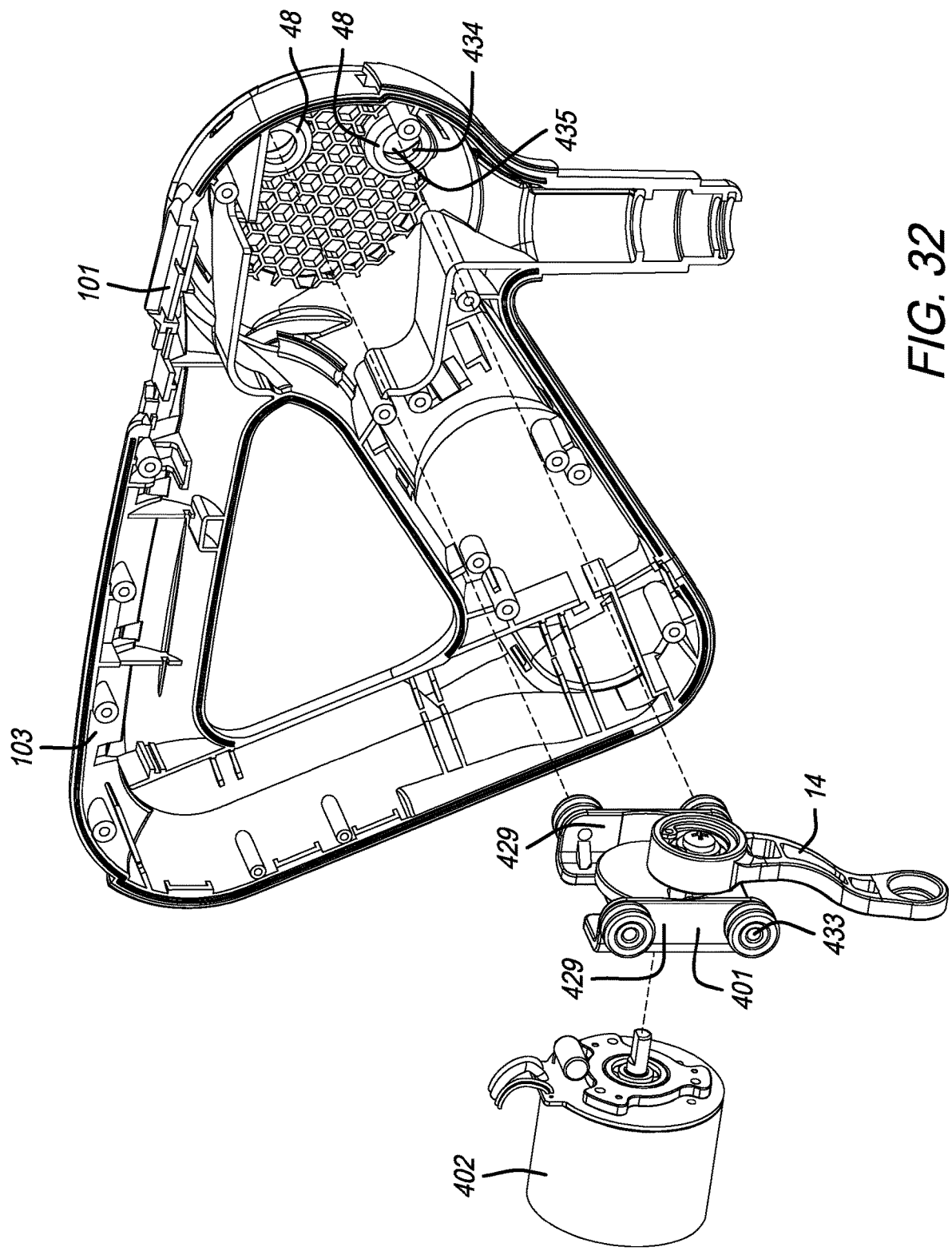
FIG. 32 is a perspective view showing the motor and motor mount exploded out of the housing on the opposite side as FIG. 31.
Figure 33:
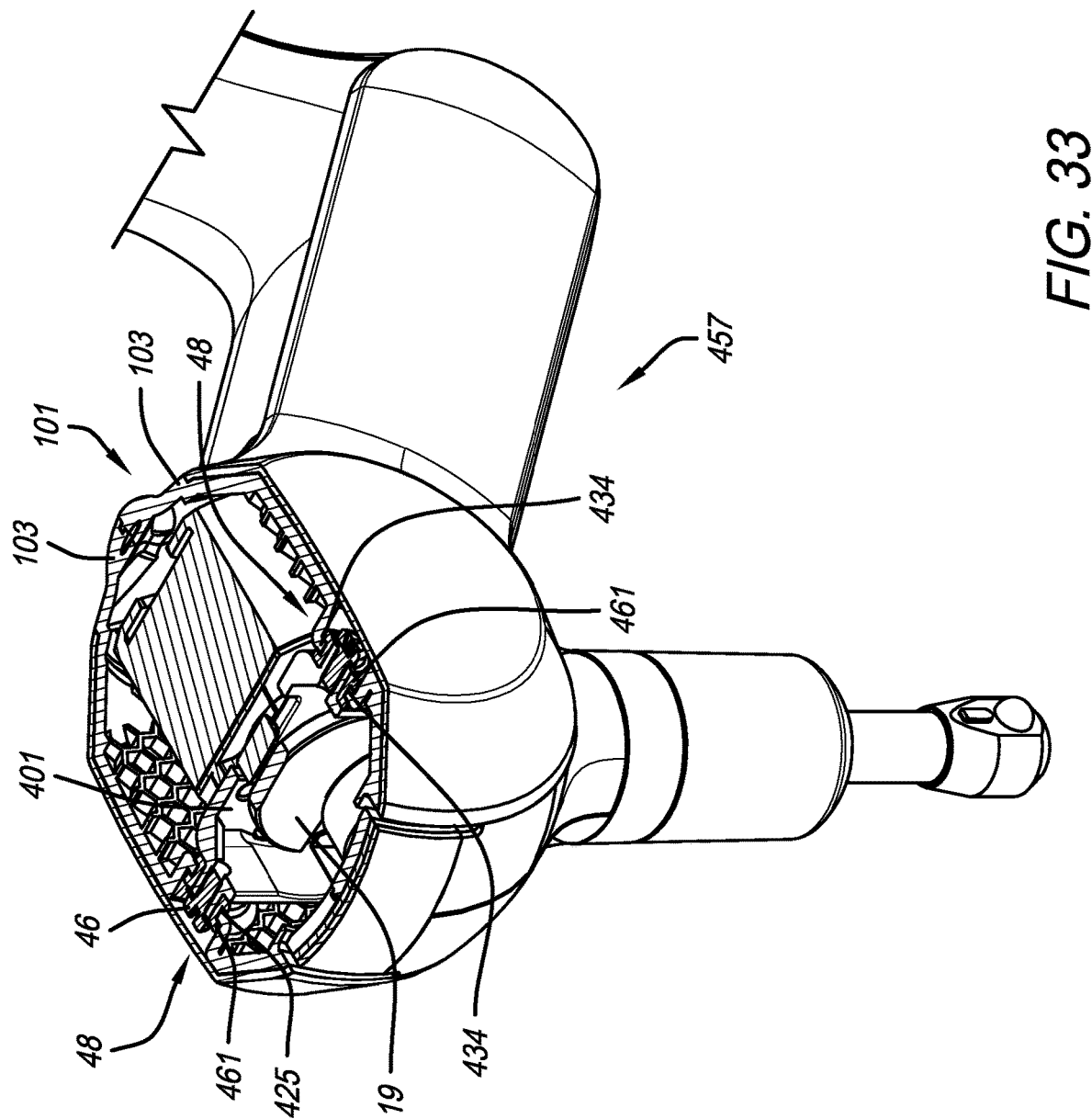
FIG. 33 is a cross-sectional perspective view.

FIGS. 29-33 show a device 457 similar to device 400 described above. However, the motor 402 is oriented differently (the motor shaft axis A4 extends perpendicular to the motor shaft axis in device 400), as shown in FIG. 29. It will be appreciated that all embodiments discussed herein or shown in different drawings are interchangeable and the components or inventive concepts in one embodiment can be substituted with or into components or inventive concepts in other embodiments. All parts in all embodiments are optional and are interchangeable or usable with parts from or with other embodiments. As shown in FIG. 30, the motor mount 401 includes a mounting wall 427 with first and second mounting flanges 429 extending therefrom and a shaft opening 430 defined therein. The boss members 432 include a threaded opening 433 defined therein. The boss members 432 receive cylindrical dampening feet 461 with annular slots 425 defined therein on the outside thereof and threaded fasteners 46 in the threaded openings 433. As shown in FIGS. 31-33, the motor mount 401 attaches to both housing halves 103 of the housing 101. The mounting members 48, which are essentially an inwardly extending ring are received in annular slots 425 of the cylindrical dampening members 461. In other words, the cylindrical dampening members 461 are received in the opening 435 of mounting members 48 and the ring portion 434 of the mounting members 48 is received in the annular slots 425. The threaded fasteners 46 extend through the central openings of the cylindrical dampening members 461 (and the openings in the mounting members 48) and are threaded into the threaded openings 433 in the boss members 432. This secures the motor mount 401 to the housing halves 103 and the housing 101. The cylindrical dampening members are made of rubber or the like and help reduce vibrations.

Furthermore, the motor mount 401 mounts the motor 402 so that the motor shaft axis A4 (the rotation axis), extends forwardly and backwardly with respect to the orientation of the device 457 in use. This direction is also considered longitudinally. The motor shaft axis A4 (or a plane defined by the motor shaft axis) bisects the housing 101.

Figure 34:
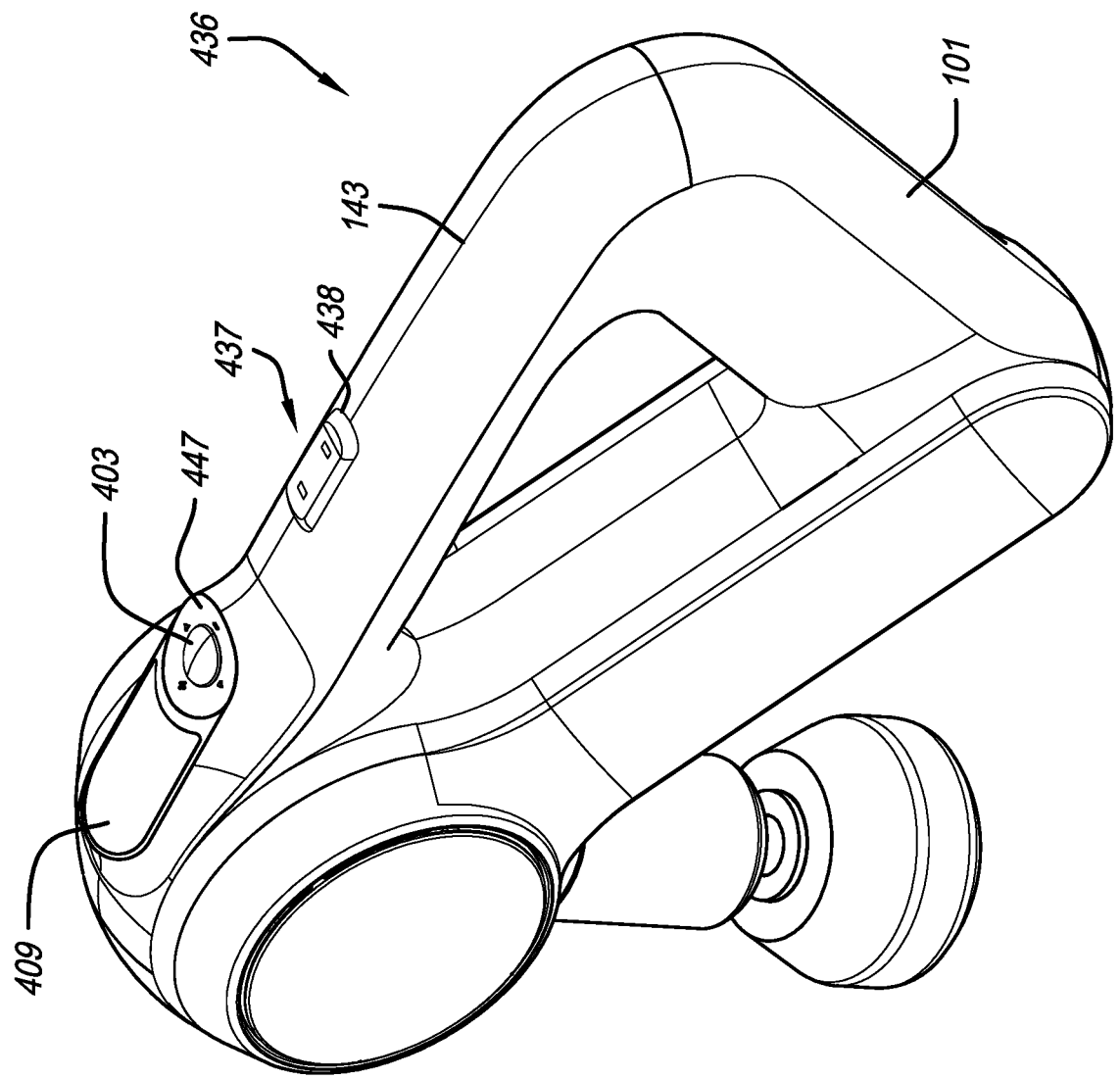
FIG. 34 is a perspective view of a percussive massage device that includes a heart rate monitor.
Figure 35:
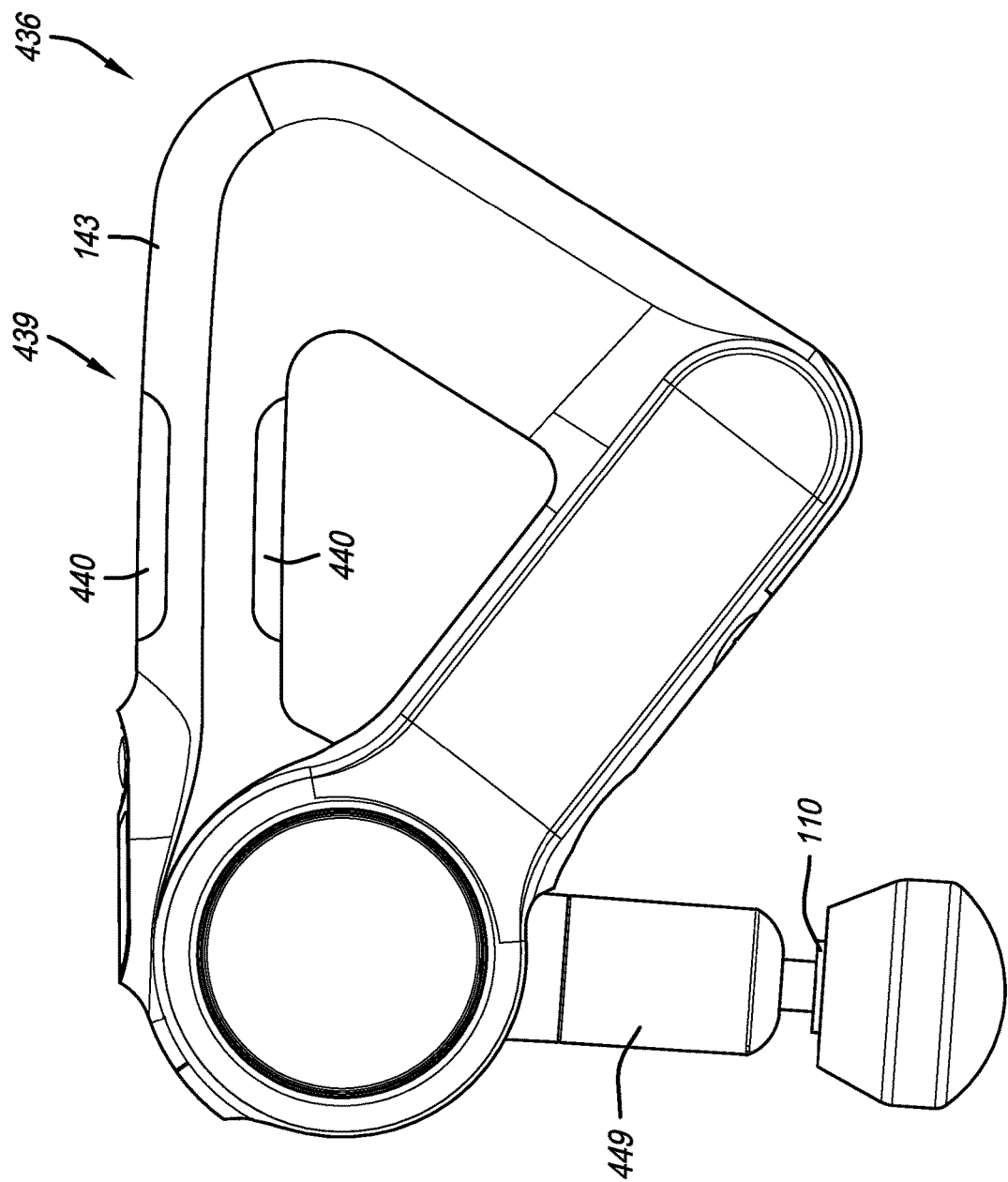
FIG. 35 is a perspective view of a percussive massage device that includes a heart rate monitor with first and second pulse contacts.
Figure 36:
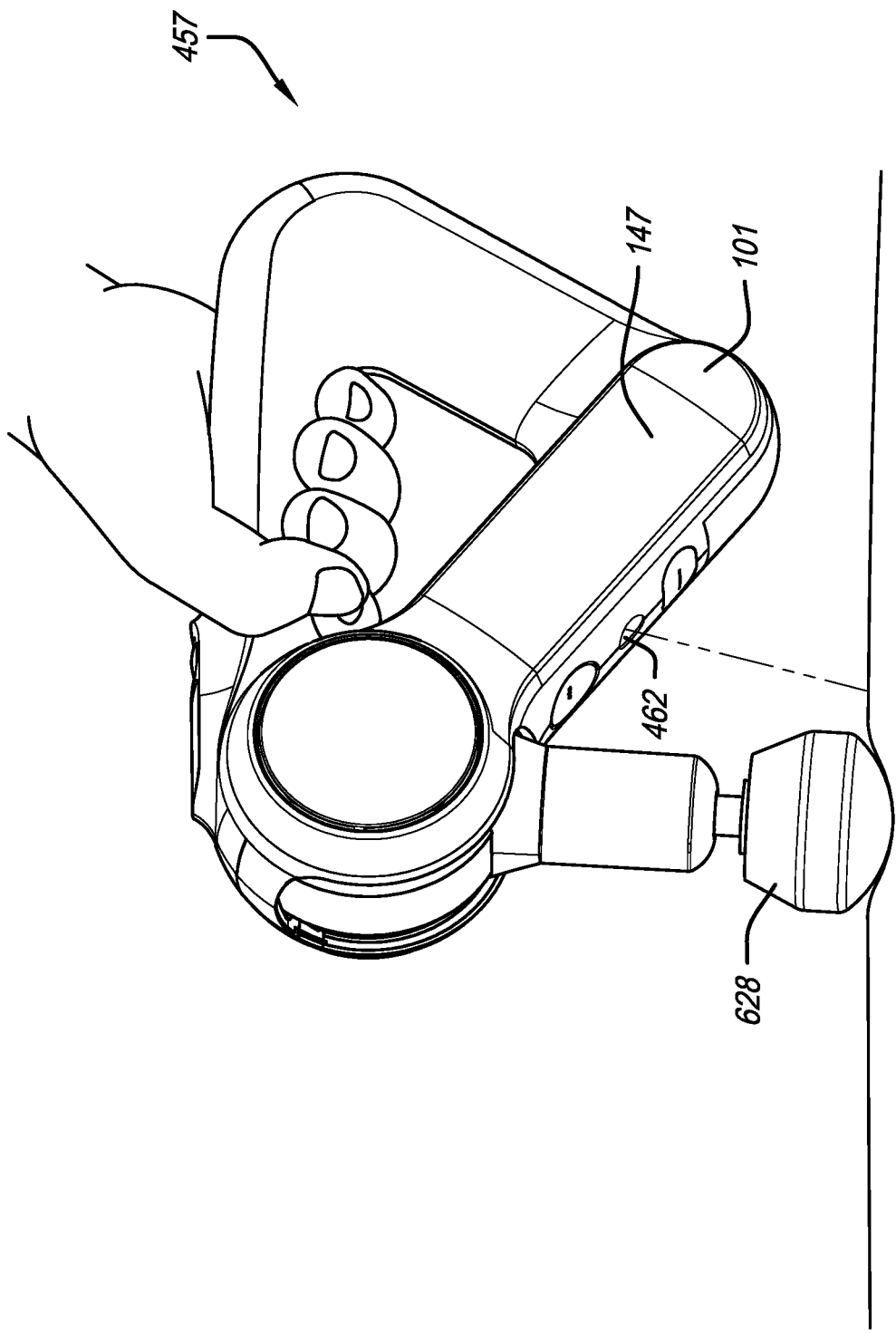
FIG. 36 is a perspective view of a percussive massage device that includes a temperature sensor or monitor.

FIGS. 34-36 show another embodiment where the percussive massage device 436 includes a heart rate sensor 437 that is located on the top handle or first handle portion 143 of the device. Any type of heart rate sensor is within the scope of the invention. Heart rate sensor 437 is a hear rate sensor that uses infrared to measure and record heart rate and can also measure and record heart rate variability, if desired. In an exemplary use, heart rate is measured using a process called photoplethysmography or PPG. This involves shining a specific wavelength of light, which usually appears green, from a pulse oximeter sensor on the underside or upper side (e.g., top of the first handle portion) of the device where it touches the skin. As the light illuminates the tissue, the pulse oximeter measures changes in light absorption and the device then uses this data to generate a heart rate measurement. The electronics associated with heart rate sensor 437 are included in the housing 101 and can be separate or on the main PCB. The screen 409 displays the heart rate data. A heart rate monitor opening 438 is defined in the housing and the heart rate sensor 437 is mounted therein, as shown in FIG. 34.

FIG. 35 shows another type of heart rate monitor or sensor 439 that can be utilized and includes first and second pulse sensors or contacts 440. A first pulse sensor is positioned so that it contacts the user's palm in use and the second pulse sensor is positioned so that it contacts the user's fingers in use. The first handle portion 143 can also include an indent where the contact is located so the user knows where to place their index finger. Other sensors, actuators or components that provide an active effect that can be included on the handle portions include other global biometric sensors, such as those that can sense or determine heart rate variability, $SPO_2$ (peripheral capillary oxygen saturation) and/or respiratory rate. It will be appreciated that the any of the sensors, actuators or components discussed herein that provide an active effect can be positioned on any of the first, second and/or third handle portions or on all three handle portions.

Figure 36A:
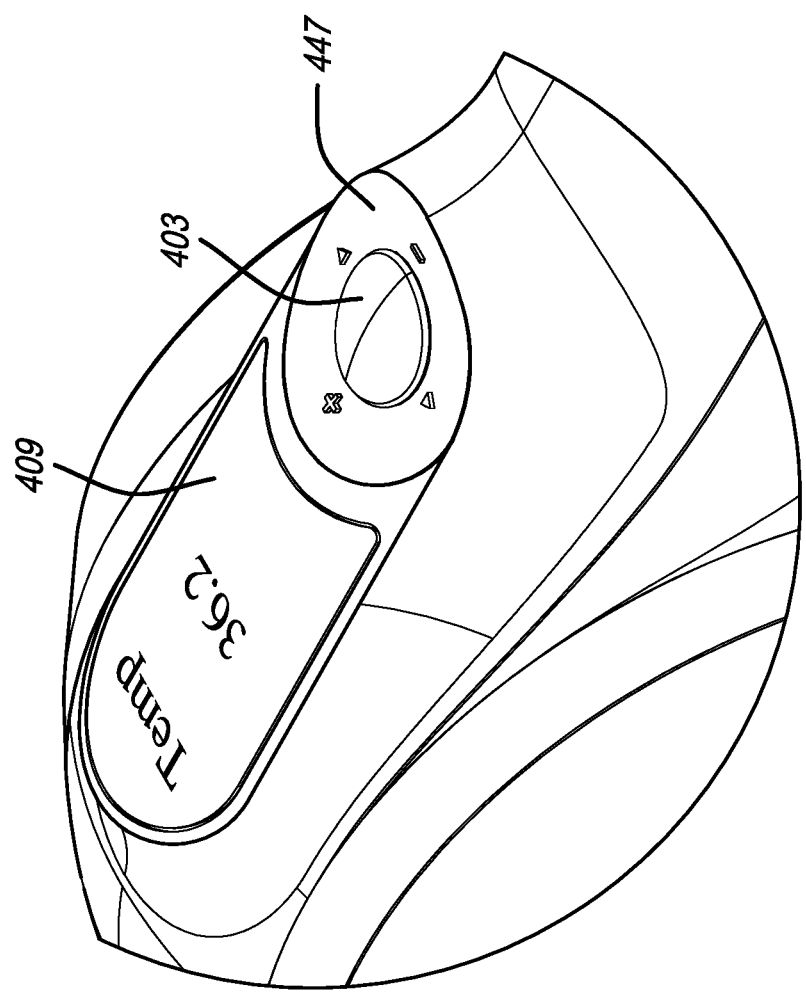
FIG. 36A is a detailed view of the temperature reading on the screen taken from FIG. 34.

FIGS. 36 and 36A show device 457 including a thermal sensor 462. Any type of thermal sensor is within the scope of the invention. In the embodiment of FIG. 34, the thermal sensor 462 is an infrared thermometer module installed in the housing 101 of the device (shown in a non-limiting position in FIG. 36 on the third handle portion 147) that allows the user to measure the temperature of the user's muscles or other body part. FIG. 36A shows the temperature readout on the screen 409. The thermal sensor 462 is preferably in data and/or electrical communication with the PCB. The temperature data can also be communicated to the app. In an infrared thermometer, infrared light is focused on the body part to be measured or to be treated or while being treated and the infrared thermometer module measures energy or radiation coming from the surface. The detector then translates the amount of electricity generated into a temperature reading of the particular muscle, body part, etc. The infrared beam (see FIG. 36) is emitted through an opening in the third handle portion 147 of the housing 101 and the module is mounted within the housing.

In a preferred embodiment, the temperature reading capability is integrated with and a part of the treatment routines or protocols described herein. For example, instead of a routine or a step within a routine running or extending for a predetermined period of time, the routine or step (i.e., the amount of time a particular muscle or body part is treated or targeted) can extend until the muscle or body part (referred to generally herein as a body part) reaches a predetermined temperature. Accordingly, reaching a predetermined temperature can be substituted for predetermined period of time for any of the routines discussed herein. For example, step 1526 in FIG. 26C can be substituted with the method 1500 applies the device 400 is activated until a specified temperature is reached. This can be used to be sure that a body part has been warmed up properly prior to exercise. Therefore, in use, the temperature will rise from a starting temperature to a predetermined finishing temperature and the routine can then go to the next step or end. There also may be a number of "temperature steps" that are each part of the a routine. For example, in the first step, the muscle may go from the starting temperature and move to a second temperature. The next step may treatment and temperature reading from the second temperature to a higher third temperature. The temperature range between the starting and the finish temperature within the routine may also be different for each user. Furthermore, haptic feedback or other notification or instructions can be provided to let the user know when the finish temperature or predetermined temperature has been reached and they can move to the next step in the routine.

As shown in FIG. 34, in a preferred embodiment, the device 400 includes screen 409, which may or may not be a touch screen, as well as button(s) for operating the device. In the embodiment shown in FIG. 34, the device also includes a center button 403 for turning the device on and off and a ring/rocker button 447 that provides the ability to scroll left and right (e.g., to the preset treatments discussed herein) and up and down (e.g., to control the speed or frequency).

As shown in FIG. 35, in a preferred embodiment, the arm cover 449 includes a rounded edge or surface to prevent a user's fingers from getting caught therein. and the upper portion of the male connector 110 each include rounded edges As shown in FIG. 29, in a preferred embodiment, the male connector 110 includes an alignment tab 497 above each ball that mates with a slot in the female opening. These tabs 497 help with proper alignment with the treatment structure.

In another preferred embodiment, any of the devices taught herein can include a mechanism for heating or changing the temperature of the attachment (massage element, treatment structure, Ampbit) on the end of the reciprocating shaft. The attachment can include an electrical resistance element therein that is provides to heat to the muscles. In a preferred embodiment, the electrical resistance element is connected to the PCB via a hollow shaft. The two outwardly biased metal spring balls on the male connector act as the electrical connector to the attachment.

Figure 37:
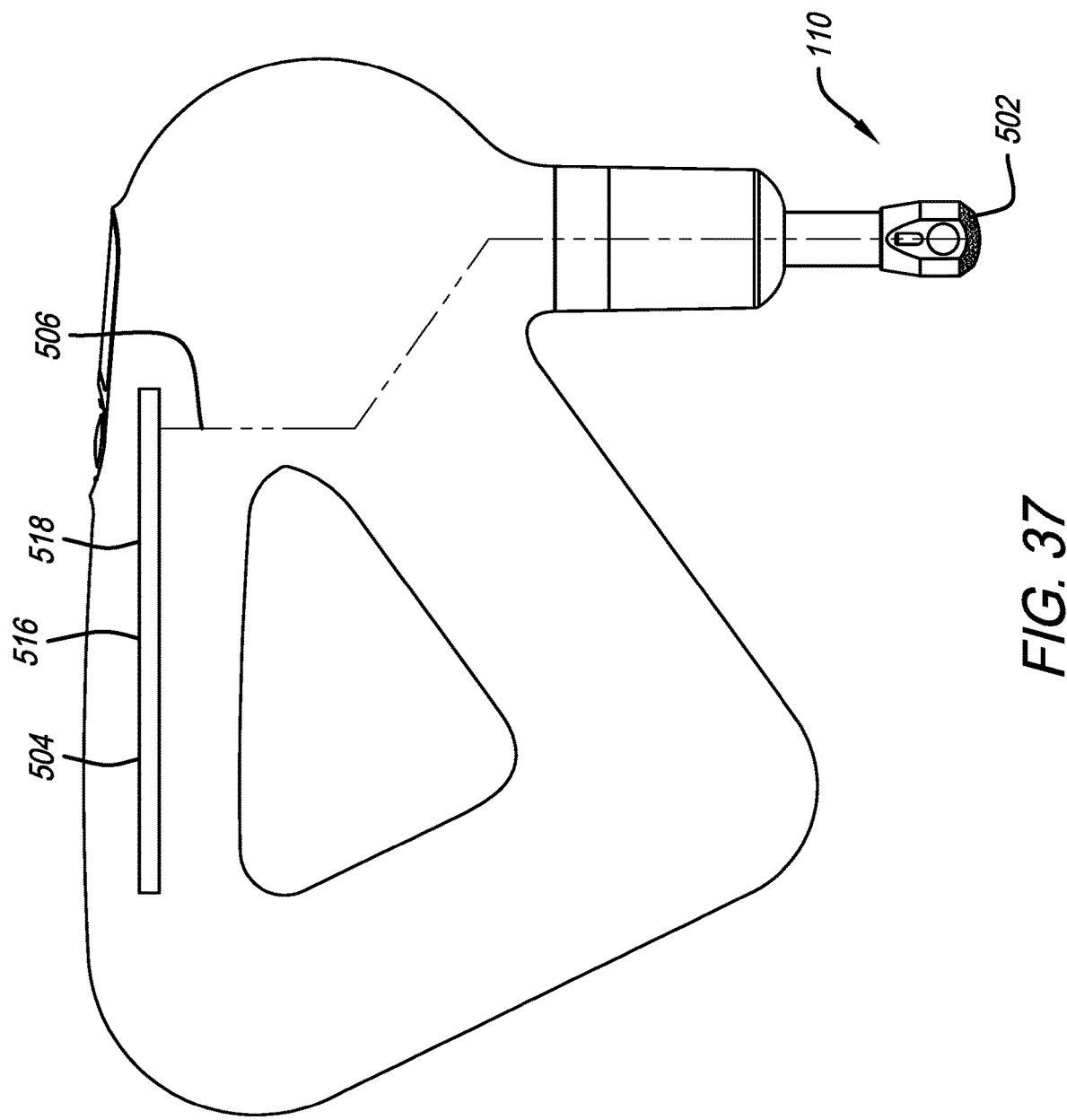
FIG. 37 is a side elevational schematic of a percussive therapy device with a heated male attachment member.

FIGS. 37-40 show embodiments of a percussive massage device that includes a heated massage attachment or massage member. In the embodiment shown in FIG. 37, the male attachment member 110 includes a heating pad or heating element 502 therein. The heating element 502 is preferably electrically connected via electrical wiring 506 or the like to the PCB 504 of the device. Any type of heating is within the scope of the present invention. In a preferred embodiment, the heating element is an electrical resistance member that is located in the end of the male connector 110. In this embodiment, a wire connects the electrical resistance member to the PCB and the battery. The wiring 506 may extend through a hollow shaft or other conduit and is guided through the housing, down the shaft and into the male connector 110. The heating element 502 may be internal within the male connector 110 or may be part of the exterior surface, as shown in FIG. 37. In an embodiment with a female connector on the device (at the end of the shaft), the heating element can be in the female connector. In use, the heated male attachment member transfers heat to the massage member, which heats the outer surface of the massage member, which can then be applied to the user's body part. The PCB can include a controller for controlling the temperature. More than one temperature setting can be provided (e.g., 2-10 settings) so that different temperatures can be utilized by the user as desired. Cooler temperatures can also be provided. The attachment member and the massage member can be made of or partially made of a material that is a good conductor of heat.

Figure 38:
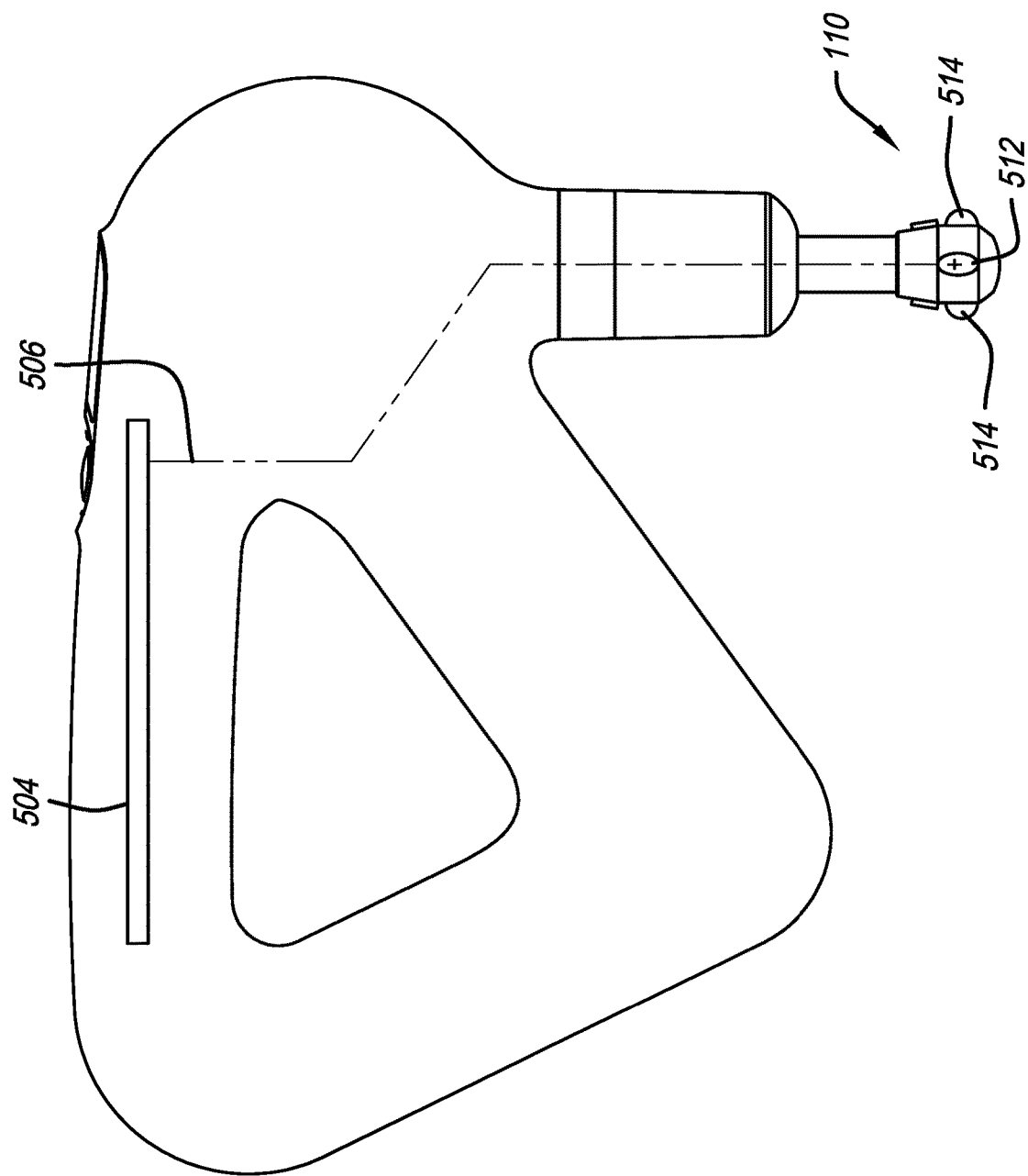
FIG. 38 is a side elevational schematic of a percussive therapy device with a male attachment member with first and second electrical contacts.
Figure 39:
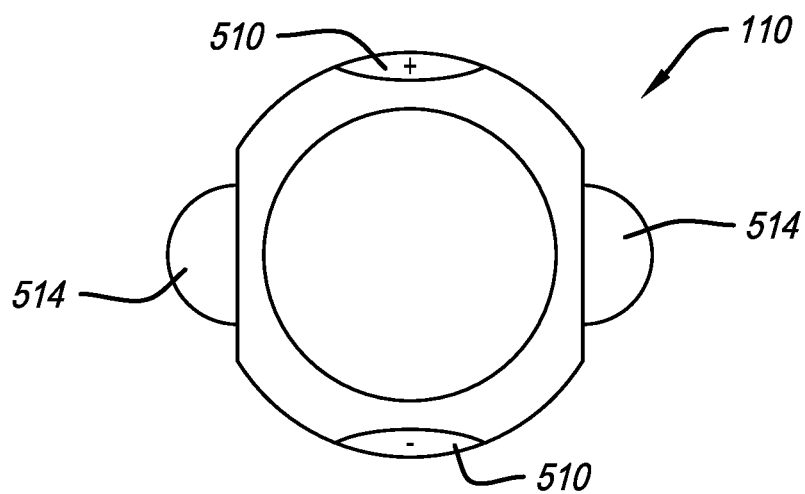
FIG. 39 is a bottom view of male attachment member with first and second electrical contacts.
Figure 40:
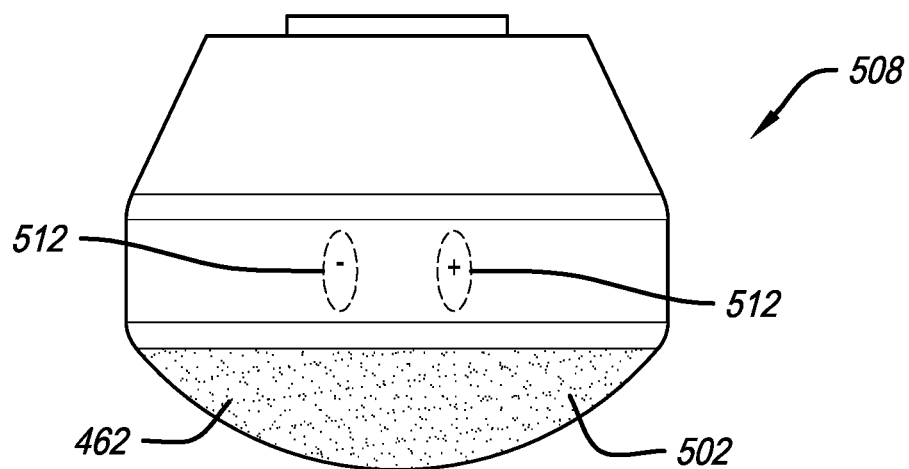
FIG. 40 is a massage member with a heating element therein.

FIGS. 38-40 show another preferred embodiment with a heated or temperature controlled massage member 508. All disclosure related to the FIG. 37 embodiment is repeated for this embodiment. In this embodiment, the female or male attachment member 110 is electrically connected to the complementary male or female attachment member in the massage member to provide power to heat or cool the massage member 508. FIG. 38 shows the device with power running from the PCB 504 to the male attachment member 110. As shown in FIG. 39, the male attachment member 110 includes positive and negative electrical contacts 510 that mate with opposing positive and negative electrical contacts 512 in the female attachment member in the massage member 508, as shown in FIG. 40. FIG. 39 shows a male attachment member with metal balls 514 that are received in indentations in the female attachment member. The metal balls 514 can be the electrical contacts 510 and the electrical contacts 512 can be positioned in the indentations in the female attachment member. The heating element 502 may be internal within the massage member 508 or may be part of the exterior surface.

In use, an electrical connection is made when the massage member 508 is secured to the device and to the male attachment member 110. When heating or cooling is turned on, the heating element 502 in the massage member 508 is heated, which can then be applied to the user's body part. The heating element or electrical resistance member (e.g., heated pad) can be located in or on the massage member (e.g., ball, cone, etc.) and the metal connection between the male connector and the massage member is used to electrically connect to the battery.

The electrical connection between the male or female attachment member 110 permits a variety of uses beyond heating with the heating element 502. In a preferred embodiment, a heating element 502 radiates wavelengths to produce heat on a user's body part. The male or female attachment member 110, for example, may be utilized for a variety of other uses, such as vibration, percussion, cooling, and exfoliating. The male or female attachment member 110 may be configured as an actuator designed to provide these uses. For example, percussion is already achieved using the attachment 628. However, the attachment 628 or 508 may be modified to add or replace the heating element 502 with a cooling, vibration, or exfoliating element. Any of the sensors, actuators or other components that provide an active effect discussed herein can be used on the removable attachment. These can include actuators, local biometric sensors or global biometric sensors, such as heat, cold, light therapy (red, infrared, blue, etc.), electric muscle stimulation (EMS), sensors that sense muscle temperature, muscle oxygen saturation and blood flow, etc. Other uses and actuators may be utilized without departing from the scope of the present invention.

Figure 41:
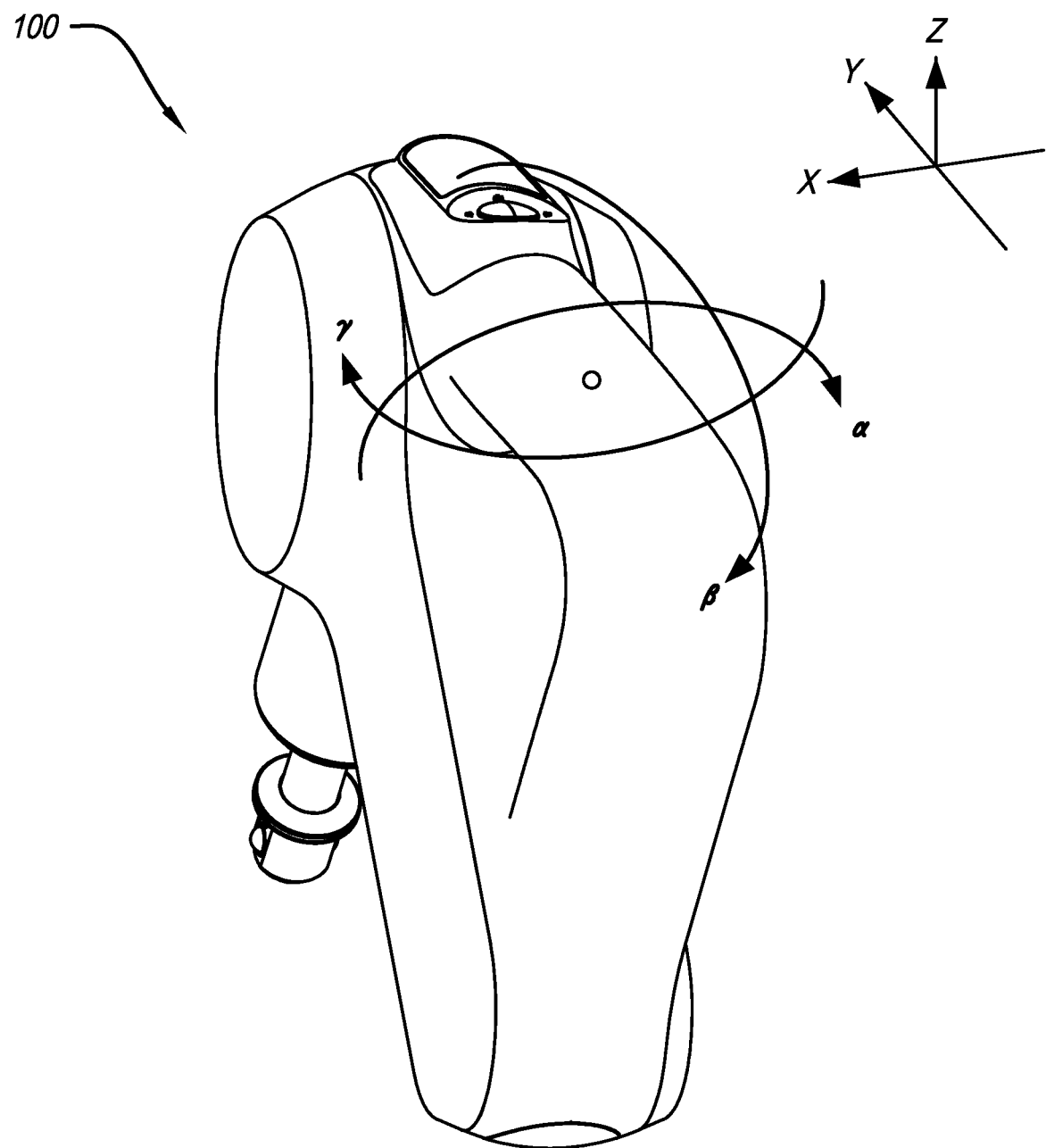
FIG. 41 is a perspective view of a percussive therapy device that includes a gyroscope and accelerometer.
Figure 42A:
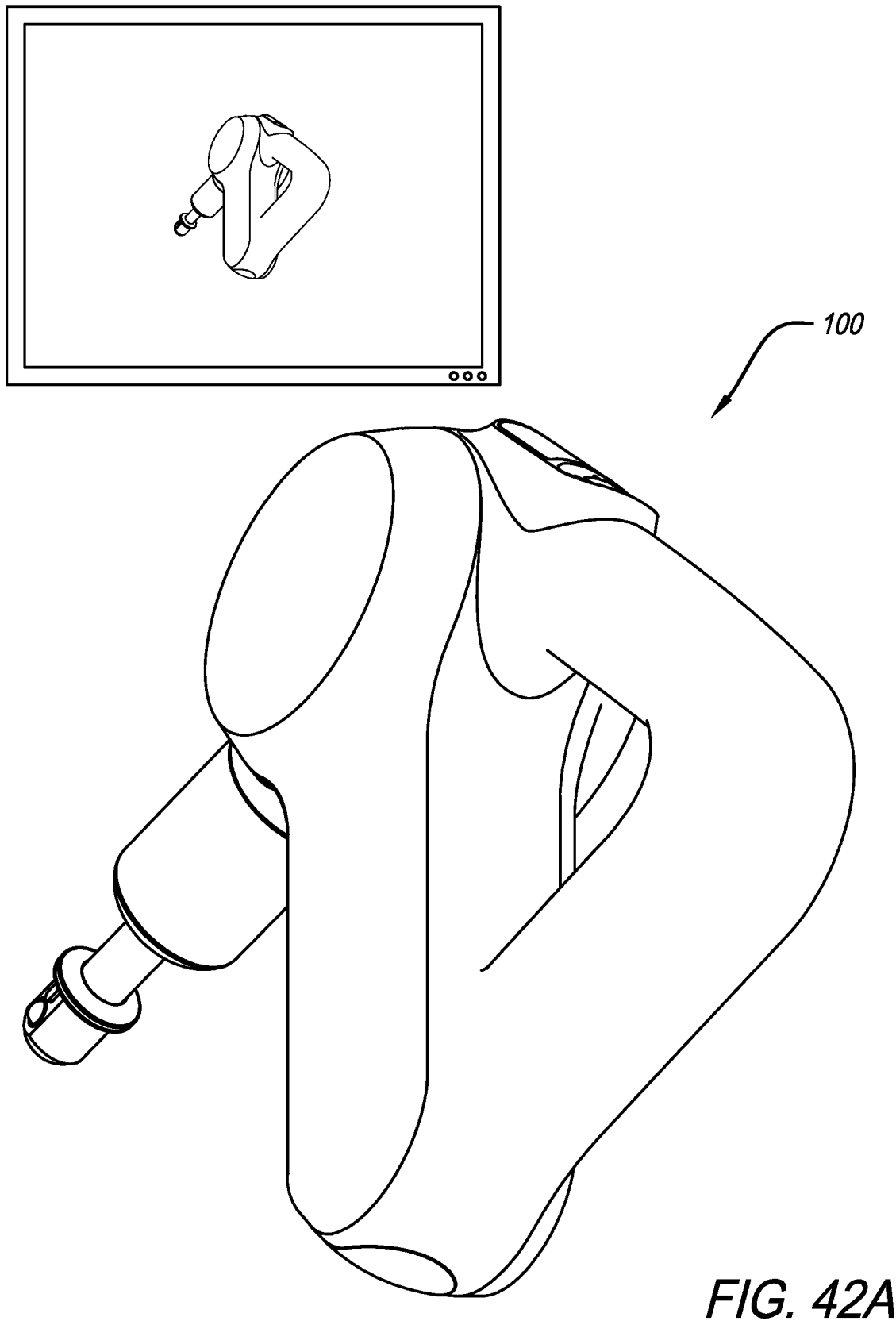
FIGS. 42A-C are perspective views of a percussive therapy device and graphical representations thereof on a display.
Figure 42B:
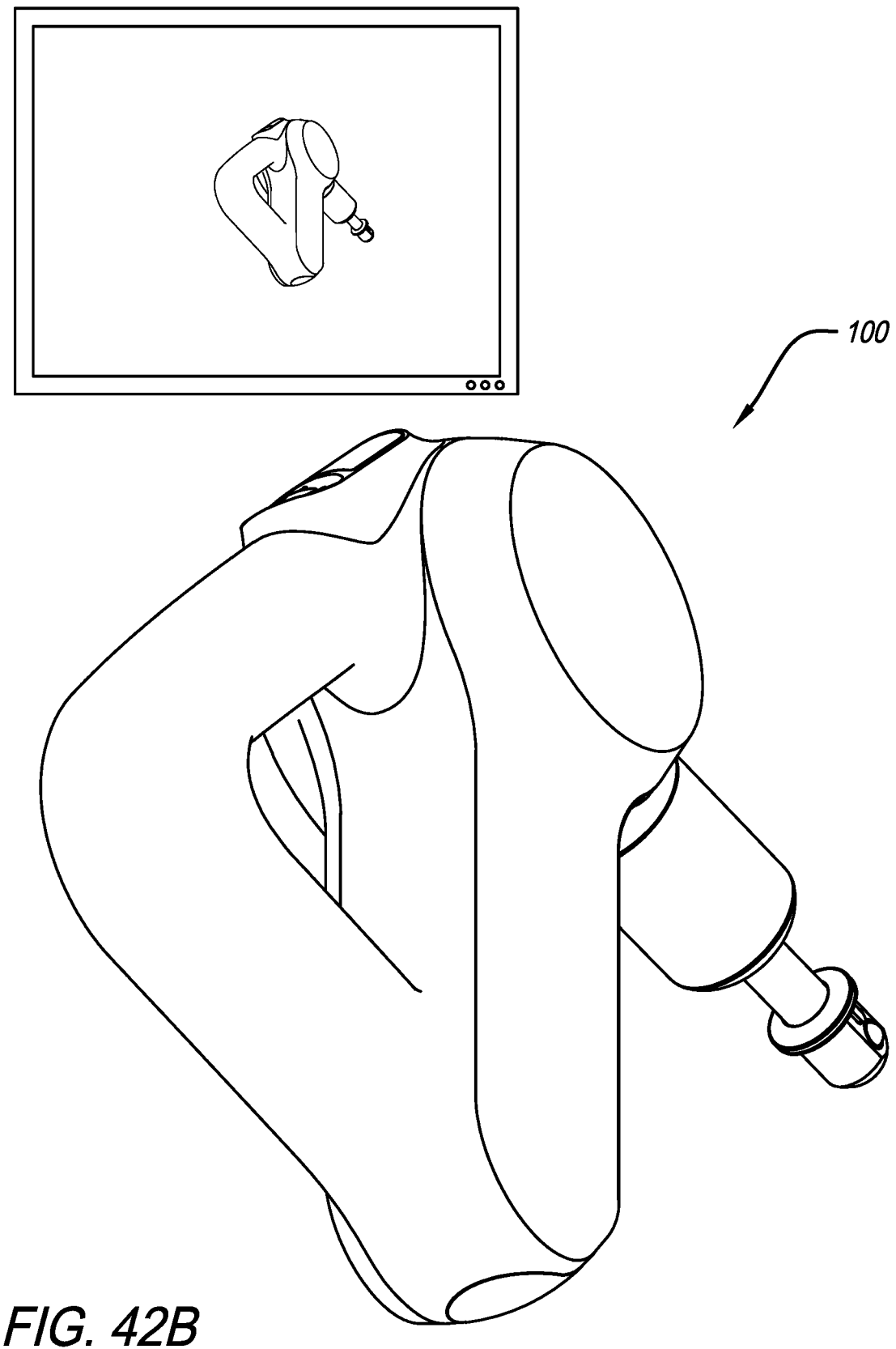
Figure 42C:
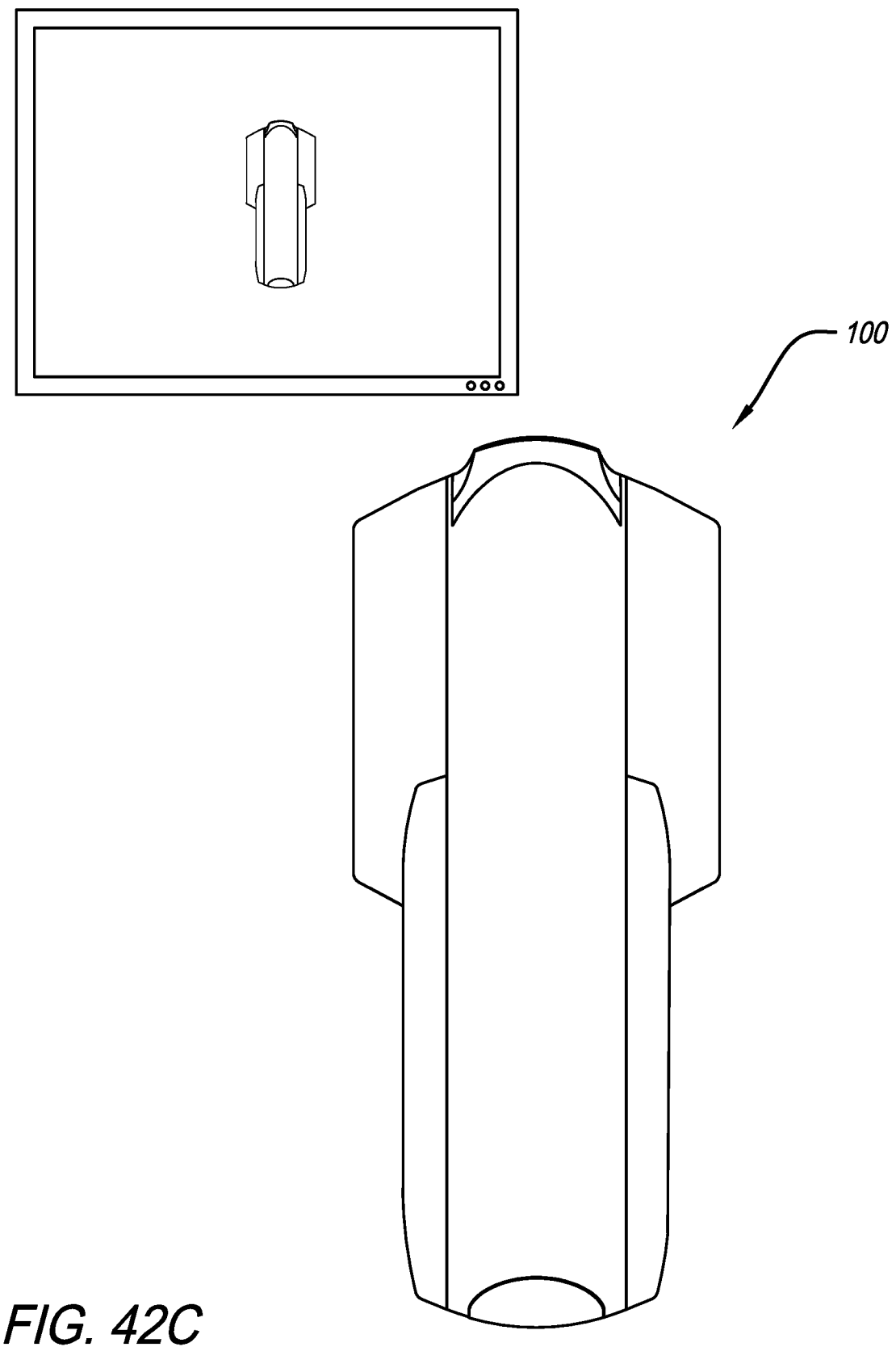

As shown in FIGS. 41-42C, in a preferred embodiment, the percussive therapy device 100 includes an angular position sensor 516 and a linear position sensor 518. See FIG. 37. For example, the angular position sensor 516 is a gyroscope 516 and the linear position sensor 518 is an accelerometer 518. One or more gyroscopes, accelerometers, sensors or the like can be included on or in the device for detecting and gathering data. The system including the device 100 and the angular position sensor 516 and the linear position sensor 518 allows data to be gathered regarding the angular and linear positioning of the device 100. Data can include angular positioning (α,β,γ) (i.e., angular position data) and linear movement in three axes (x,y,z) (i.e., linear position data), for example. In a preferred embodiment, a sensor chipboard 504 is included in the device 100 to measure variations in its angular position in three axes, α, β and γ via a gyroscope 516 and to track linear movement of the device in three axes x, y and z via an accelerometer 518. See FIG. 37. The angular position sensor 516 and the linear position sensor 518 may be implemented on the sensor chipboard 504, or they may constitute separate electronic devices operably connected to the sensor chipboard 504. Other suitable configurations of the angular position sensor 516 and the linear position sensor 518 exist without departing from the scope of this invention.

In an embodiment, the printed circuit board 408 of the device 100 powers the angular position sensor 516 and a linear position sensor 518 and stores the data the sensors generate. For example, the sensor data may be stored in a memory (not shown). In another embodiment, the PCB 408 integrally incorporates the sensor chipboard 504. Preferably, the PCB 408 broadcasts and/or transmits data generated by the sensors through a wireless connectivity standard, such as Bluetooth. For example, the wireless connectivity standard is implemented via the wireless control unit 710 (FIG. 2). The sensors are configured to accurately map how the device 100 moves with respect to the user's muscle during the treatment. In an embodiment, the sensors may also include an oxygen saturation sensor to monitor an amount of oxygen content in the user's blood (e.g., a pulse oximeter or the like), and a blood flow sensor to monitor magnitude and/or velocity of the user's blood flow.

FIGS. 42A-42C show exemplary angular positioning using the angular position sensor 516. As the device 100 is rotated left and right (see FIGS. 42A and 42B) in x and y axes, and tilted upwardly (see FIG. 42C) in the z axis, the angles and direction of the device 100 are shown on a computer monitor or display. The depictions shown in FIGS. 42A-42C illustrate a graphical representation of the device 100 as the device 100 is moved. While FIGS. 42A-42C illustrate angular movement of the device 100, the linear movement of the device 100 is also graphically represented on a computer monitor or display in like manner. It will be appreciated that the movement is shown on the computer monitor in the drawings to provide an example of how the angular position sensor 516 senses the movement.

In a preferred embodiment, the angular and linear position sensors 516, 518, coupled with the force meter of the percussive therapy device 400 discussed above, can be used to map the treatment of a muscle or body part as the device 400 is being used in a three-dimensional display. This "map" or data can be displayed through or on an application or on the touch screen 1582. For example, angular and linear position data obtained from the angular and linear position sensors 516, 518 can be graphically represented via the application or on the touch screen 1582. The angular and linear position data can assist the user in applying a particular protocol or routine, for example, such as those depicted in FIGS. 24-28 and accompanying descriptions, or the like. In addition to angular and linear movement, the force meter of device 400 (or device 457) can obtain force magnitude data to assist the user in administering a routine or protocol constituting a therapeutic treatment to the user (or to another person to whom the user is administering the treatment). For example, the map of angular and linear position and force magnitude can be compared against the routine or protocol. The routine or protocol, in this example, will specify a muscle group, a linear and/or angular path (see FIG. 28, for example, with the starting point 1586 and the ending point 1588, in two dimensions), and a force magnitude that the user is intended to exert on the muscle group (see FIG. 28, for example, with the force display 1590 and force display prompt 1592). In a preferred embodiment, the muscle group, linear and angular position, and force magnitude (i.e., depression on the muscle group) is graphically presented in a three dimensional display. Preferably, the display also graphically illustrates when the user's linear movement, angular movement, or force magnitude exerted on the muscle group is following the protocol or routine. If the user is not following the routine or protocol, the user will receive a prompt to take corrective action to follow the routine or protocol correctly. For example, the prompt may alert the user that the user is applying the attachment 628 to a different muscle group than that specified by the protocol. The prompt may be haptic feedback, application interface, or touch screen (among other types of prompts). The prompt may also be presented in a two-dimensional or three-dimensional graphical representation. As a result, the device can track over time what regions of a user's muscles or body parts are being worked the most and whether the user is positioning the device correctly. The prompt may also let the user know they are positioning the device incorrectly or they are working on the wrong body part (e.g., during the treatment protocols).

Referring again to FIG. 36, the device 457 is shown depressing the attachment 628 onto a user's body part. In accordance with the description above, the depression may be graphically represented in two or three dimensions on a display. In practice, the attachment 628 shown in FIG. 36 is configured to provide percussive effect to the user's body part, and thus, exerts a force onto the user's body part. The force meter measures the force magnitude of the attachment 628 when depressed onto the user's body part. The force magnitude data is then transmitted to a monitor/display, application, or touch screen 1582, or the like, to show a user (or other person) the amount of force exerted on the user's body part during a protocol or routine. Gathering multi-sensory data allows for augmented reality features that can be used to train users and recovery professionals virtually on how to use the device 400, 457.

As an example, while a user's quad muscle is not a uniform shape, it is possible to simplify the user's quad muscle to the shape of a cylinder. The angular and linear position can be ascertained, and thus, a determination can be made concerning how the device 400, 457 is positioned relative to the cylinder. Further, a determination can be made concerning the direction the percussive arm (e.g., push rod assembly 14, shaft 16, and/or attachment 628) is directed of the device 400, 457. The determination can also be made concerning how the device is moving relative to the cylinder in linear coordinates. The force magnitude from the force meter of the device 400, 457 allows confirmation that the device 400, 457 is in contact with the muscle, as well as the intensity and duration of that interaction.

Similarly, the device 400, 457 can also include a thermal sensor 462 or thermometer 462 that can determine the temperature of the user's muscle and to provide feedback to the device and/or application. See FIG. 36, thermal sensor 462. For example, an electronic thermometer 462 that reads the temperature of the user's skin or muscle before, during and/or after treatment can be included. In an embodiment, the thermal sensor 462 is located in the housing 12 of the device 400, 457 where infrared radiation or wavelengths can be used to measure temperature. In another embodiment, the thermometer 462 can be positioned to require direct contact to measure the temperature and/or it may utilize wireless technology, like an infrared sensor, to make the temperature readings. For example, FIG. 40 illustrates how the attachment 508 may function as (or include) a thermal sensor 462, a heating element 502, or both. Similarly to the heating element 502 as shown in FIG. 37, for example, the thermal sensor 462 may be connected to the PCB 504 via the electrical wiring 506 and may be located in the attachment 628. The electrical contacts 510, 512 (or metal balls 514) as shown in the embodiments of FIGS. 38-39 provide electrical connectivity between the PCB 504, the male or female connector 110, and thus, the thermal sensor 462. As with the heating element 502, a thermal sensor 462 may be utilized as part of a protocol or routine.

In an embodiment, a three-dimensional rendering of thermal readings from the thermal sensor 462 is provided to a user to show incremental increases in temperature over time. For example, a three-dimensional rendering may show varying colors from blue (e.g., cool) to yellow/orange (e.g., medium temperature) to red (e.g., hot) to illustrate to the user the increase in temperature over time.

An accessory, module or attachment module 520 can be used with and attached or secured to a percussive massage or percussive therapy device 100, 400, 457 as part of a percussive therapy system 500. In a preferred embodiment, the attachment module 520 includes a thermal sensor or thermometer 462 that can determine the temperature of the user's muscle and to provide feedback to a device and/or application. In a preferred embodiment, the thermal sensor 462 allows the application to determine or customize the timing of each step within a protocol. The temperature can be used to determine blood flow and therefore muscle readiness for a specific goal (e.g., relaxation, performance, focus).

Figure 43:
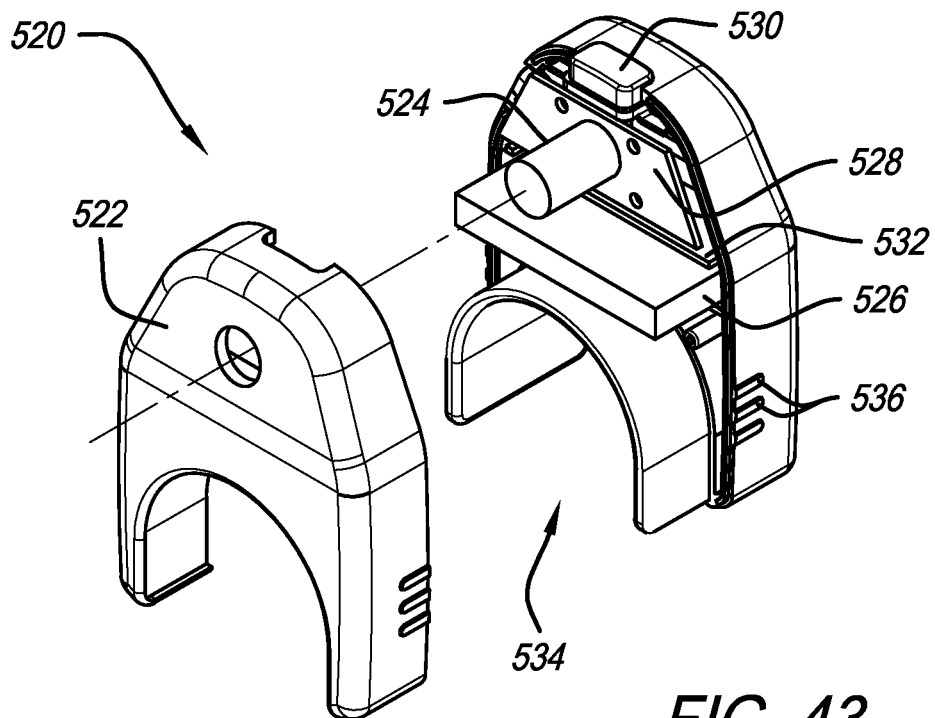
FIG. 43 is a perspective view of an attachment configured to be operably connected with a percussive therapy device.
Figure 44:
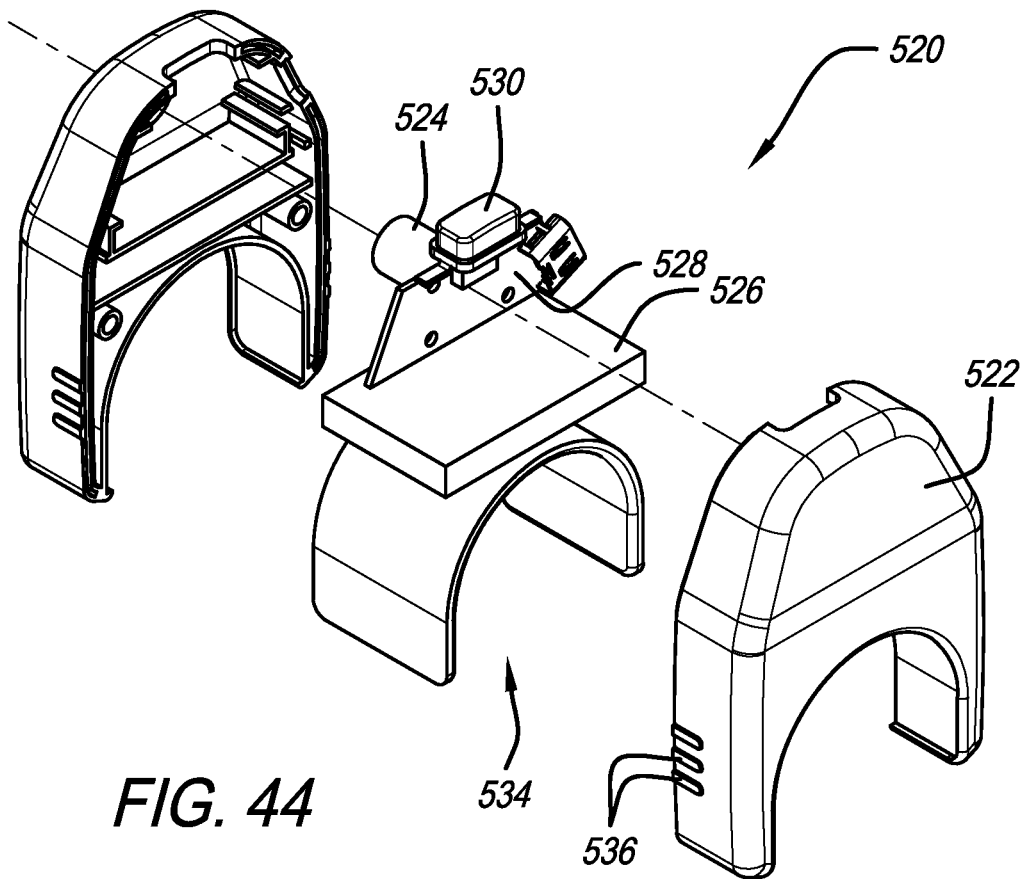
FIG. 44 is a perspective view of an attachment configured to be operably connected with a percussive therapy device.
Figure 45:
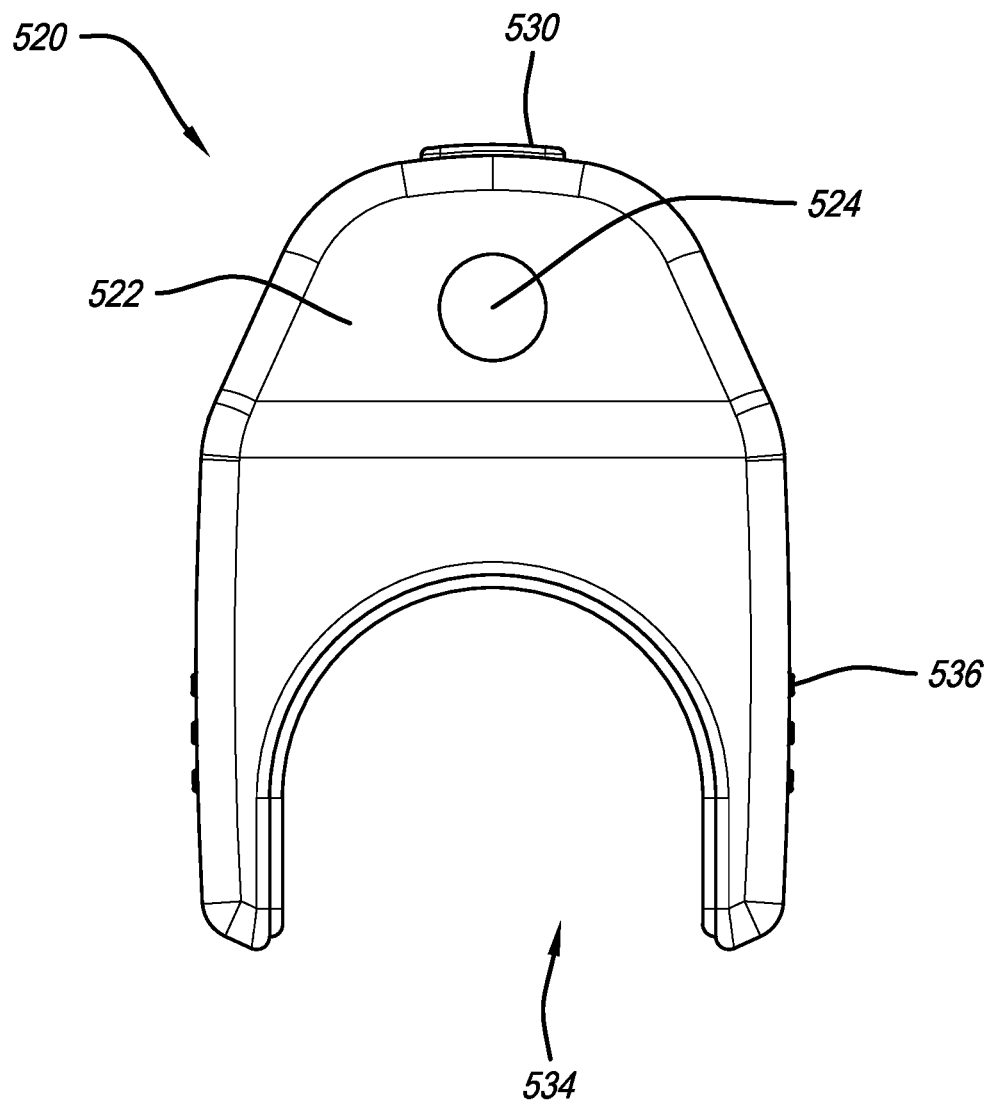
FIG. 45 is a bottom view of an attachment configured to be operably connected with a percussive therapy device.

As shown in FIGS. 43-45, in a preferred embodiment, the attachment module 520 includes a housing 522, a thermal sensor 524, a battery 526, a printed circuit board (PCB) 528 (that includes a gyroscope 516 or other angular/positional device, e.g., the angular position sensor 516, and/or an accelerometer 518 or other linear/positional device, e.g., the linear position sensor 518), a button 530 and a wireless communication module 532 (e.g., a Bluetooth module). In a preferred embodiment, the housing 522 includes a securement portion 534 defined therein so that the attachment module 520 can be secured to a percussive therapy device 400, 457. The securement portion 534 or recess 534 can include rubber on the inside thereof to provide grip on the percussive therapy device. Protrusions 536 are preferably included on both sides of the housing 522 to provide grip when securing and removing the attachment module 520 from the percussive therapy device 400, 457. In another embodiment, the wireless connection module can be omitted and the attachment module can include a display or screen for displaying information, such as temperature, angular and linear position, or any other information obtained or sensed by the attachment module.

Figure 46:
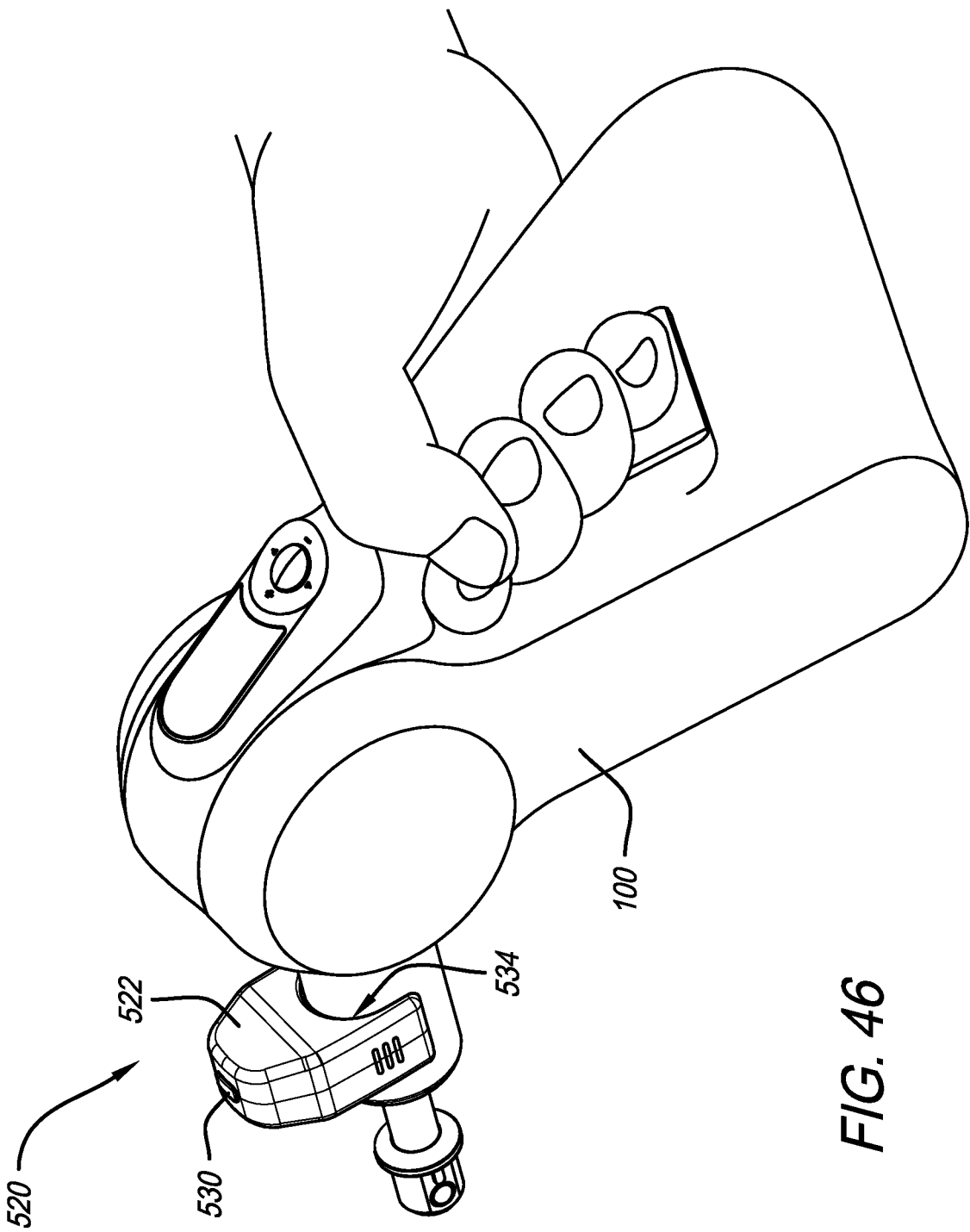
FIG. 46 is a perspective view of a percussive therapy system including a percussive therapy device and an attachment thereon.
Figure 47:
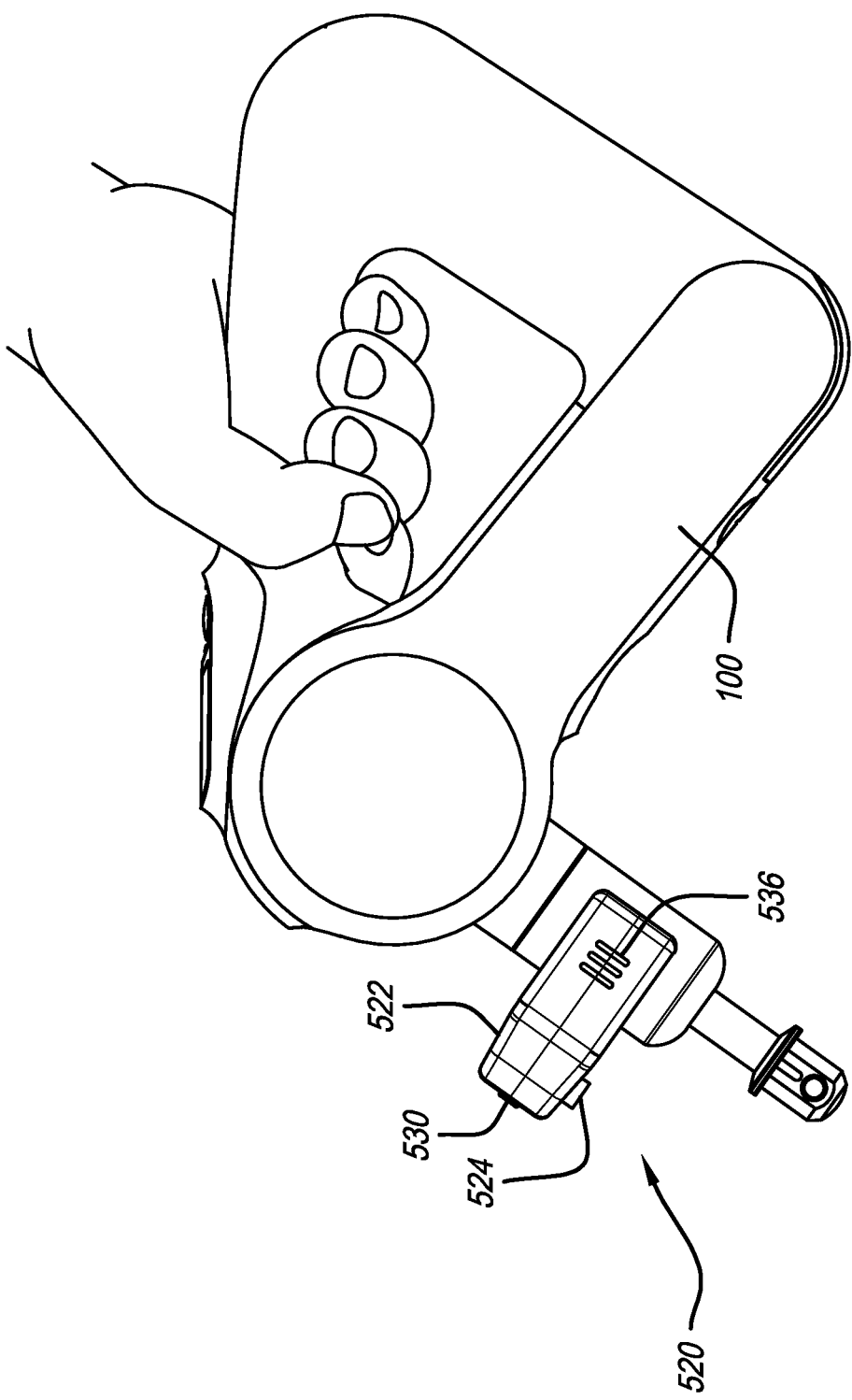
FIG. 47 is a perspective view of a percussive therapy system including a percussive therapy device and an attachment thereon.

As described above with respect to FIG. 36, any type of thermal sensor 524 is within the scope of the invention. In the embodiment shown in FIGS. 43-45, the thermal sensor 524 is an infrared thermometer module installed in the housing 522 and directed downwardly when installed on a percussive therapy device 100 as shown in FIGS. 46-47 (shown in a non-limiting position on the front arm of the percussive therapy device 100). In another embodiment, the thermal sensor 524 is the thermal sensor 462 and can be secured to the third handle portion 147 or bottom of a percussive therapy device 400, 457 or on any handle portion 143, 145, 147 or part of a percussive therapy device 400, 457 where it can be positioned and allow the user to measure the temperature of the user's muscles or other body part. See FIG. 36. The attachment module 520 can be used with any type of percussive therapy device 500, massage device or other device where temperature and/or positioning measurements are desired. It will be appreciated that all embodiments and components thereof are interchangeable with all other embodiments and components thereof.

In a preferred embodiment, the attachment module 520 communicates wirelessly with the percussive therapy device 400 and/or the application on the user's mobile device. See FIG. 2, the wireless control unit 710, and accompanying discussion. In another embodiment, the attachment module 520 is physically and electrically connected to the device 400 and no wireless module is needed as communication is achieved through conventional electrical wires or the like.

Referring again to FIG. 36A, a temperature readout on the screen 409 of the percussive therapy device 100 is shown. The thermal sensor 524 is preferably in data and/or electrical communication with the PCB 528 and the data is communicated to one or both of the device 400 or application.

In a preferred embodiment, the temperature reading capability is integrated with and a part of the treatment routines or protocols described herein or by reference. For example, instead of a routine or a step within a routine running or extending for a predetermined period of time, the routine or step (i.e., the amount of time a particular muscle or body part is treated or targeted) can extend until the muscle or body part (referred to generally herein as a body part) reaches a predetermined temperature. Accordingly, reaching a predetermined temperature can be substituted for predetermined period of time for any of the routines. For example, step 1526 in FIG. 26C can be substituted for the step of "apply attachment to specified body part until a specified temperature is reached." This can be used to be sure that a body part has been warmed up properly prior to exercise. Therefore, in use, the temperature will rise from a starting temperature to a predetermined finishing temperature and the routine can then go to the next step or end. There also may be a number of "temperature steps" that are each part of the a routine. For example, during the first step, the muscle may increase in temperature from the starting temperature to a second temperature. The next step may involve additional treatment until the temperature reading increases from the second temperature to a higher third temperature. The temperature range between the starting and the finish temperature within the routine may also be different for each user. Furthermore, haptic feedback or other notification or instructions can be provided to let the user know when the finish temperature or predetermined temperature has been reached and that they can move to the next step in the routine.

In a preferred embodiment, the attachment module 520 includes an angular position sensor 516 (e.g., gyroscope 516) and/or a linear position sensor 518 (e.g., accelerometer 518). Each or both can be implemented as part of the PCB 18. One or more gyroscopes 516, accelerometers 518, sensors or the like can be included on or in the device 400 for detecting and gathering data. One or more actuators may also be included on or in the device 400 for providing at least one therapeutic effect. Thus, the description above referencing gyroscopes, 516, accelerometers 518, attachments 628, 508, male or female attachment members 110, or sensors or actuators within or without the housing 101 is instructive and within the scope of the attachment module 520. See FIGS. 36-42C. For example, a heating element 502 may be implemented in the attachment module 520 to utilize radiation to penetrate skin and muscle to a certain depth. This treatment can result in muscle recovery.

In an embodiment, the percussive therapy system 500 is configured to determine at least one characteristic of the attachment 628, 508. For example, a percussive therapy device 100, 400 itself may include circuitry and wired or wireless communication to sense the type of attachment the user intends to use in connection with the device 100, 400. For example, the device 100, 400 may sense that the attachment 628 is a dampener. Other characteristics of the attachment 628, 508 may be sensed. For example, the existence of one or more sensors included in the attachment 628, 508 may be sensed. In addition, the existence of one or more actuators included in the attachment 628, 508 may be sensed. In an embodiment, the device 100, 400 senses when the attachment 628, 508 is attached to a distal end of the push rod assembly 14. Once the attachment 628, 508 is attached, then the device may, through wired connections (e.g., positive/negative contacts 510, 512 or the like, or other wired electrical connections), sense the various characteristics of the attachment 628, 508. In this embodiment, the wired connections may communicate with the PCB 408, 504 so that the device 100, 400 determines the characteristics. In another embodiment, the attachment 628, 508 may include wireless communication capabilities and communicate the characteristics wirelessly. One of ordinary skill in the art would understand that there are a variety of methodologies to employ to communicate the characteristics to the device 100, 400 and/or the user, preferably through communication on a remote device or touch screen 1582.

Figure 48:
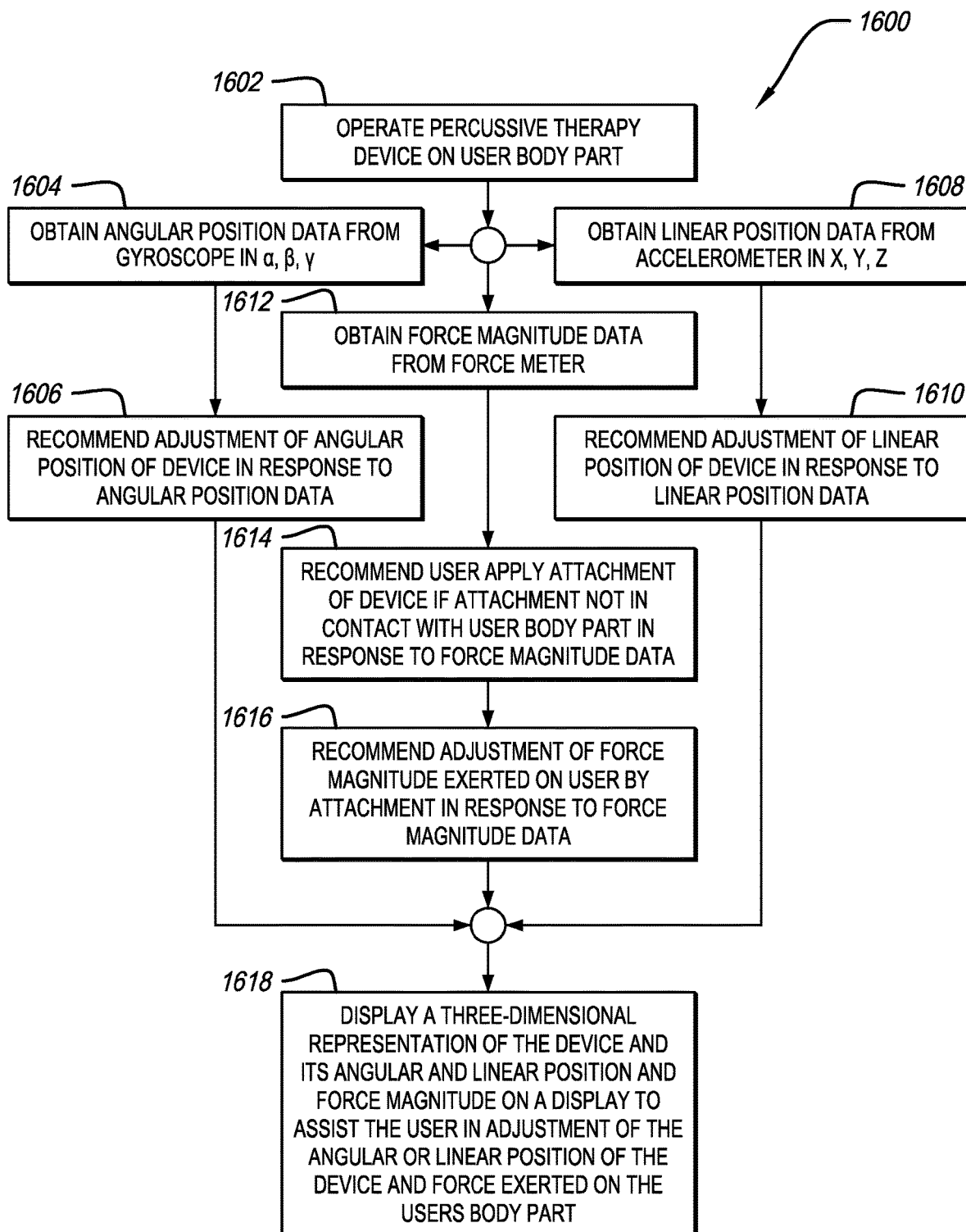
FIG. 48 is a flow diagram of a method of providing at least one therapeutic effect to a user in accordance with an embodiment of the present invention.

FIG. 48 is a flow diagram of a method 1600 of providing at least one therapeutic effect to a user in accordance with an embodiment of the present invention. At Step 1602, a percussive therapy device 400, 457 is operated on a user's body part. For example, the user initiates a protocol such as that shown in FIGS. 24-28 and accompanying descriptions, or the like. In accordance with the specified protocol initiated, the user typically is instructed to operate the percussive therapy device (or other suitable therapeutic treatment or effect) in accordance with steps of the protocol in a specified fashion. For example, the user may be instructed to orient the device 400, 457 at a specified angle relative to a muscle group, along a linear path relative to the specified muscle group, and/or with a certain amount of force exerted on the specified muscle group. At Step 1604, angular position data is obtained from a gyroscope 516 in three rotational axes $(\alpha,\beta,\gamma)$. The gyroscope may also be an angular position sensor 516 or suitable replacement. At Step 1606, adjustment of an angular position of the percussive massage device 400, 457 is recommended in response to the angular position data. As illustrated in FIGS. 42A-C, the angular position data may show that the angular position of the device 400, 457 is correctly oriented relative to a body part. It may also reveal that the angular position of the device 400, 457 is incorrectly oriented. Thus, the recommendation preferably instructs the user to orient the device 400, 457 properly relative to the body part.

At Step 1608, linear position data is obtained from an accelerometer 518 in three linear axes (x, y, z). The accelerometer may also be a linear position sensor 518 or suitable replacement. At Step 1610, adjustment of a linear position of the percussive massage device 400, 457 is recommended in response to the linear position data. For example, in FIG. 28, a right bicep routine is shown that instructs the user to move the device 400, 457 from the starting point 1586 (A) to the ending point 1588 (B). If the user correctly follows the linear path from (A) to (B), then the recommendation may indicate so to the user. If the user is not correctly following the linear path from (A) to (B), then the recommendation preferably instructs the user to adjust the linear position of the device 400, 457 and/or attachment 628 to correctly follow the linear path and the predetermined routine.

At Step 1612, force magnitude data is obtained from a force meter included in the percussive therapy device 400, 457. At Step 1614, application of the attachment 628 of device 400, 457 to the user's body part is recommended if the attachment 628 is not in contact with the user's body part in response to the force magnitude data. For example, the force magnitude is approximately zero (or a de minimus threshold amount) that may be predetermined if the attachment is not in contact with the user's body part.

At Step 1616, adjustment of a force magnitude exerted on the user by the attachment 628 of the device 400, 457 is recommended in response to the force magnitude data. For example, in FIG. 28, a force magnitude exerted on a right bicep is illustrated in accordance with the force display 1590. In that embodiment, the force display prompt 1592 reads "PERFECT PRESSURE: WELL DONE", indicating that the pressure the user is exerting on the right bicep is in accordance with the pressure specified by the predetermined right bicep routine. In the event that the force magnitude is lower or higher than the pressure specified by the routine, the recommendation will read "INCREASE PRESSURE" or "DECREASE PRESSURE" as needed.

At Step 1618, a three-dimensional representation of the device 400, 457 and its angular and/or linear position and/or force magnitude is displayed on a display. The angular position of the device 400, 457, in an embodiment, is displayed similarly to the graphic shown in FIG. 42A-C. The display may be situated on a touch screen 1582, a mobile device, or other remote device. The display of the three-dimensional device is utilized to assist the user in adjustment of the angular and/or linear position of the device and/or the pressure (e.g., force magnitude) exerted on the user's body part. See FIGS. 42A-C and accompanying description concerning "mapping" of device 400, 457 relative to the user's body part.

Figure 49:
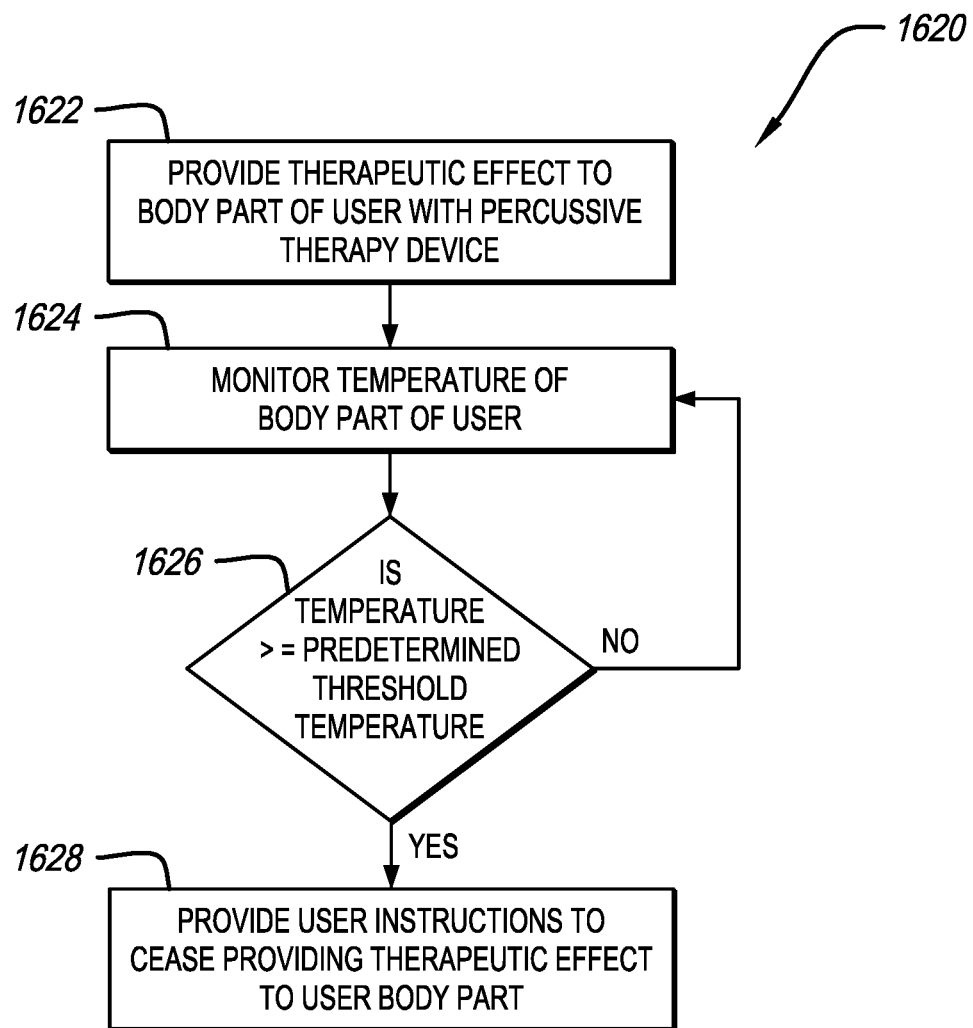
FIG. 49 is a flow diagram of a method of preparing a user's body part for exercise in accordance with an embodiment of the present invention.

FIG. 49 is a flow diagram of a method 1620 of preparing a user's body part for exercise in accordance with an embodiment of the present invention. At Step 1622, a therapeutic effect is provided to the user's body part using the percussive therapy device 400, 457. The therapeutic effect may include a variety of massage or other treatments, including vibration, concussion, heat, or exfoliation. A heating element 502 or other heating actuator may be implemented to increase the temperature during the time that the therapeutic effect is provided to the user.

At Step 1624, a temperature of the user's body part is monitored. At Step 1626, it is determined whether the temperature reading is greater than or equal to a predetermined threshold temperature. Once the temperature reaches the predetermined threshold temperature, for example, the user's body part is ready for exercise. This may vary depending on the user and the user's body part. If the temperature is less than the predetermined threshold temperature, Steps 1622 and 1624 are repeated. If the temperature is greater than or equal to the predetermined threshold temperature, then Step 1628 is implemented. At Step 1628, user instructions are provided to cease providing the therapeutic effect to the user's body part. The user's body part is warm enough to exercise safely and effectively with lower risk for exercise-related injury, and can also improve performance of the user during the exercise.

FIGS. 50-53 show another type of attachment module 312 that is configured to be attached or secured to the housing 101 of the percussive therapy device 100 (or any of the percussive therapy device embodiments described herein). This provides interchangeability between attachment modules with different active effects. In a preferred embodiment, the attachment module is configured to provide an active effect either to the user of the device or with respect to the device. All of the therapeutic effects, sensors, actuators, gyroscopes, accelerometers or other active features described herein are encompassed within the phrase "active effect." These can include global biometric sensors, local biometric sensors and/or actuators, such as, heart rate, heart rate variability, $SPO_2$, respiratory rate, muscle temperature, muscle oxygen saturation, blood flow, cold therapy, heat therapy, light therapy (red, infrared, blue, etc.), photobiomodulation therapy, vibration therapy, exfoliating therapy, obtaining biometric data of the user (e.g., temperature, heart rate, blood pressure, oxygen saturation, blood flow sensing), angular position data of the percussive therapy device, linear position data of the percussive therapy device, microcurrent therapy, radio frequency therapy, ultrasound therapy, infrared therapy, far infrared therapy, electric muscle stimulation, etc. Some of the active effects are associated with providing a therapy to the user and others (e.g., angular and linear position sensing) are associated with the device.

Figure 50:
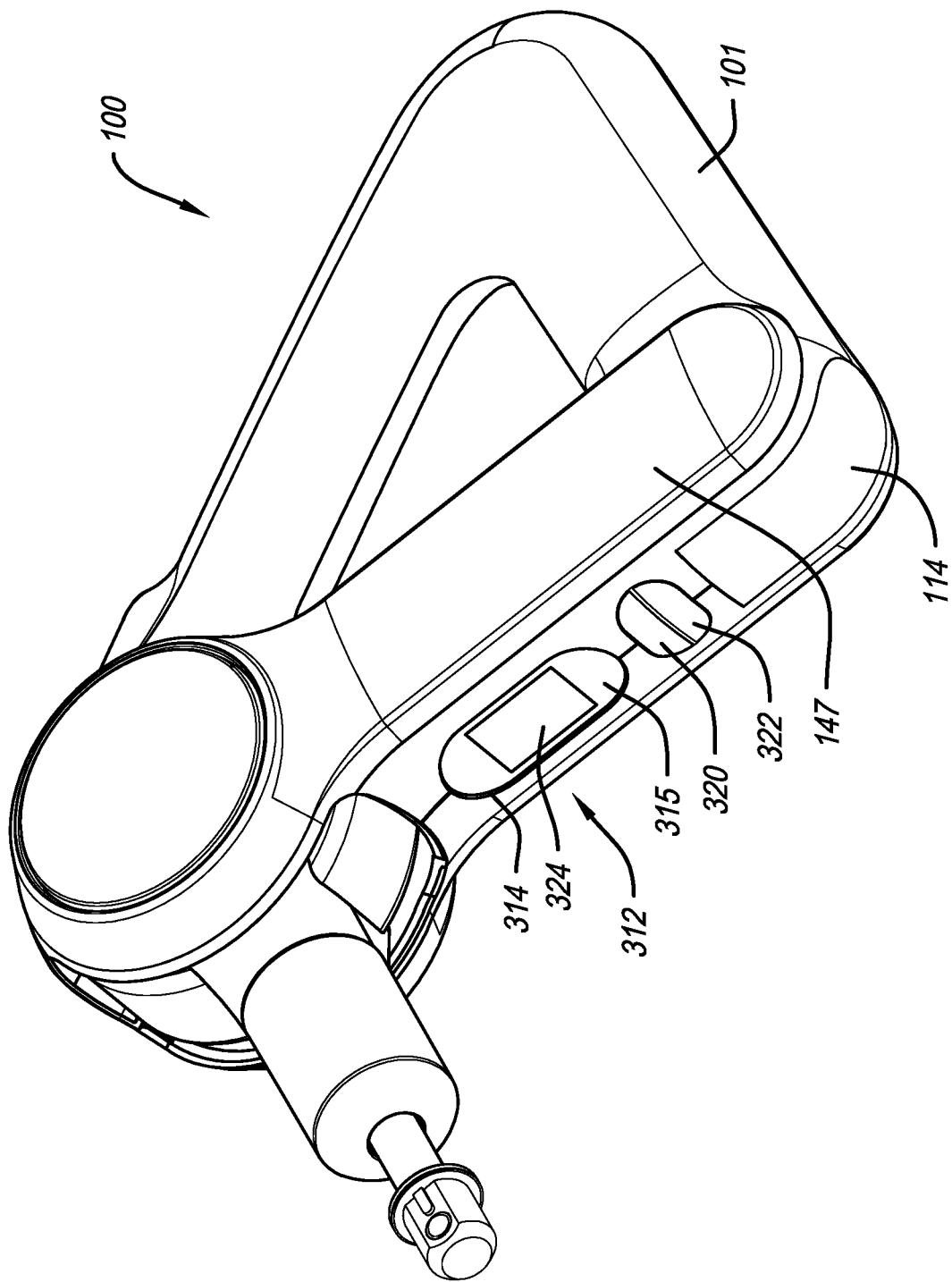
FIG. 50 is a perspective view of a percussive therapy device that includes an attachment module thereon, in accordance with a preferred embodiment of the present invention.
Figure 51:
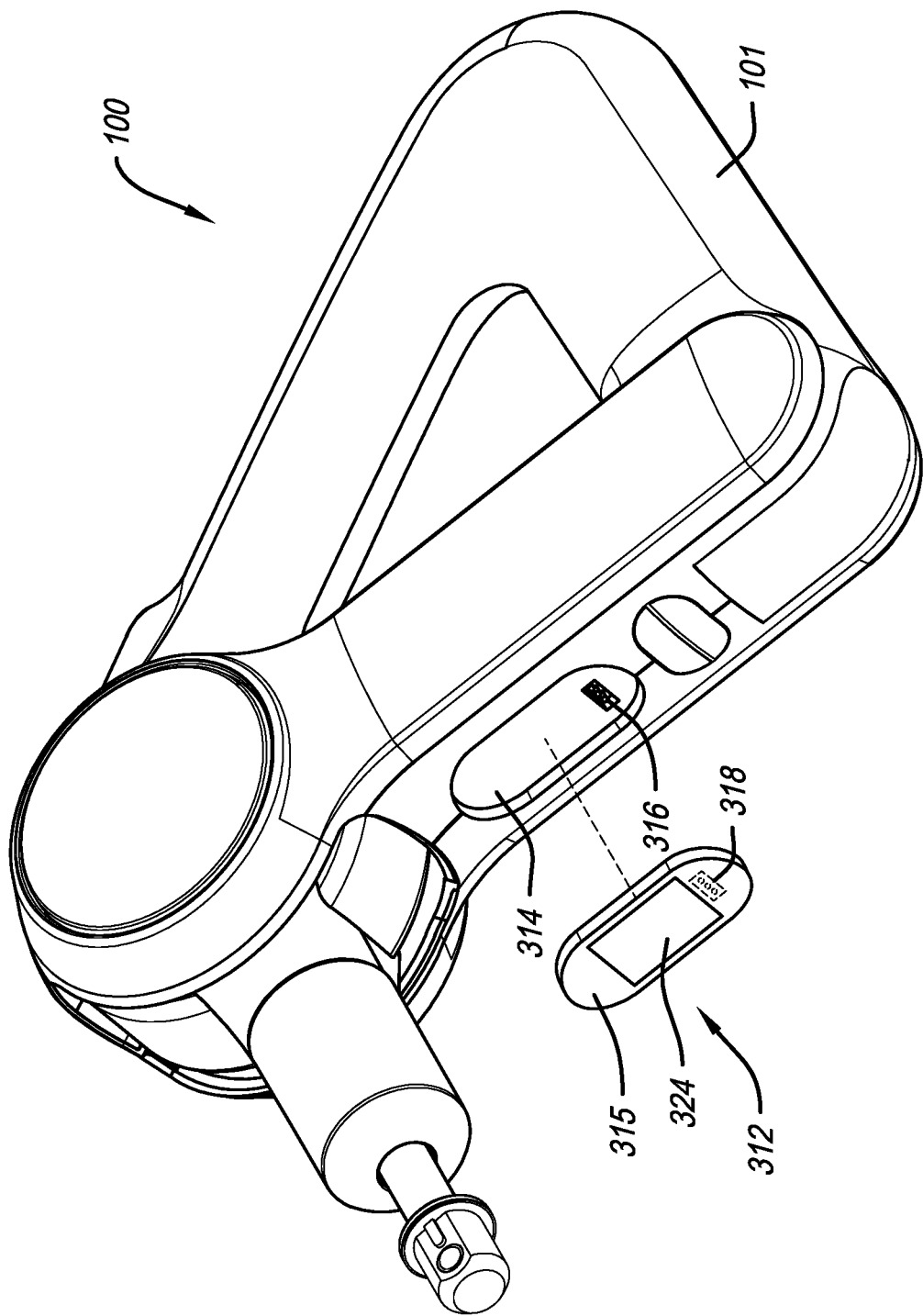
FIG. 51 is a perspective view of the percussive therapy device of FIG. 50 with the attachment module exploded therefrom.

As shown in FIGS. 50-51, in a preferred embodiment, the attachment module 312 is received in a module recess 314 or module seat that is defined in the bottom or belly of one of the third handle portion 147 of the housing 101. The module recess 314 can be defined anywhere within the housing or on any of the handle portions of the device. In a preferred embodiment, the attachment module 312 is in electrical communication with the electrical source (e.g., rechargeable battery). The housing 101 includes a first electrical connector 316 and the attachment module 312 (preferably associated with the housing 315 of the attachment module 312) includes a second electrical connector 318. Connection of the first and second electrical connectors provides electrical communication between the electrical source and the attachment module 312. The first electrical connector 316 can be located on the outer surface of the housing 101 or within the module recess 314. In a preferred embodiment, connection of the first and second electrical connectors 316 and 318 also provides data communication between the percussive therapy device (e.g., to the PCB 504) and the attachment module 312.

In a preferred embodiment, the attachment module 312 is secured in place with one or more magnets. Preferably, there is magnetic attraction between the attachment module 312 and the module recess or module seat. In other words, a first magnet or set of magnets can be located in or on the attachment module 312 and a second magnet or set of magnets can be located in, on, within or adjacent to the module recess or module seat.

The attachment modules 312 can be secured or attached to or within the module recess via other methods or technologies, such as latches, detents, pawls, friction fit, snap fit, etc. The device 100 can include a button 320 that can be pressed to remove the attachment module 312. The button 320 can be located anywhere on the housing or on the attachment module itself. Button 320 is shown in FIG. 50 next to the button 322 used for removal of the battery 114. In FIG. 50, the attachment module 312 includes a heating element 324 (which can provide heat or cold therapy as the active effect). FIGS. 52A, 52B and 52C show exemplary attachment modules 312 that include various types of active effects. FIG. 52A shows the heating element 324, FIG. 52B shows a plurality of LEDs 326 for provision of LED light or photobiomodulation therapy, and FIG. 52C shows a temperatures sensor 328.

Attachment module 312 may include any of the features described herein with respect to attachment module 520, such as integration of the data obtained from the attachment module 312 with the protocols discussed herein, inclusion of a PCB and/or controller. Furthermore, the active effect provided by the attachment module 312 can be included in one or more protocols. For example, if the attachment module 312 provides heat therapy, a protocol may include steps where the user is directed to place the heating element against a body part for a predetermined period of time.

Figure 53:
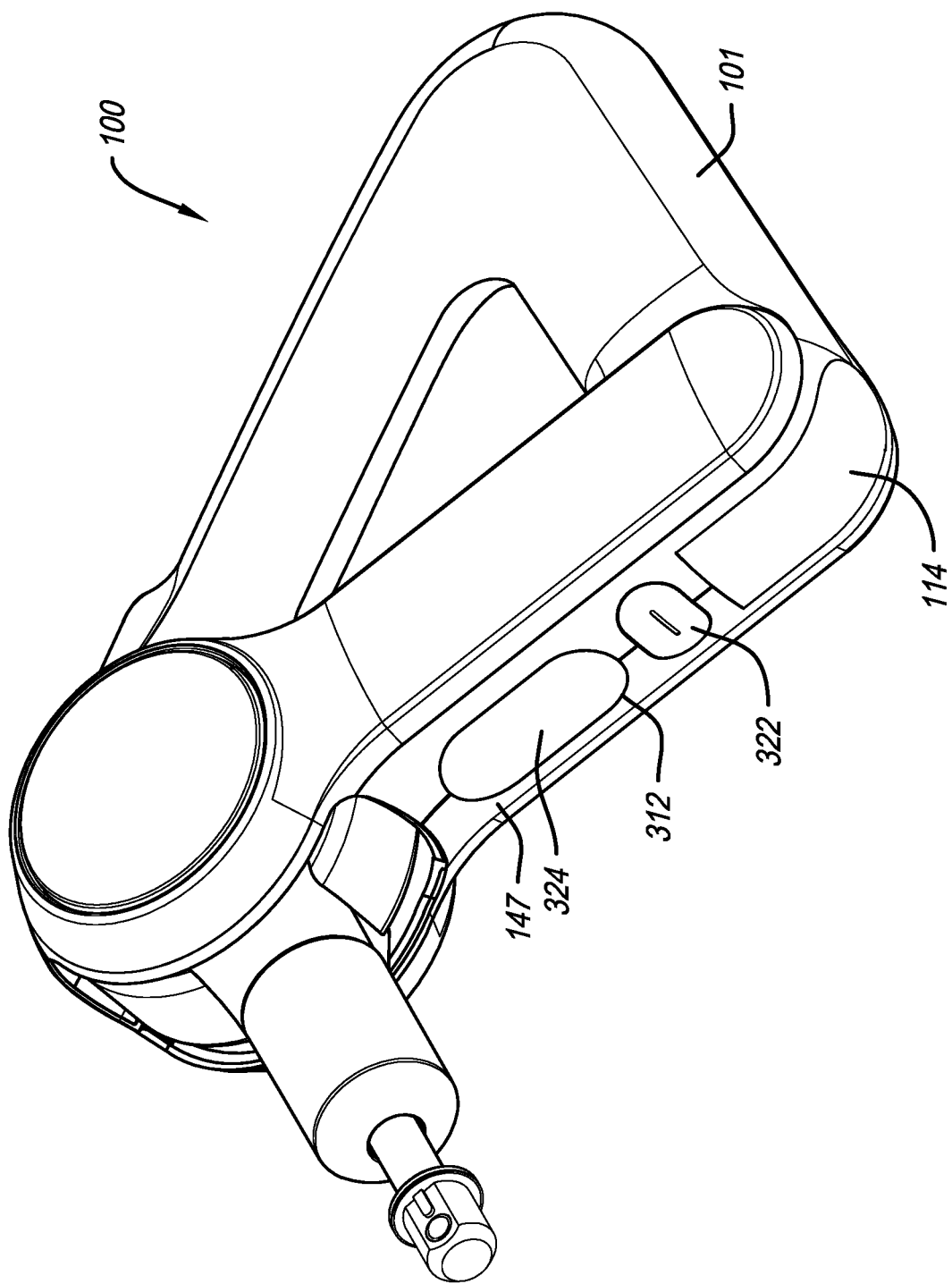
FIG. 53 is a perspective view of a percussive therapy device that includes an attachment module permanently secured thereon, in accordance with a preferred embodiment of the present invention.

In another embodiment, attachment module 312 can be permanently attached to or within the housing 101. In other words, in this embodiment, attachment module 312 is not readily removable (or intended to be removable) by a user of the device (as opposed to a user taking the device apart to remove the attachment module). The attachment module is secured to or within the housing during manufacturing of the device as not intended to be removed by an end user of the commercial product. It is not interchangeable with other attachment modules. For example, FIG. 53 shows an attachment module 312 permanently attached within the housing 101 and configured to provide heat therapy via heating element 324. In this example, the attachment module can only be removed from the housing by someone using tools to take the device apart and remove the heating element and associated portions of the attachment module. This is in contrast to the interchangeable modules that are easily and readily removable from the housing by the user (e.g., via pulling the attachment module away from the housing to break the magnetic attraction or pushing a button to remove the attachment module).

Figure 54:
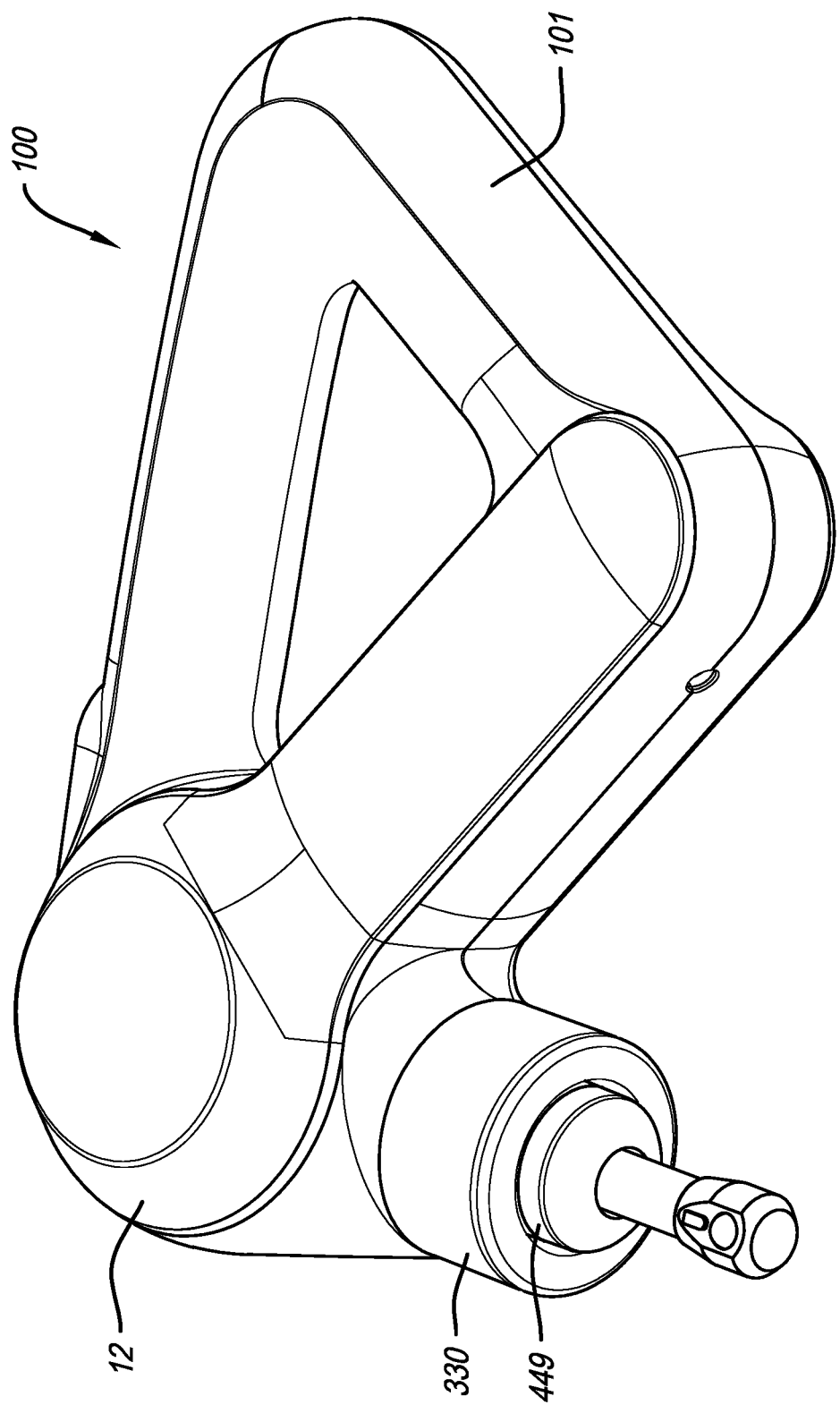
FIG. 54 is a perspective view of a percussive therapy device that includes an attachment module around the push rod assembly, in accordance with a preferred embodiment of the present invention.
Figure 55:
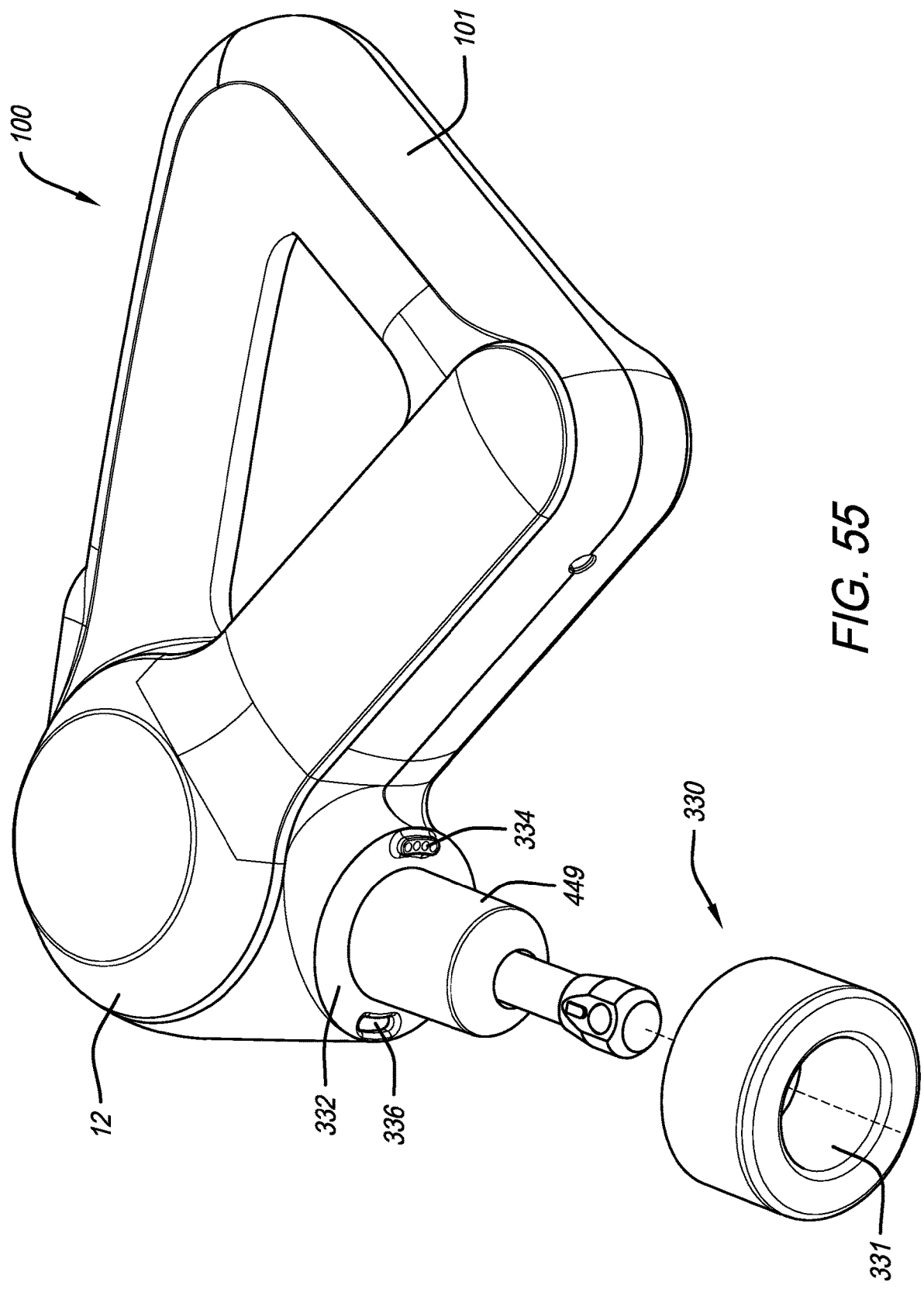
FIG. 55 is a perspective view of the percussive therapy device of FIG. 54 with the attachment module exploded therefrom.

FIGS. 54-55 show another embodiment of an attachment module 330 that is secured over and around the portion of the housing 101 that surrounds the push rod assembly (e.g., the arm cover 449). U.S. patent application Ser. No. 17/705, 300 (the "'300 application") is incorporated by reference herein in its entirety. Similar to the ring modules taught in the '300 application, attachment module 330 includes a central opening 331 that fits over arm cover 449, such that the attachment module 330 can be secured on and attached to a module seat 332 on the head portion 12 of the housing 101. Attachment module 330 in FIG. 54 is an LED light ring. The various attachment modules 330 are interchangeable and removably received on the module seat 332. Preferably, the module seat 332 together with the attachment module 330 includes attachment system for properly aligning or mounting and attaching or securing the various attachment modules on the module seat 332, as well as providing electrical connection or communication (if needed) between the attachment modules 330 and the percussive therapy device 100. In a preferred embodiment, the attachment system includes magnetic attraction between the module seat 332 and attachment modules 330 and includes one or more complementary securement protrusions 334 and securement recesses 336 extending or protruding from the module seat 332 and/or the back of the attachment module. The securement protrusions are received in the securement recesses. Either of the securement protrusions 334 and securement recesses 336, can include male or female electrical connection members (prongs or openings). The attachment system provides the ability to accommodate the swappable or interchangeable attachment modules 11. However, the attachment modules 330 can be secured or attached to the module seat and/or the head portion 12 via other methods or technologies, such as latches, detents, pawls, friction fit, snap fit, etc. A button (similar to button 320 can be included to release attachment module 330.

Any of the sensors, actuators or components that provide an active effect can be included in the ring attachment module 330. These can include local biometric sensors or actuators, such as those that can sense or determine muscle temperature, muscle oxygen saturation, blood flow or deliver light therapy (red, infrared, blue, etc.).

Figure 56:
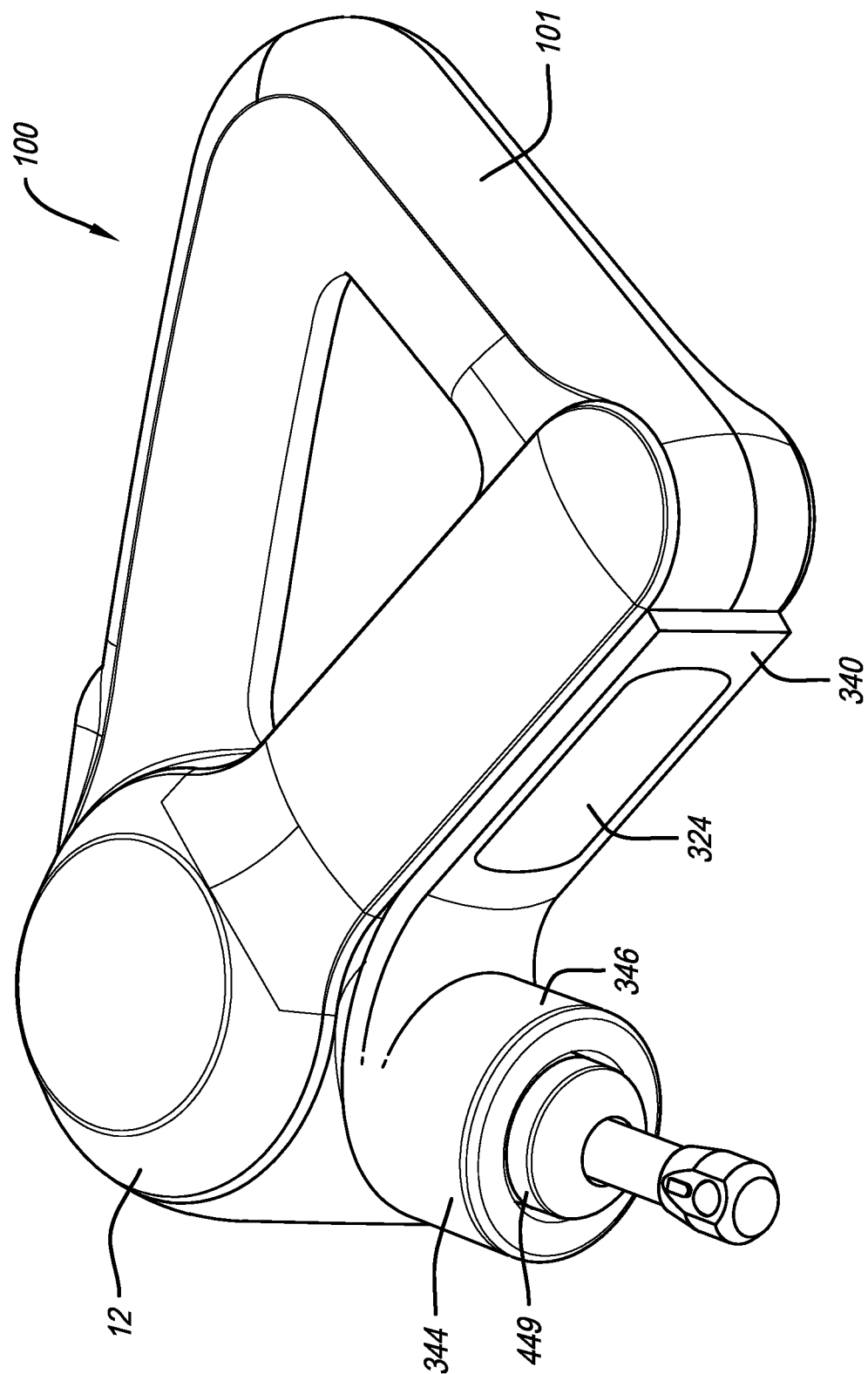
FIG. 56 is a perspective view of a percussive therapy device that includes an attachment module with an extension portion, in accordance with a preferred embodiment of the present invention.
Figure 57:
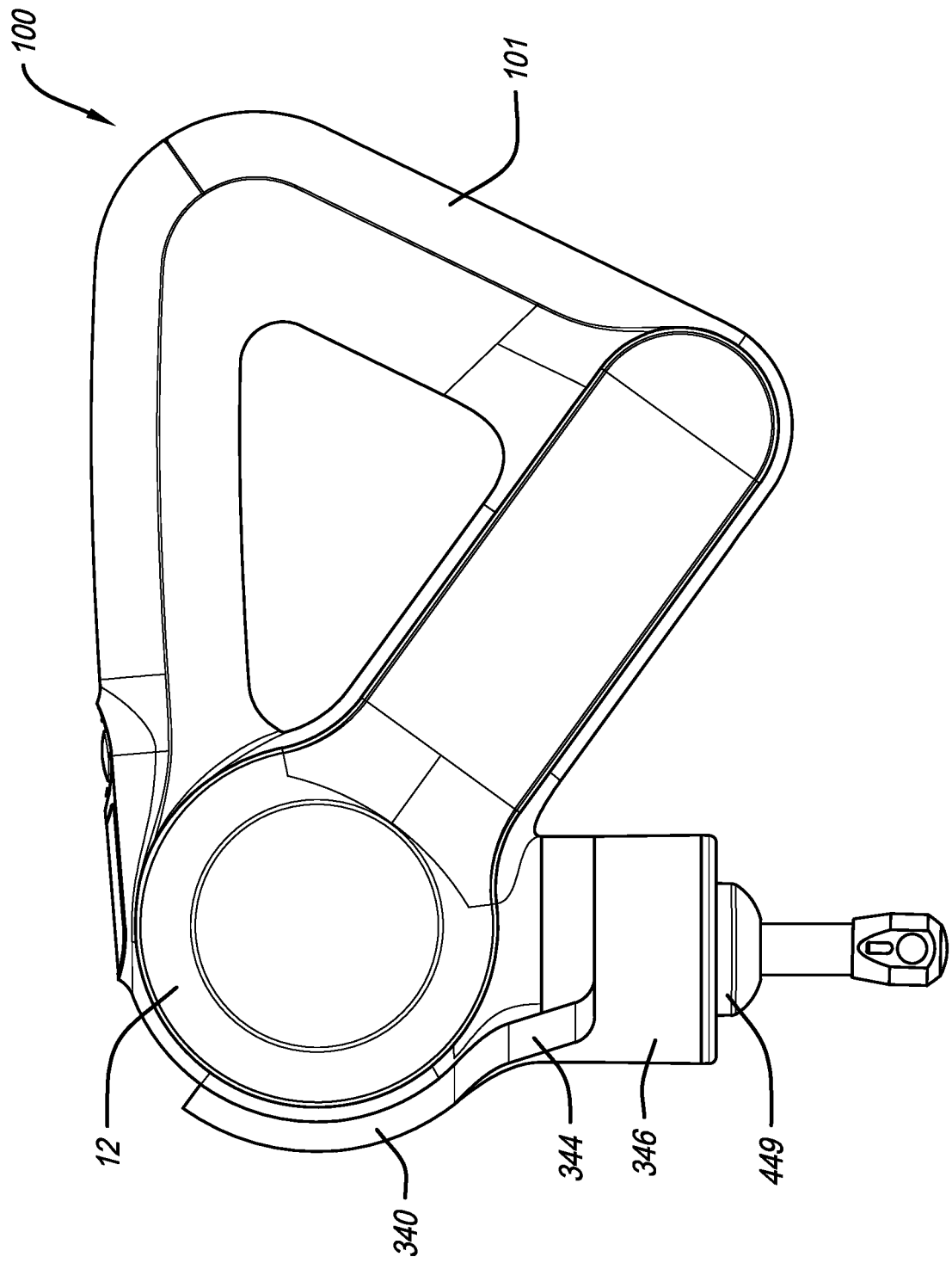
FIG. 57 is a perspective view of a percussive therapy device that includes another attachment module with an extension portion, in accordance with a preferred embodiment of the present invention.

FIGS. 56-57 show other embodiments of attachment modules that include extension portions 340 that extend over a portion of the housing 101 of the percussive therapy device 101. FIG. 56 shows an attachment module 342 that is seated and connects in the same way as attachment module 330, but includes an extension portion 340 that extends over the bottom of the third handle portion 147. FIG. 57 shows an attachment module 344 that is seated and connects in the same way as attachment module 330, but includes an extension portion 340 that extends over the head portion 12 or front of the device. The extension portion 340 can include any of the components that provide an active effect that are discussed herein. In the exemplary drawing of FIG. 56, the extension portion includes a heating elements 324. The ring portion 346 (the portion that is secured over and around the portion of the housing 101 that surrounds the push rod assembly) can also include a component that provides an active effect, such as light therapy. It will be appreciated that the extension portion that extends around the head 12 can also be a separate attachment module that attaches at that location, as opposed to extending from the ring portion 346.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

Embodiments are envisioned where any of the aspects, features, component or steps herein may be omitted and/or are option. Furthermore, where appropriate any of these optional aspects, features, component or steps discussed herein in relation to one aspect of the invention may be applied to another aspect of the invention.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed, at different times. Further any specific numbers noted herein are only examples: alternative implementations may employ differing values or ranges.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges. It will be appreciated that any dimensions given herein are only exemplary and that none of the dimensions or descriptions are limiting on the present invention.

The teachings of the disclosure provided herein can be applied to other systems, not necessarily the system described above. The elements and acts of the various embodiments described above can be combined to provide further embodiments.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will begin with the words "means for"). Accordingly, the applicant reserves the right to add additional claims after filing the application to pursue such additional claim forms for other aspects of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A percussive therapy device comprising:
   a housing;
   an electrical source;
   a motor positioned in the housing;
   a switch for activating the motor;
   a push rod assembly operatively connected to the motor and configured to reciprocate in response to activation of the motor, wherein a massage attachment is configured to be removably received on a distal end of the push rod assembly at a first location; and
   an attachment module configured to:
      associate with the housing of the percussive therapy device at a second location that is different from the first location,
      connect to an outer side the housing of the percussive therapy device at the second location at a same time the massage attachment is received on the distal end of the push rod assembly, and
      provide an active effect;
   wherein the attachment module is configured to be removable from the housing of the percussive therapy device; and
   the housing includes a first electrical connector, and wherein the attachment module includes a second electrical connector in electrical communication with the first electrical connector, wherein connection of the first and second electrical connectors provides electrical communication between the electrical source and the attachment module.

2. The percussive therapy device of claim 1, wherein the active effect is at least one of cold therapy, heat therapy, LED light therapy, photobiomodulation therapy, obtaining biometric data of a user, angular position data of the percussive therapy device, or linear position data of the percussive therapy device.

3. The percussive therapy device of claim 1, wherein connection of the first and second electrical connectors provides data communication between the percussive therapy device and the attachment module.

4. The percussive therapy device of claim 1, wherein the housing includes a handle portion, and wherein the attachment module is associated with the handle portion.

5. The percussive therapy device of claim 1, wherein at least a portion of the attachment module surrounds at least a portion of the push rod assembly.

6. The percussive therapy device of claim 1, wherein the attachment module includes a central opening, and wherein at least a portion of the push rod assembly is configured to reciprocate within and relative to the attachment module.

7. The percussive therapy device of claim 6, wherein the central opening is defined through a ring portion, wherein at least a portion of the push rod assembly is configured to reciprocate within and relative to the ring portion, wherein the attachment module includes an extension portion, and wherein the extension portion is configured to provide the active effect.

8. The percussive therapy device of claim 1, wherein the attachment module includes a heart rate sensor configured to obtain heart rate data of a user.

9. A percussive therapy device comprising:
   a housing;
   an electrical source;
   a motor positioned in the housing;
   a switch for activating the motor;
   a push rod assembly operatively connected to the motor and configured to reciprocate in response to activation of the motor, wherein a massage attachment is configured to be removably received on a distal end of the push rod assembly; and
   an attachment module configured to:
      removably secure to an outer side of the housing at a different location from the massage attachment at a same time the massage attachment is removably received on the distal end of the push rod assembly, and
      electrically communicate with the electrical source;
   wherein the attachment module is removably received in a modular recess defined in the housing.

10. The percussive therapy device of claim 9, wherein the housing includes a handle portion, and wherein the modular recess is defined in the handle portion.

11. The percussive therapy device of claim 9, wherein the attachment module is configured to provide an active effect.

12. A percussive therapy device comprising:
   a housing;
   an electrical source;
   a motor positioned in the housing;
   a switch for activating the motor;
   a push rod assembly operatively connected to the motor and configured to reciprocate in response to activation of the motor, wherein a massage attachment is configured to be removably received on a distal end of the push rod assembly; and
   an attachment module configured to:
   removably secure to an outer side of the housing at a different location from the massage attachment at a same time the massage attachment is removably received on the distal end of the push rod assembly, and
   electrically communicate with the electrical source;
   wherein the attachment module includes a central opening, and wherein at least a portion of the push rod assembly is configured to reciprocate within and relative to the attachment module.

* * * * *